(12) United States Patent
Volosin et al.

(10) Patent No.: US 12,213,812 B2
(45) Date of Patent: *Feb. 4, 2025

(54) MONITORING PHYSIOLOGICAL STATUS BASED ON BIO- VIBRATIONAL AND RADIO FREQUENCY DATA ANALYSIS

(71) Applicant: ZOLL Medical Corporation, Chelmsford, MA (US)

(72) Inventors: Kent Volosin, Mars, PA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/494,359

(22) Filed: Oct. 25, 2023

(65) Prior Publication Data

US 2024/0074710 A1    Mar. 7, 2024

Related U.S. Application Data

(63) Continuation of application No. 17/156,919, filed on Jan. 25, 2021, now Pat. No. 11,826,174, which is a
(Continued)

(51) Int. Cl.
*A61B 5/00* (2006.01)
*A61B 5/05* (2021.01)
(Continued)

(52) U.S. Cl.
CPC .............. *A61B 5/7275* (2013.01); *A61B 5/05* (2013.01); *A61B 5/0535* (2013.01);
(Continued)

(58) Field of Classification Search
None
See application file for complete search history.

(56) References Cited

U.S. PATENT DOCUMENTS

| 4,576,170 A | 3/1986 | Bradley et al. |
| 4,580,572 A | 4/1986 | Granek et al. |

(Continued)

FOREIGN PATENT DOCUMENTS

| CN | 101553163 A | 10/2009 |
| CN | 105942997 A | 9/2016 |

(Continued)

OTHER PUBLICATIONS

Zoll Medical Corporation, LifeVest Model WCD 3000 Operator's Manual, 2012, Pittsburgh, PA.
(Continued)

*Primary Examiner* — Curtis A Kuntz
*Assistant Examiner* — Jerold B Murphy
(74) *Attorney, Agent, or Firm* — Finch & Maloney PLLC

(57) ABSTRACT

A patient monitoring device includes an ECG sensor coupled to a patient, a sensor coupled to the patient and configured to detect bio-vibrational signals, and a radiofrequency monitoring device configured to produce information responsive to electromagnetic energy reflected from the patient's thoracic cavity. A processor processes the ECG signals, the bio-vibrational signals, and the radio frequency information to generate a plurality of physiological parameters of the patient. The processor also performs at least one of a predictive analysis and a trend analysis of the plurality of physiological parameters to determine a current clinical condition of the patient. The trend analysis includes determining a substantial relationship between changes in the plurality of physiological parameters. The processor can also compare the current clinical condition of the patient to predetermined clinically actionable criteria to determine one or more clinically actionable events and provide an output relating to one or more clinically actionable events.

24 Claims, 20 Drawing Sheets

Related U.S. Application Data continuation of application No. 16/355,171, filed on Mar. 15, 2019, now Pat. No. 10,932,726.

(60) Provisional application No. 62/644,216, filed on Mar. 16, 2018.

(51) Int. Cl.
*A61B 5/0535* (2021.01)
*A61B 5/11* (2006.01)
*A61B 5/366* (2021.01)
*H04Q 9/00* (2006.01)

(52) U.S. Cl.
CPC ............ *A61B 5/1102* (2013.01); *A61B 5/366* (2021.01); *A61B 5/7264* (2013.01); *H04Q 9/00* (2013.01); *A61B 2562/0219* (2013.01)

(56) References Cited

U.S. PATENT DOCUMENTS

| | | |
|---|---|---|
| 4,583,547 A | 4/1986 | Granek et al. |
| 4,729,377 A | 3/1988 | Granek et al. |
| 4,928,690 A | 5/1990 | Heilman et al. |
| 4,991,217 A | 2/1991 | Garrett et al. |
| 5,078,134 A | 1/1992 | Heilman et al. |
| 5,741,306 A | 4/1998 | Glegyak et al. |
| 5,929,601 A | 7/1999 | Kaib et al. |
| 5,944,669 A | 8/1999 | Kaib |
| 6,016,445 A | 1/2000 | Baura |
| 6,065,154 A | 5/2000 | Hulings et al. |
| 6,097,982 A | 8/2000 | Glegyak et al. |
| 6,253,099 B1 | 6/2001 | Oskin et al. |
| 6,280,461 B1 | 8/2001 | Glegyak et al. |
| 6,336,900 B1 | 1/2002 | Alleckson et al. |
| 6,374,138 B1 | 4/2002 | Owen et al. |
| 6,406,426 B1 | 6/2002 | Reuss et al. |
| 6,546,285 B1 | 4/2003 | Owen et al. |
| 6,681,003 B2 | 1/2004 | Linder et al. |
| 6,889,078 B2 | 5/2005 | Struble et al. |
| 6,889,079 B2 | 5/2005 | Bocek et al. |
| 6,908,437 B2 | 6/2005 | Bardy |
| 7,122,012 B2 | 10/2006 | Bouton et al. |
| 7,149,579 B1 | 12/2006 | Koh et al. |
| 7,340,296 B2 | 3/2008 | Stahmann et al. |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,712,373 B2 | 5/2010 | Nagle et al. |
| 7,725,150 B2 | 5/2010 | Tupin, Jr. et al. |
| 7,831,303 B2 | 11/2010 | Rueter et al. |
| 7,974,689 B2 | 7/2011 | Volpe et al. |
| 7,991,460 B2 | 8/2011 | Fischell et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,369,944 B2 | 2/2013 | Macho et al. |
| 8,406,842 B2 | 3/2013 | Kaib et al. |
| 8,412,323 B2 | 4/2013 | Bauer |
| 8,644,925 B2 | 2/2014 | Volpe et al. |
| 8,649,861 B2 | 2/2014 | Donnelly et al. |
| 8,676,313 B2 | 3/2014 | Volpe et al. |
| 8,706,215 B2 | 4/2014 | Kaib et al. |
| 8,774,917 B2 | 7/2014 | Macho et al. |
| 8,880,196 B2 | 11/2014 | Kaib |
| 8,897,860 B2 | 11/2014 | Volpe et al. |
| 8,904,214 B2 | 12/2014 | Volpe et al. |
| 8,989,837 B2 | 3/2015 | Weinstein et al. |
| 9,002,427 B2 | 4/2015 | Tupin, Jr. et al. |
| 9,283,399 B2 | 3/2016 | Donnelly et al. |
| 9,675,251 B2 | 6/2017 | Saroka et al. |
| 10,595,775 B2 | 3/2020 | Soykan |
| 10,932,726 B2 * | 3/2021 | Volosin ............... A61B 5/366 |
| 11,826,174 B2 * | 11/2023 | Volosin .............. H04Q 9/00 |
| 2001/0031991 A1 | 10/2001 | Russial |
| 2003/0004547 A1 | 1/2003 | Owen et al. |
| 2003/0032988 A1 | 2/2003 | Fincke |
| 2003/0095648 A1 | 5/2003 | Kaib et al. |
| 2005/0131465 A1 | 6/2005 | Freeman et al. |
| 2006/0030781 A1 | 2/2006 | Shennib |
| 2006/0036292 A1 | 2/2006 | Smith et al. |
| 2006/0111641 A1 | 5/2006 | Manera et al. |
| 2006/0211934 A1 | 9/2006 | Hassonjee et al. |
| 2006/0264776 A1 | 11/2006 | Stahmann et al. |
| 2006/0293714 A1 | 12/2006 | Salo et al. |
| 2007/0161913 A1 | 7/2007 | Farrell et al. |
| 2007/0265671 A1 | 11/2007 | Roberts et al. |
| 2008/0033495 A1 | 2/2008 | Kumar |
| 2008/0306560 A1 | 12/2008 | Macho et al. |
| 2008/0306562 A1 | 12/2008 | Donnelly et al. |
| 2008/0312709 A1 | 12/2008 | Volpe et al. |
| 2009/0076363 A1 | 3/2009 | Bly et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0093687 A1 | 4/2009 | Telfort et al. |
| 2009/0138059 A1 | 5/2009 | Ouwerkerk |
| 2009/0234410 A1 | 9/2009 | Libbus et al. |
| 2009/0240133 A1 | 9/2009 | Friedman et al. |
| 2009/0264792 A1 | 10/2009 | Mazar |
| 2009/0292194 A1 | 11/2009 | Libbus et al. |
| 2009/0312650 A1 | 12/2009 | Maile et al. |
| 2010/0052892 A1 | 3/2010 | Allen et al. |
| 2010/0069735 A1 | 3/2010 | Berkner |
| 2010/0076533 A1 | 3/2010 | Dar et al. |
| 2010/0234716 A1 | 9/2010 | Engel |
| 2010/0256462 A1 | 10/2010 | Rappaport et al. |
| 2010/0298899 A1 | 11/2010 | Donnelly et al. |
| 2010/0312297 A1 | 12/2010 | Volpe et al. |
| 2011/0022105 A9 | 1/2011 | Owen et al. |
| 2011/0060215 A1 | 3/2011 | Tupin, Jr. et al. |
| 2011/0105932 A1 | 5/2011 | Bauer et al. |
| 2011/0130800 A1 | 6/2011 | Weinstein et al. |
| 2011/0170692 A1 | 7/2011 | Konrad et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2012/0283794 A1 | 11/2012 | Kaib et al. |
| 2012/0289809 A1 | 11/2012 | Kaib et al. |
| 2012/0293323 A1 | 11/2012 | Kaib et al. |
| 2012/0302860 A1 | 11/2012 | Volpe et al. |
| 2013/0013014 A1 | 1/2013 | Donnelly et al. |
| 2013/0060103 A1 | 3/2013 | Bergida et al. |
| 2013/0060149 A1 | 3/2013 | Song et al. |
| 2013/0085538 A1 | 4/2013 | Volpe et al. |
| 2013/0144355 A1 | 6/2013 | Macho et al. |
| 2013/0218252 A1 | 8/2013 | Kaib et al. |
| 2013/0231711 A1 | 9/2013 | Kaib |
| 2013/0282149 A1 * | 10/2013 | Kuntagod ............... H04W 4/70 |
| | | 700/73 |
| 2013/0324868 A1 | 12/2013 | Kaib et al. |
| 2013/0325078 A1 | 12/2013 | Whiting et al. |
| 2013/0325096 A1 | 12/2013 | Dupelle et al. |
| 2014/0155762 A1 | 6/2014 | Maskara et al. |
| 2014/0163334 A1 | 6/2014 | Volpe et al. |
| 2014/0206974 A1 | 7/2014 | Volpe et al. |
| 2014/0277243 A1 | 9/2014 | Maskara et al. |
| 2014/0288610 A1 | 9/2014 | Freeman |
| 2014/0303680 A1 | 10/2014 | Donnelly et al. |
| 2014/0324112 A1 | 10/2014 | Macho et al. |
| 2015/0005588 A1 | 1/2015 | Herken et al. |
| 2015/0035654 A1 | 2/2015 | Kaib et al. |
| 2015/0039042 A1 | 2/2015 | Amsler et al. |
| 2015/0039053 A1 | 2/2015 | Kaib et al. |
| 2015/0080699 A1 | 3/2015 | Kaib et al. |
| 2015/0224330 A1 | 8/2015 | Kaib et al. |
| 2016/0135706 A1 | 5/2016 | Sullivan et al. |
| 2016/0163187 A1 * | 6/2016 | Treacy ............... A61B 5/7282 |
| | | 340/501 |
| 2016/0235331 A1 | 8/2016 | Iskander et al. |

(56) References Cited

U.S. PATENT DOCUMENTS

| | | | |
|---|---|---|---|
| 2016/0270738 A1* | 9/2016 | Volpe | A61B 5/276 |
| 2016/0345845 A1 | 12/2016 | Ravid et al. | |
| 2017/0065823 A1 | 3/2017 | Kaib et al. | |
| 2017/0143977 A1 | 5/2017 | Kaib et al. | |

FOREIGN PATENT DOCUMENTS

| | | | |
|---|---|---|---|
| CN | 105992552 A | 10/2016 | |
| CN | 106132286 A | 11/2016 | |
| JP | 2002-514107 A | 5/2002 | |
| JP | 2008-302225 A2 | 12/2008 | |
| JP | 2008-302228 A | 12/2008 | |
| JP | 2009-510631 A | 3/2009 | |
| JP | 2010-537767 A2 | 12/2010 | |
| JP | 2018-503885 A | 2/2018 | |
| WO | 1983004171 A1 | 12/1983 | |
| WO | 1998039061 A2 | 9/1998 | |
| WO | 2004078259 A1 | 9/2004 | |
| WO | 2008036396 A2 | 3/2008 | |
| WO | 2009031149 A2 | 3/2009 | |
| WO | 2009122277 A2 | 10/2009 | |
| WO | 2012006524 A1 | 1/2012 | |
| WO | 2013130957 A2 | 9/2013 | |
| WO | 2014097035 A1 | 6/2014 | |
| WO | 2015134556 A1 | 9/2015 | |

OTHER PUBLICATIONS

Bohadana et al., "Fundamentals of Lung Auscultation", N Engl J Med, 370:744-751 (2014).

Köhler et al., "The Principles of Software QRS Detection", IEEE Engineering in Medicine and Biology Magazine, 21 (1):42-57 (Feb. 2002).

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/ull/!66/1/111.

Association for the Advancement of Medical Instrumentation, ANSI/AAMI DF80:2003 Medical Electrical Equipment—Part 2-4: Particular Requirements for the Safety of Cardiac Defibrillators (including Automated External Defibrillators) 2004, ISBN 1-57020-210-9; abstract; p. vi; p. 50, section 107.1.2.

http://web.archive.org/web/20030427001846/http:/www.lifecor.comiimagelib/imageproduct.asp. Published by LifeCor, Inc., 2002, on a webpage owned by LifeCor, Inc.

International Preliminary Report on Patentability for Application No. PCT/US2019/022553 dated Sep. 22, 2020, 11 pages.

PCT Search Report and Written Opinion for PCT Application No. PCT/US19/22553, mailed on Jun. 11, 2019, 13 pages.

* cited by examiner

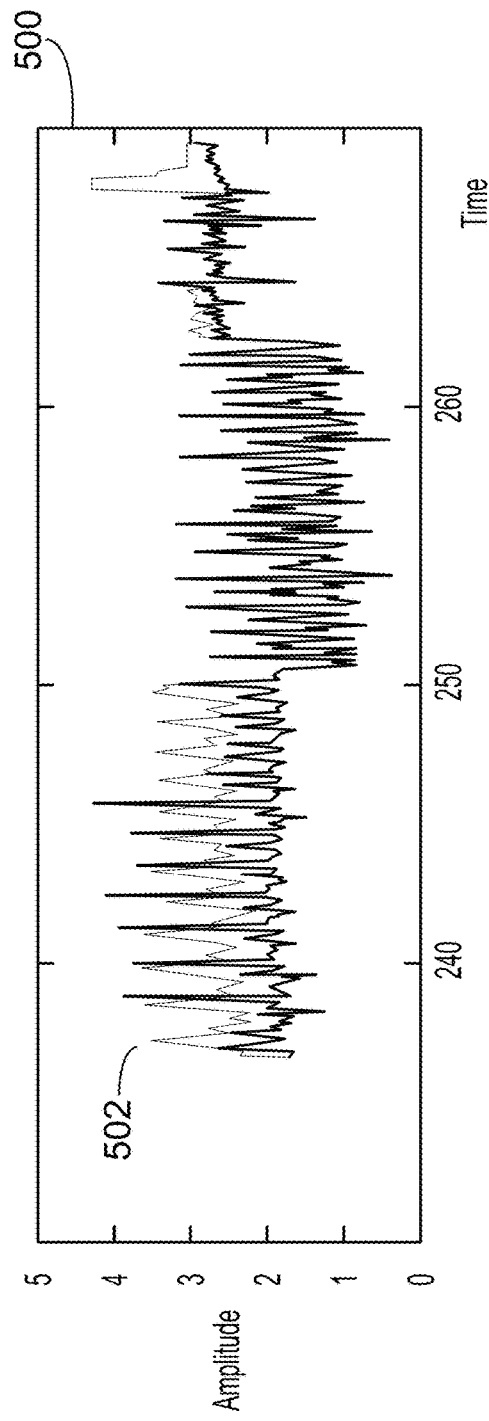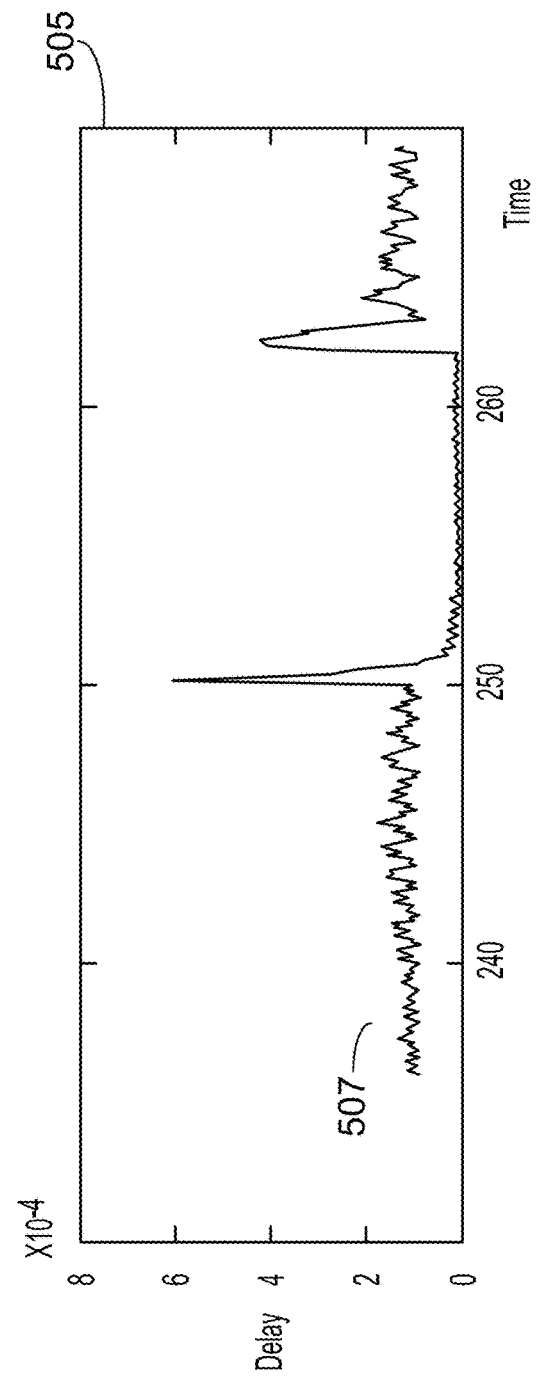
FIG. 5A
FIG. 5B

MONITORING PHYSIOLOGICAL STATUS BASED ON BIO- VIBRATIONAL AND RADIO FREQUENCY DATA ANALYSIS

RELATED APPLICATIONS

This is a continuation of U.S. patent application Ser. No. 17/156,919 (filed 25 Jan. 2021), which is a continuation of U.S. patent application Ser. No. 16/355,171 (filed 15 Mar. 2019), which claims the benefit of U.S. Provisional Patent Application 62/644,216 (filed 16 Mar. 2018). All subject matter set forth in each of the above-referenced applications is hereby incorporated herein by reference in its entirety.

BACKGROUND

The present disclosure is directed to monitoring physiological status of patients based on patient data obtained from multiple sensor sources including bio-vibrational sensors and radio frequency sensors.

Patients suffering from cardiac pathologies tend to have frequent recurrence of acute episodes stemming from congestive heart failure (CHF) conditions. For example, lung congestion is a leading cause of hospitalization and readmission among patients with CIF. Similarly, patients with chronic kidney disease undergoing hemodialysis also suffer from acute adverse events. For example, several patients with end-stage renal disease may have moderate to severe lung congestion before hemodialysis. These patients have a high prevalence of heart failure and overall poor prognosis. There are a wide variety of electronic and mechanical devices for monitoring and treating patients' heart failure conditions. In some examples, depending on the underlying condition being monitored or treated, medical devices such as cardiac monitors or defibrillators may be surgically implanted or externally connected to the patient. In some cases, physicians may use medical devices alone or in combination with drug therapies to treat heart failure conditions.

Left untreated, heart failure could lead to certain life-threatening arrhythmias. Both atrial and ventricular arrhythmias are common in patients with heart failure. One of the deadliest cardiac arrhythmias is ventricular fibrillation, which occurs when normal, regular electrical impulses are replaced by irregular and rapid impulses, causing the heart muscle to stop normal contractions. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity) result in the heart providing insufficient levels of blood flow to the brain and other vital organs for the support of life. It is generally useful to monitor heart failure patients in order to assess heart failure symptoms early and provide interventional therapies as soon as possible.

SUMMARY

In certain implementations, a patient monitoring system includes an ECG sensor coupled to the patient and configured to detect one or more ECG signals of a patient, a vibrational sensor coupled to the patient and configured to detect one or more cardio-vibrational signals of the patient, a radio frequency ultra-wide band transceiver circuit comprising one or more radio frequency antennas and coupled to the patient, and one or more processors. In some examples, the radio frequency ultra-wide band transceiver is configured to cause the one or more radio frequency antennas to direct radio frequency electromagnetic energy into a thoracic cavity of the patient and produce radio frequency information responsive to reflected radio frequency electromagnetic energy received through the one or more radio frequency antennas and reflected from within the thoracic cavity of the patient. In some examples, the one or more processors are configured to process the one or more ECG signals, the one or more cardio-vibrational signals, and the radio frequency information to generate a plurality of physiological parameters of the patient including one or more combinational physiological parameters. The one or more processors can perform at least one of a predictive analysis and a trend analysis of the plurality of physiological parameters including the combinational physiological parameters to determine a current clinical condition of the patient. In implementations described herein, the trend analysis comprises determining a presence of a substantial relationship between changes in the plurality of the physiological parameters. The one or more processors can compare the current clinical condition of the patient to predetermined clinically actionable criteria to determine one or more clinically actionable events and cause an output device to provide an output relating to the one or more clinically actionable events. Implementations of the patient monitoring system as described herein may include one or more of the following features.

In certain implementations of the above patient monitoring system, the trend analysis includes a correlation analysis.

In certain implementations of the above patient monitoring system, the at least one of the predictive analysis and the trend analysis is performed on physiological parameters collected over a prior period of time including one or more of: at least 24 hours, at least 48 hours, at least one week, at least two weeks, at least one month, at least 6 weeks, at least two months, at least 4 months, at least 6 months, at least 1 year, and at least 2 years.

In certain implementations of the above patient monitoring system, the at least one of the predictive analysis and the trend analysis is performed on physiological parameters collected over a prior period of time corresponding to at least an available clinical history of the patient.

In certain implementations of the above patient monitoring system, the one or more clinically actionable events includes at least one of an automated event that is triggered without user input and a manual event that is triggered based upon a user response to the output and comprises one or more instructions to perform one or more actions.

In certain implementations of the above patient monitoring system, the output relating to the one or more clinically actionable event is based on a transgression of one or more thresholds defined with respect to the plurality of physiological parameters or results of the at least one predictive analysis and the trend analysis.

In certain implementations of the above patient monitoring system, performing the predictive analysis includes inputting the plurality of physiological parameters into an artificial neural network and determining the current clinical condition of the patient based upon an output of the artificial neural network.

In certain implementations of the above patient monitoring system, performing the predictive analysis includes inputting the plurality of physiological parameters into a deep learning process and determining the current clinical condition of the patient based upon an output of the deep learning process.

In certain implementations of the above patient monitoring system, performing the predictive analysis includes inputting the plurality of physiological parameters into a machine learning process and determining the current clinical condition of the patient based upon an output of the machine learning process. In some examples, the current clinical condition of the patient includes a predictive score based upon the output of the machine learning process, wherein the predictive score indicates a likelihood of an occurrence of an adverse event. In some examples, the adverse event includes one or more of an arrhythmia event, a stroke event, a syncopal event, and a hospitalization event.

In certain implementations of the above patient monitoring system, performing the trend analysis includes determining whether at least one of the plurality of physiological parameters has exceeded a threshold, correlating the at least one of the plurality of physiological parameters that has exceeded the threshold against at least one additional physiological parameter selected from the plurality of physiological parameters to produce a correlation score, and determining the current clinical condition of the patient based upon the correlation score. In some examples, the correlation score indicates a change in a condition of the patient.

In certain implementations of the above patient monitoring system, the vibrational sensor is further configured to sense one or more lung vibrations for the patient, the one or more lung vibrations comprising at least one of bronchial vibrations, stridor, crackle, wheeze, rhonchus, pleural friction, squawk, glottal, pharyngeal or other vibrations.

In certain implementations of the above patient monitoring system, the one or more ECG signals include at least one of heart rate, heart rate variability, PVC burden or counts, atrial fibrillation burden, pauses, heart rate turbulence, QRS height, QRS width, changes in a size or shape of morphology of the one or more ECG signals, cosine R-T, artificial pacing, QT interval, QT variability, T wave width, T wave alternans, T-wave variability, and ST segment changes.

In certain implementations of the above patient monitoring system, the one or more cardio-vibrational signals include at least one of an S1 vibration, an S2 vibration, an S3 vibration, an S4 vibration, and a heart murmur vibration.

In certain implementations of the above patient monitoring system, the radio frequency information includes a measurement of fluid content within the thoracic cavity of the patient.

In certain implementations of the above patient monitoring system, the plurality of physiological parameters includes one or more of left ventricular systolic time (LVST), electromechanical activation time (EMAT), % LVST, and left ventricle end diastolic pressure (LVEDP).

In certain implementations of the above patient monitoring system, the one or more processors are integrated in a cardiac monitoring device adapted to be worn by the patient.

In certain implementations of the above patient monitoring system, the one or more processors are integrated into a remote processing device.

In certain implementations of the above patient monitoring system, the one or more processors are integrated into a wearable defibrillation device adapted to be worn by the patient.

In certain implementations, a second patient monitoring system includes at least one vibrational sensor coupled to the patient and configured to detect one or more cardio-vibrational signals, at least one radio frequency ultra-wide band transceiver coupled to the patient, and one or more processors. In some examples, the at least one radio frequency ultra-wide band transceiver is configured to direct radio frequency electromagnetic waves through lungs of the patient and detect radio frequency information responsively to the radio frequency electromagnetic waves that have passed through the lungs of the patient. In some examples, the one or more processors are configured to process the detected one or more cardiac vibrational signals over a predetermined duration to determine at least one cardiac vibrational metric of the patient, process the patient's radio frequency information over a predetermined duration to determine at least one lung fluid metric of the patient, determine an output relating to one or more clinically actionable events based on the determined at least one cardiac vibrational metric and the determined at least one lung fluid metric, and cause an output device to provide the output. Implementations of the second patient monitoring system as described herein may include one or more of the following features.

In certain implementations of the above second patient monitoring system, the one or more clinically actionable events include at least one of an automated event that is triggered without user input and a manual event that is triggered based upon a user response to the output and comprises one or more instructions to perform one or more actions.

In certain implementations of the above second patient monitoring system, determining the output includes performing a predictive analysis of the determined value of or a trend in the at least one cardiac vibrational metric and the determined value of or a trend in the at least one lung fluid metric.

In certain implementations of the above second patient monitoring system, performing the predictive analysis includes inputting the determined value of or a trend in the at least one cardiac vibrational metric and the determined value of or a trend in the at least one lung fluid metric into a machine learning process, determining a predictive score based upon an output of the machine learning process, wherein the predictive score indicates a likelihood of an occurrence of an adverse event, and determining the output based upon the predictive score.

In certain implementations of the above second patient monitoring system, determining the output includes performing a trend analysis of changes in the at least one cardiac vibrational metric and the at least one lung fluid metric to determine a presence of a substantial relationship between the changes in the at least one cardiac vibrational metric and the at least one lung fluid metric. In some examples, performing the trend analysis of the changes to detect the presence of a substantial relationship between the changes in the at least one cardiac vibrational metric and the at least one lung fluid metric includes performing a correlation analysis.

In certain implementations of the above second patient monitoring system, determining the output includes performing a correlation analysis, the correlation analysis including processing the one or more cardio-vibrational signals and the radio frequency information to generate a plurality of physiological parameters of the patient including one or more combinational physiological parameters, correlating at least one of the plurality of physiological parameters that has exceeded a threshold against at least one additional physiological parameter selected from the plurality of physiological parameters to produce a correlation score, wherein the correlation score indicates a change in a condition of the patient, and determining the output based upon the correlation score.

In certain implementations of the above second patient monitoring system, the one or more cardio-vibrational signals include at least one of an S1 vibration, an S2 vibration, an S3 vibration, an S4 vibration, ventricular wall motion and a heart murmur vibration.

In certain implementations of the above second patient monitoring system, the radio frequency information includes a measurement of fluid content within the thoracic cavity of the patient.

In certain implementations, a third patient monitoring system includes an ECG sensor coupled to the patient and configured to detect one or more ECG signals of the patient, a vibrational sensor coupled to the patient and configured to detect one or more cardio-vibrational signals of the patient, a radio frequency ultra-wide band transceiver circuit comprising one or more radio frequency antennas and coupled to the patient, and one or more processors. In some examples, the radio frequency ultra-wide band transceiver circuit is configured to cause the one or more radio frequency antennas to direct radio frequency electromagnetic energy into a thoracic cavity of the patient and produce radio frequency information responsive to reflected radio frequency electromagnetic energy received through the one or more radio frequency antennas and reflected from within the thoracic cavity of the patient. In some examples, the one or more processors are configured to process the one or more ECG signals, the one or more cardio-vibrational signals, and the radio frequency information to generate a plurality of physiological parameters of the patient including one or more combinational physiological parameters. The one or more processors can perform a trend analysis of the plurality of physiological parameters including the combinational physiological parameters to produce a trend result, update a monitoring schedule for the patient based upon the trend result, determine a current clinical condition of the patient based upon the trend result, and compare the current clinical condition of the patient to predetermined clinically actionable criteria to determine one or more clinically actionable events. The one or more processors can cause an output device to provide an output relating to the one or more clinically actionable events. Implementations of the third patient monitoring system as described herein may include one or more of the following features.

In certain implementations of the above third patient monitoring system, the one or more processors are further configured to process the one or more ECG signals, the one or more cardio-vibrational signals, and the radio frequency information according to the updated monitoring schedule to generate a plurality of updated physiological parameters of the patient; perform a trend analysis of the plurality of updated physiological parameters including the one or more combinational physiological parameters to produce an updated trend result; and determine an updated clinical condition of the patient based upon the updated trend result.

In certain implementations of the above third patient monitoring system, the one or more clinically actionable events include at least one of an automated event that is triggered without user input and a manual event that is triggered based upon a user response to the output and comprises one or more instructions to perform one or more actions.

In certain implementations of the above third patient monitoring system, the one or more ECG signals include at least one of heart rate, heart rate variability, PVC burden or counts, atrial fibrillation burden, pauses, heart rate turbulence, QRS height, QRS width, changes in a size or shape of morphology of the one or more ECG signals, cosine R-T, artificial pacing, QT interval, QT variability, T wave width, T wave alternans, T-wave variability, and ST segment changes.

In certain implementations of the above third patient monitoring system, the one or more cardio-vibrational signals include at least one of an S1 vibration, an S2 vibration, an S3 vibration, an S4 vibration, and a heart murmur vibration.

In certain implementations of the above third patient monitoring system, the radio frequency information includes a measurement of fluid content within the thoracic cavity of the patient.

In certain implementations, a fourth patient monitoring system includes an ECG sensor coupled to the patient and configured to detect one or more ECG signals of the patient, a vibrational sensor coupled to the patient and configured to detect one or more cardio-vibrational signals of the patient, a radio frequency ultra-wide band transceiver circuit comprising one or more radio frequency antennas and positioned on the patient over at least one main artery, and one or more processors. In some examples, the radio frequency ultra-wide band transceiver circuit is configured to cause the one or more radio frequency antennas to direct radio frequency electromagnetic energy into at least a portion of the patient and produce radio frequency information responsive to reflected radio frequency electromagnetic energy received through the one or more radio frequency antennas and reflected from within the at least a portion of the patient. In some examples, the one or more processors are configured to process the one or more ECG signals, the one or more cardio-vibrational signals, and the radio frequency information to generate a plurality of physiological parameters of the patient including one or more combinational physiological parameters. The one or more processors can perform at least one of a predictive analysis and a trend analysis of the plurality of physiological parameters including the combinational physiological parameters to determine a current clinical condition of the patient; compare the current clinical condition of the patient to predetermined clinically actionable criteria to determine one or more clinically actionable events and cause an output device to provide an output relating to one or more clinically actionable events. Implementations of the fourth patient monitoring system as described herein may include one or more of the following features.

In certain implementations of the above fourth patient monitoring system, the at least one main artery includes at least one of the radial artery, the brachial artery, the aorta, and one or more pulmonary arteries.

In certain implementations of the above fourth patient monitoring system, the radio frequency information includes at least one of blood pressure information, heart wall motion information, blood flow information, heart rhythm information, and fluid content information.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples and are incorporated in and constitute a part of this specification but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

FIGS. 5A and 5B depict schematic plots of propagation delay and amplitude of radio frequency waves reflected from patient tissue, in accordance with an example of the present disclosure.

DETAILED DESCRIPTION

Figure 1:
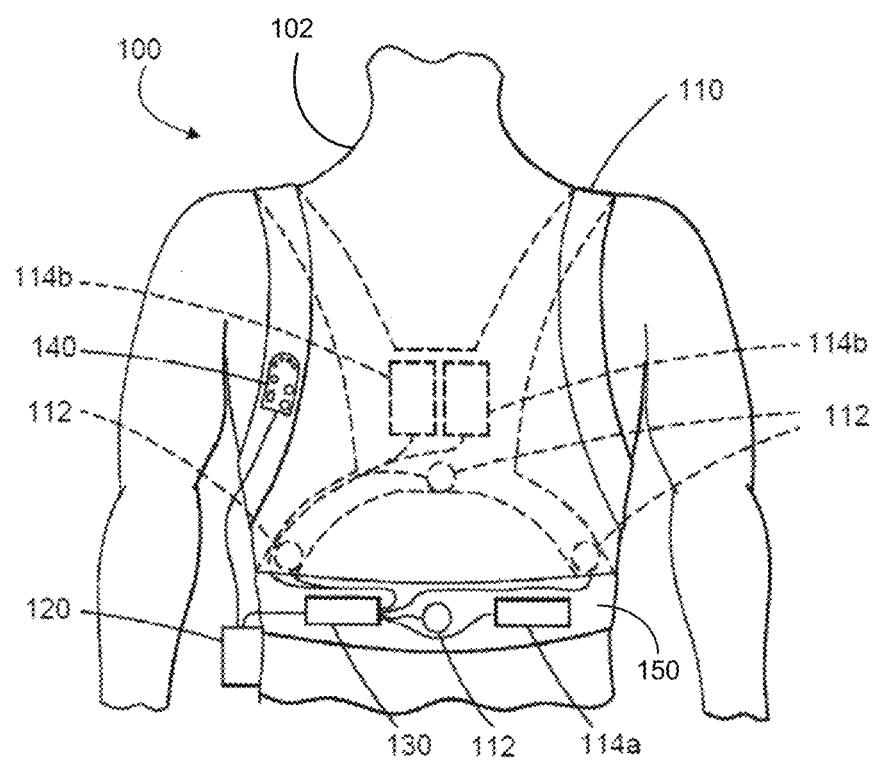
FIG. 1 depicts a wearable medical device, in accordance with an example of the present disclosure.

Wearable medical devices, such as cardiac event monitoring devices, are used in clinical or outpatient settings to monitor and record various physiological signals for a patient. These signals can be used to determine a current condition for a patient as well as to predict, plan and prepare for future adverse events such as cardiac events that may occur or other adverse changes to a patient's medical health. For example, ECG monitoring in combination with a patient's medical history can be used by, for example, a machine learning process to calculate a risk score for a patient and predict, for example, a future occurrence of a potential cardiac arrhythmia event. Examples of such a machine learning process are described in U.S. Patent Application Publication No. 2016/0135706 entitled "Medical Premonitory Event Estimation," the content of which is incorporated herein by reference.

In some implementations, a patient monitoring system can include sensors configured to collect patient physiological signals beyond ECG signals. For example, a vibrational sensor can be configured to collect bio-vibrational signals such as cardiac-vibrational signals, e.g., S1, S2, S3, and S4 signals, and pulmonary-vibrational signals, e.g., vibrational signals from the lung or other airway-related anatomical region such as the trachea, and pharynx, among others. Additionally, a radio frequency sensor such as an ultra-wide band transceiver circuit can be configured to collect information responsive to radio frequency electromagnetic energy reflected from within a patient's thoracic cavity and/or the heart. For example, the radio frequency sensor can be configured to monitor transthoracic (e.g., lung) fluid levels and changes relating to the same. In implementations described herein, a processing device can further process the various collected signals and related information from the different underlying physiological sensors to produce one or more combinational physiological parameters, e.g., physiological parameters that are determined based upon two or more different underlying physiological sensors and related information. At least one of a predictive analysis (e.g., using a machine learning process such as an artificial neural network) and a trends analysis (e.g., a correlation analysis) can be performed on the collected signals and received information as well as the combinational metrics to determine a current condition for the patient as well as one or more clinically actionable events.

For example, the present disclosure relates to a patient monitoring device and system. The device or system can include an ECG sensor coupled to the patient and configured to detect one or more ECG signals of the patient, a sensor coupled to the patient and configured to detect one or more bio-vibrational signals (including cardio-vibrational or pulmonary-vibrational signals) of the patient, and a radio frequency-based monitoring device including radio frequency antennas and associated transceiver circuitry that is coupled to the patient and configured to direct radio frequency electromagnetic energy into the patient's thoracic cavity and/or towards the heart. The radio frequency transceiver circuitry produces a plurality of measurements responsive to radio frequency electromagnetic energy reflected from the patient's thoracic cavity and/or the heart and received via a receiving radio frequency antenna. One or more processors process the one or more ECG signals, the one or more cardio-vibrational or pulmonary-vibrational signals, and the radio frequency measurements to generate a plurality of physiological parameters of the patient including one or more combinational physiological parameters. Further, the processors can be further configured to perform at least one of a predictive analysis and a trend analysis of the plurality of physiological parameters including the combinational physiological parameters to determine a current clinical condition of the patient. In some implementations, the patient monitoring device coupled to the patient can transmit the physiological information measured from the patient to a remote server for analysis. At the remote server, one or more processors can be configured to perform at least one of a predictive analysis and a trend analysis of the plurality of physiological parameters in accordance with the principles described herein. For example, the trend analysis can include determining a presence of a substantial relationship between changes in the plurality of physiological parameters. The one or more processors can also compare the current clinical condition of the patient to predetermined clinically actionable criteria to determine one or more clinically actionable events and cause an output device to provide an output relating to one or more clinically actionable events.

As an example, a patient may be examined by a healthcare provider at an outpatient facility and asked to use one or more of the wearable patient monitoring devices described herein for monitoring a set of patient physiological parameters. For example, the monitoring may be initiated on just one set of physiological parameters, such as ECG based metrics. Over time or in response to certain conditions as described herein, additional sets of physiological parameters beyond ECG parameters, such as bio-vibrational parameters or radio frequency-based parameters (or combinational parameters thereof) may be initiated. Based upon the collected set of physiological parameters, the device can execute a process to assess a current clinical condition of the patient. In follow-up visits (e.g. once a week, two weeks, or month), the device can provide updated information about the clinical condition of the patient. The device can also be configured to determine whether the patient is at high risk for developing heart failure symptoms that could require eventual hospitalization. The patient and/or their physician can be notified of the determination and appropriate interventional actions may be taken. For example, the patient's medications can be adjusted, and the physician can initiate closer outpatient monitoring and schedule additional office visits. To further the above example, once identified as high risk for heart failure, the patient can be upgraded to a wearable monitoring and treatment device such as a wearable cardioverter defibrillator (WCD) for an extended period of time. Such a device can monitor a patient's cardiac condition and, if warranted, provide one or more therapeutic defibrillation and/or pacing pulses to the patient. The wearable cardioverter defibrillator can continue collect updated physiological information during use by the patient. This updated information is also provided to the physician, who can continue to monitor changes in the patient's health by analyzing changes in trends associated with the updated physiological information. For example, this analysis can guide further therapy changes and provide information as to when acute heart failure risk has been reduced.

A number of patients suffering from cardiac pathologies also suffer from conditions relating to thoracic fluid management and thus have frequent recurrence of acute episodes. Among such patients may be those with congestive heart failure (CHF). Lung congestion is a leading cause of hospitalization and readmission among patients with CHF. Thus, it is desirable to measure and monitor the degree of lung congestion. The radio frequency sensor described herein can allow for direct and accurate measurement of fluid including through the monitoring of changes to the patient's thoracic impedance. Such information can be used by a caregiver in coordinating the patient's treatment regimen and has the potential to shorten the hospitalization period by enabling effective drug balance. For example, the technology can provide early edema detection to prevent hospital readmission.

Similarly, patients with chronic kidney disease (CKD) undergoing hemodialysis also require fluid management strategies. In patients with end-stage renal disease (ESRD), approximately 60% may have moderate to severe lung congestion before hemodialysis. Further, patients diagnosed with CKD and undergoing maintenance hemodialysis tend to have a high prevalence of heart failure (HF) and overall poor prognosis. Congestive heart failure is thus a frequent clinical manifestation in dialysis patients. For these reasons, fluid assessment and management can be useful for managing CKD and HF. In this disclosure, a non-invasive, wearable monitoring system can be used to assess thoracic impedance and/or fluid changes and combine and/or analyze this information in conjunction with bio-vibrational information, ECG information, and other combinational metrics.

Such an approach provides several advantages over existing monitoring and prediction techniques. By combining physiological measurements from multiple sensor sources, and using various types of analysis to both verify and measure change in the physiological signals, the present disclosure provides a more robust and accurate analysis of a patient's current condition and a likelihood of changes to the patient's condition. Based upon this information, a personalized treatment regimen can be created and regularly updated for the patient while regularly monitoring the patient's condition for positive or negative changes.

The teachings of the present disclosure can be generally applied to extracting physiological metrics from external medical monitoring and/or treatment devices (e.g., devices that are not completely implanted within the patient's body) for further processing. External medical devices can include, for example, ambulatory medical devices that are capable of and designed for moving with the patient as the patient goes about his or her daily routine. An example ambulatory medical device can be a wearable medical device such as a wearable cardioverter defibrillator (WCD), a wearable cardiac monitoring device, an in-hospital device such as an in-hospital wearable defibrillator (HWD), a short-term wearable cardiac monitoring and/or therapeutic device, mobile cardiac monitoring devices, and other similar wearable medical devices.

The wearable medical device can be capable of continuous use by the patient. In some implementations, the continuous use can be substantially or nearly continuous in nature. That is, the wearable medical device may be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless qualify as continuous use. For example, the wearable medical device can be configured to be worn by a patient for as many as 24 hours a day. In some implementations, the patient may remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other caregiver provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., electrocardiogram (ECG) information, including arrhythmia information, cardio-vibrations, pulmonary-vibrations, etc.) and/or non-cardiac information (e.g., blood oxygen, the patient's temperature, glucose levels, tissue fluid levels, and/or lung vibrations). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. For example, the wearable medical device can be configured to monitor, for example, pulmonary-vibrations (e.g., using microphones and/or accelerometers), breath vibrations, sleep related parameters (e.g., snoring, sleep apnea), tissue fluids (e.g., using radio frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the wearable medical devices described herein can be pacing-enabled, e.g., capable of providing therapeutic pacing pulses to the patient.

In implementations, an example therapeutic medical device can include an in-hospital continuous monitoring defibrillator and/or pacing device, for example, an in-hospital wearable defibrillator. In such an example, the electrodes can be adhesively attached to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. In an example implementation, the electrodes can include a front adhesively attachable therapy electrode, a back adhesively attachable therapy electrode, and a plurality of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device may be confined to a hospital bed or room for a significant amount of time (e.g., 90% or more of the patient's stay in the hospital). As a result, a user interface can be configured to interact with a user other than the patient, e.g., a nurse, for device-related functions such as initial device baselining, setting and adjusting patient parameters, and changing the device batteries.

In implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator described above.

In some implementations, the medical device may be a patient monitoring device with no treatment or therapy functions. For example, such a patient monitoring device can include a cardiac monitoring device or a cardiac monitor that is configured to monitor one or more cardiac physiological parameters of a patient, e.g., for remotely monitoring and/or diagnosing a condition of the patient. For example, such cardiac physiological parameters may include a patient's ECG information, cardio-vibrations (e.g., using accelerometers or microphones), and other related cardiac information. A cardiac monitoring device is a portable device that the patient can carry around as he or she goes about their daily routine. The cardiac monitor may be configured to detect the patient's ECG through a plurality of cardiac sensing electrodes. For example, a cardiac monitor may be attached to a patient via at least three adhesive cardiac sensing electrodes disposed about the patient's torso. Such cardiac monitors are used in cardiac event monitoring, e.g., in patient populations reporting irregular cardiac symptoms and/or conditions. Example cardiac conditions can include atrial fibrillation, bradycardia, tachycardia, atrioventricular block, Lown-Ganong-Levine syndrome, atrial flutter, sino-atrial node dysfunction, cerebral ischemia, syncope, atrial pause, and/or heart palpitations. For example, such patients may be prescribed a cardiac monitor for an extended period of time, e.g., 10 to 30 days, or more. In some mobile cardiac event monitoring applications, a portable cardiac monitor can be configured to substantially continuously monitor the patient for a cardiac anomaly, and when such an anomaly is detected, the monitor may automatically send data relating to the anomaly to a remote server. The remote server may be located within a 24-hour manned monitoring center, where the data is interpreted by qualified, cardiac-trained reviewers and/or caregivers, and feedback provided to the patient and/or a designated caregiver via detailed periodic or event-triggered reports. In certain cardiac event monitoring applications, the cardiac monitor is configured to allow the patient to manually press a button on the cardiac monitor to report a symptom. For example, a patient may report symptoms such as a skipped beat, shortness of breath, light headedness, racing heart rate, fatigue, fainting, chest discomfort, weakness, dizziness, and/or giddiness. The cardiac monitor can record predetermined physiologic parameters of the patient (e.g., ECG information) for a predetermined amount of time (e.g., 1-30 minutes before and 1-30 minutes after a reported symptom).

The cardiac monitor can be configured to monitor physiologic parameters of the patient other than cardiac related parameters. For example, the cardiac monitor can be configured to monitor, for example, cardio-vibrations (e.g., using accelerometers or microphones), lung vibrations, breath vibrations, sleep related parameters (e.g., snoring, sleep apnea), tissue fluids, among others.

FIG. 1 illustrates an example medical device 100 that is external, ambulatory, and wearable by a patient 102, and configured to implement one or more configurations described herein. For example, the medical device 100 can be a non-invasive medical device configured to be located substantially external to the patient. Such a medical device 100 can be, for example, an ambulatory medical device that is capable of and designed for moving with the patient as the patient goes about his or her daily routine. For example, the medical device 100 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 100 can include one or more of the following: a garment 110, one or more sensing electrodes 112 (e.g., ECG electrodes), one or more therapy electrodes 114a and 114b (collectively referred to herein as therapy electrodes 114), a medical device controller 120, a connection pod 130, a patient interface pod 140, a belt 150, or any combination of these. In some examples, at least some of the components of the medical device 100 can be configured to be affixed to the garment 110 (or in some examples, permanently integrated into the garment 110), which can be worn about the patient's torso.

The medical device controller 120 can be operatively coupled to the sensing electrodes 112, which can be affixed to the garment 110, e.g., assembled into the garment 110 or removably attached to the garment, e.g., using hook and loop fasteners. In some implementations, the sensing electrodes 112 can be permanently integrated into the garment 110. The medical device controller 120 can be operatively coupled to the therapy electrodes 114. For example, the therapy electrodes 114 can also be assembled into the garment 110, or, in some implementations, the therapy electrodes 114 can be permanently integrated into the garment 110.

Component configurations other than those shown in FIG. 1 are possible. For example, the sensing electrodes 112 can be configured to be attached at various positions about the body of the patient 102. The sensing electrodes 112 can be operatively coupled to the medical device controller 120 through the connection pod 130. In some implementations, the sensing electrodes 112 can be adhesively attached to the patient 102. In some implementations, the sensing electrodes 112 and at least one of the therapy electrodes 114 can be included on a single integrated patch and adhesively applied to the patient's body.

The sensing electrodes 112 can be configured to detect one or more cardiac signals. Examples of such signals include ECG signals and/or other sensed cardiac physiological signals from the patient. In certain implementations, the sensing electrodes 112 can include additional components such as accelerometers, vibrational signal detecting devices, and other measuring devices for recording additional parameters. For example, the sensing electrodes 112 can also be configured to detect other types of patient physiological parameters and vibrational signals, such as tissue fluid levels, cardio-vibrations, pulmonary-vibrations, respiration-related vibrations of anatomical features in the airway path, patient movement, etc. Example sensing electrodes 112 include a metal electrode with an oxide coating such as tantalum pentoxide electrodes, as described in, for example, U.S. Pat. No. 6,253,099 entitled "Cardiac Monitoring Electrode Apparatus and Method," the content of which is incorporated herein by reference.

In some examples, the therapy electrodes 114 can also be configured to include sensors configured to detect ECG signals as well as other physiological signals of the patient. The connection pod 130 can, in some examples, include a signal processor configured to amplify, filter, and digitize these cardiac signals prior to transmitting the cardiac signals to the medical device controller 120. One or more of the therapy electrodes 114 can be configured to deliver one or more therapeutic defibrillating shocks to the body of the patient 102 when the medical device 100 determines that such treatment is warranted based on the signals detected by the sensing electrodes 112 and processed by the medical device controller 120. Example therapy electrodes 114 can include conductive metal electrodes such as stainless-steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 114 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) or a patient. Alternatively, the optional therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Figure 2:
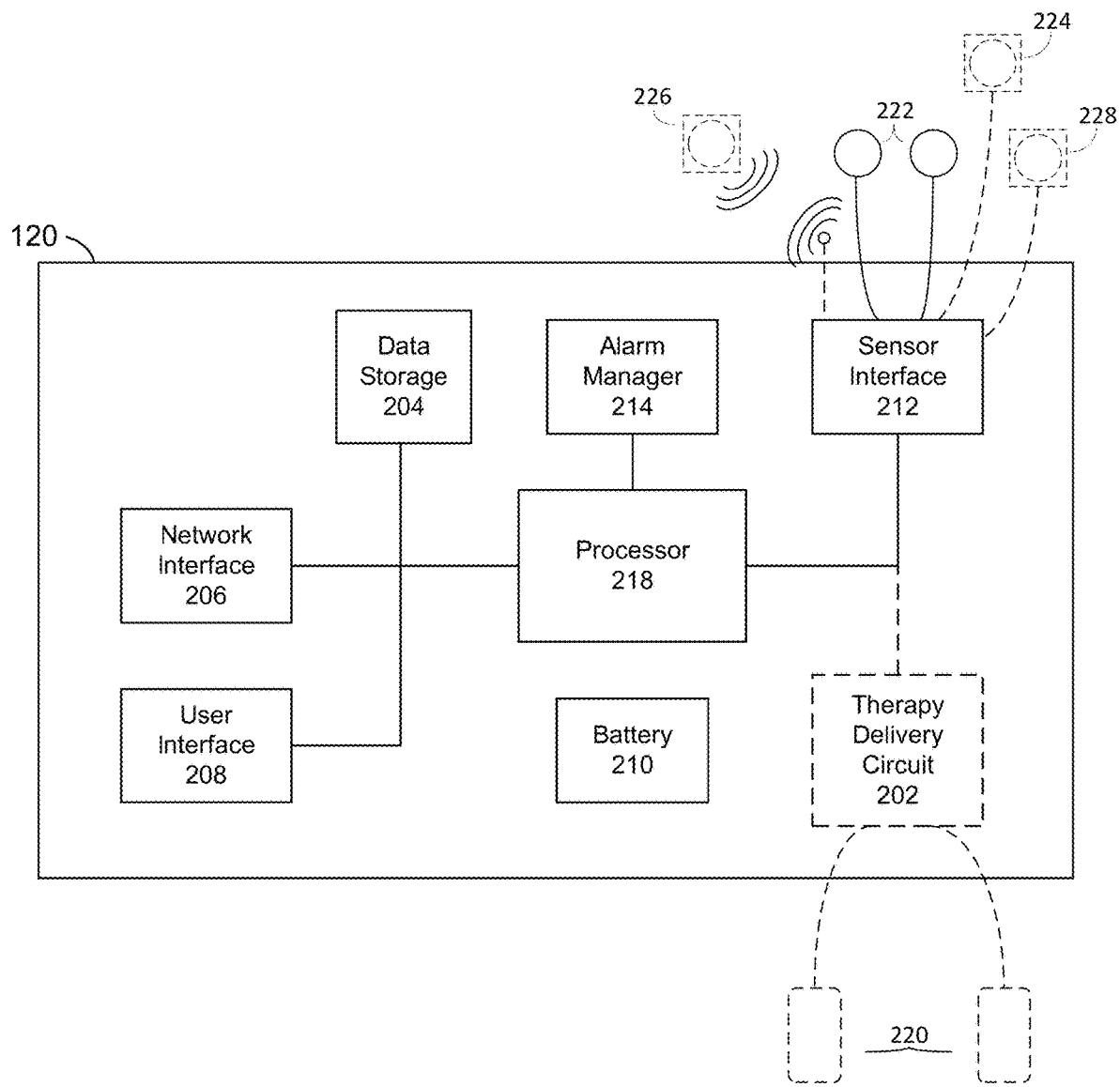
FIG. 2 depicts a schematic view of a sample controller for a wearable medical device such as that shown in FIG. 1, in accordance with an example of the present disclosure.

FIG. 2 illustrates a sample component-level view of the medical device controller 120. As shown in FIG. 2, the medical device controller 120 can include a therapy delivery circuitry 202, a data storage 204, a network interface 206, a user interface 208, at least one battery 210, a sensor interface 212, an alarm manager 214, and least one processor 218. A patient monitoring medical device can include a medical device controller 120 that includes like components as those described above but does not include the therapy delivery circuitry 202 (shown in dotted lines).

The therapy delivery circuitry 202 can be coupled to one or more electrodes 220 configured to provide therapy to the patient (e.g., therapy electrodes 114 as described above in connection with FIG. 1). For example, the therapy delivery circuitry 202 can include, or be operably connected to, circuitry components that are configured to generate and provide the therapeutic shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuitry and under control of one or more processors (e.g., processor 218) to provide, for example, one or more pacing or defibrillation therapeutic pulses.

Pacing pulses can be used to treat cardiac arrhythmias such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). These capacitors can be switched into a series connection during discharge for a defibrillation pulse. For example, four capacitors of approximately 650 uF can be used. The capacitors can have between a 350 to 500-volt surge rating and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuitry 202 can be configured to perform the switching and pulse delivery operations, e.g., under control of the processor 218. As the energy is delivered to the patient, the amount of energy being delivered can be tracked. For example, the amount of energy can be kept to a predetermined constant value even as the pulse waveform is dynamically controlled based on factors such as the patient's body impedance.

The data storage 204 can include one or more of non-transitory computer readable media, such as flash memory, solid state memory, magnetic memory, optical memory, cache memory, combinations thereof, and others. The data storage 204 can be configured to store executable instructions and data used for operation of the medical device controller 120. In certain implementations, the data storage can include executable instructions that, when executed, are configured to cause the processor 218 to perform one or more functions.

In some examples, the network interface 206 can facilitate the communication of information between the medical device controller 120 and one or more other devices or entities over a communications network. For example, where the medical device controller 120 is included in an ambulatory medical device (such as medical device 100), the network interface 206 can be configured to communicate with a remote computing device such as a remote server or other similar computing device. The network interface 206 can include communications circuitry for transmitting data in accordance with a Bluetooth® wireless standard for exchanging such data over short distances to an intermediary device(s), e.g., base station, "hotspot" device, smartphone, tablet, portable computing device, and/or other devices in proximity of the wearable medical device. The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain implementations, the user interface 208 can include one or more physical interface devices such as input devices, output devices, and combination input/output devices and a software stack configured to drive operation of the devices. These user interface elements may render visual, audio, and/or tactile content. Thus, the user interface 208 may receive input or provide output, thereby enabling a user to interact with the medical device controller 120.

The medical device controller 120 can also include at least one battery 210 configured to provide power to one or more components integrated in the medical device controller 120. The battery 210 can include a rechargeable multi-cell battery pack. In one example implementation, the battery 210 can include three or more 2200 mAh lithium ion cells that provide electrical power to the other device components within the medical device controller 120. For example, the battery 210 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 120.

The sensor interface 212 can be coupled to one or more sensors configured to monitor one or more physiological parameters of the patient. As shown, the sensors may be coupled to the medical device controller 120 via a wired or wireless connection. The sensors can include one or more electrocardiogram (ECG) electrodes 222 (e.g., similar to sensing electrodes 112 as described above in connection with FIG. 1), bio-vibration sensors 224, tissue fluid monitors 226 (e.g., based on ultra-wide band radio frequency devices), and a patient movement sensor 228.

The ECG electrodes 222 can monitor a patient's ECG information. For example, the ECG electrodes 222 can be galvanic (e.g., conductive) and/or capacitive electrodes configured to measure changes in a patient's electrophysiology to measure the patient's ECG information. The ECG electrodes 222 can transmit information descriptive of the ECG signals to the sensor interface 212 for subsequent analysis.

The bio-vibration sensors 224 can detect a patient's vibrations associated with, for example, heart and lung activity. For example, the bio-vibration sensors 224 can be configured to detect cardio or heart vibration values including any one or all of S1, S2, S3, and S4. From these heart vibration values, certain heart vibration metrics or combinational metrics may be calculated, including any one or more of electromechanical activation time (EMAT), left ventricular systolic time (LVST), or percentage of left ventricular systolic time (% LVST). The bio-vibration sensors 224 can include a vibration sensor configured to detect vibrations from a subject's cardiac system and provide an output signal responsive to the detected cardio-vibrations. The bio-vibration sensors 224 can also include a multi-channel accelerometer, for example, a three-channel accelerometer configured to sense movement in each of three orthogonal axes such that patient movement/body position can be detected and correlated to detected heart vibrations information. The bio-vibration sensors 224 can transmit information descriptive of the cardio-vibration information to the sensor interface 212 for subsequent analysis.

The tissue fluid monitors 226 can use radio frequency-based techniques to assess fluid levels and accumulation in a patient's body tissue. For example, the tissue fluid monitors 226 can be configured to measure fluid content in the lungs, typically for diagnosis and follow-up of pulmonary edema or lung congestion in heart failure patients. The tissue fluid monitors 226 can include one or more antennas configured to direct radio frequency waves through a patient's tissue and measure output radio frequency signals in response to the waves that have passed through the tissue. In certain implementations, the output radio frequency signals include parameters indicative of a fluid level in the patient's tissue. The tissue fluid monitors 226 can transmit information descriptive of the tissue fluid levels to the sensor interface 212 for subsequent analysis. Examples of radio frequency sensors are further described in FIGS. 4A and 4B below.

The patient movement sensor 228 can include one or more accelerometers configured to measure motion data related to patient movement. In certain implementations, the patient movement sensor 228 can be configured to measure the number of steps a patient takes over a particular amount of time. For example, a patient may be instructed to perform a particular exercise such as a walk test. The patient movement sensor 228 can be configured to measure step and pace information during the particular exercise. It should be noted, however, that the patient movement sensor 228 is shown as a separate component by way of example only. In certain implementations, the one or more accelerometers included in the patient movement sensor 228 may be integrated into other components such as the bio-vibration sensors 224 or the tissue fluid monitors 226.

The sensor interface 212 can be coupled to any one or combination of sensing electrodes/other sensors to receive other patient data indicative of patient parameters. Once data from the sensors has been received by the sensor interface 212, the data can be directed by the processor 218 to an appropriate component within the medical device controller 120. For example, if heart data is collected by bio-vibration sensor 224 and transmitted to the sensor interface 212, the sensor interface 212 can transmit the data to the processor 218 which, in turn, relays the data to a cardiac event detector. The cardiac event data can also be stored on the data storage 204.

In certain implementations, the alarm manager 214 can be configured to manage alarm profiles and notify one or more intended recipients of events specified within the alarm profiles as being of interest to the intended recipients. These intended recipients can include external entities such as users (patients, physicians, and monitoring personnel) as well as computer systems (monitoring systems or emergency response systems). The alarm manager 214 can be implemented using hardware or a combination of hardware and software. For instance, in some examples, the alarm manager 214 can be implemented as a software component that is stored within the data storage 204 and executed by the processor 218. In this example, the instructions included in the alarm manager 214 can cause the processor 218 to configure alarm profiles and notify intended recipients using the alarm profiles. In other examples, alarm manager 214 can be an application-specific integrated circuit (ASIC) that is coupled to the processor 218 and configured to manage alarm profiles and notify intended recipients using alarms specified within the alarm profiles. Thus, examples of alarm manager 214 are not limited to a particular hardware or software implementation.

In some implementations, the processor 218 includes one or more processors (or one or more processor cores) that each are configured to perform a series of instructions that result in manipulated data and/or control the operation of the other components of the medical device controller 120. In some implementations, when executing a specific process (e.g., cardiac monitoring), the processor 218 can be configured to make specific logic-based determinations based on input data received, and be further configured to provide one or more outputs that can be used to control or otherwise inform subsequent processing to be carried out by the processor 218 and/or other processors or circuitry with which processor 218 is communicatively coupled. Thus, the processor 218 reacts to specific input stimulus in a specific way and generates a corresponding output based on that input stimulus. In some example cases, the processor 218 can proceed through a sequence of logical transitions in which various internal register states and/or other bit cell states internal or external to the processor 218 may be set to logic high or logic low. As referred to herein, the processor 218 can be configured to execute a function where software is stored in a data store coupled to the processor 218, the software being configured to cause the processor 218 to proceed through a sequence of various logic decisions that result in the function being executed. The various components that are described herein as being executable by the processor 218 can be implemented in various forms of specialized hardware, software, or a combination thereof. For example, the processor can be a digital signal processor (DSP) such as a 24-bit DSP processor. The processor can be a multi-core processor, e.g., having two or more processing cores. The processor can be an Advanced RISC Machine (ARM) processor such as a 32-bit ARM processor or a 64-bit ARM processor. The processor can execute an embedded operating system, and include services provided by the operating system that can be used for file system manipulation, display & audio generation, basic networking, firewalling, data encryption and communications.

Figure 3:
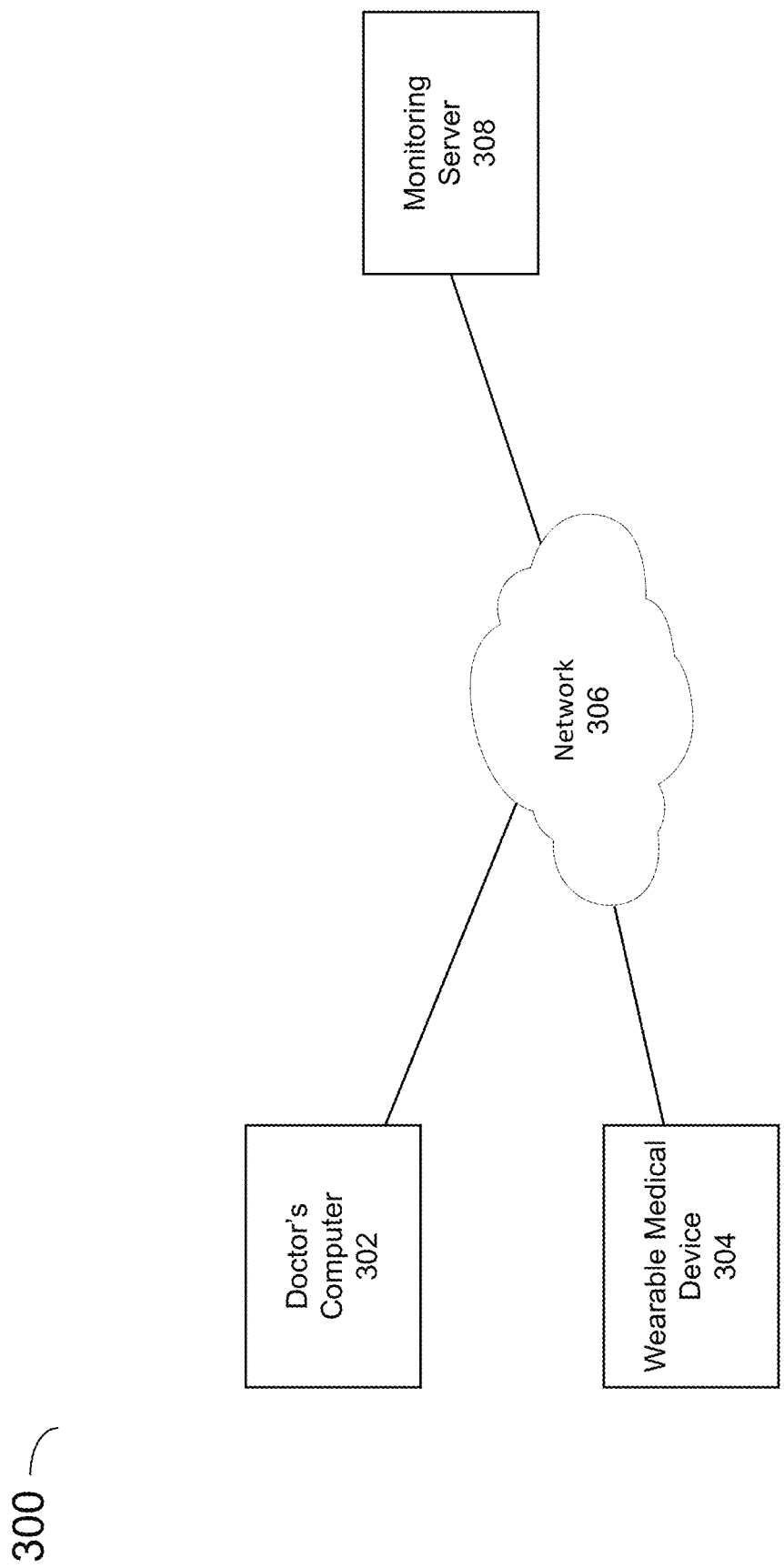
FIG. 3 depicts a sample network overview, in accordance with an example of the present disclosure.

FIG. 3 illustrates a sample network 300 depicting a sample topology illustrating how a wearable medical device (e.g., medical device 100 as described above) can be operably connected to a remote server. As described above in connection with FIG. 2, the wearable medical device controller 120 includes a network interface 206 for transmitting data over a wireless link such as a Bluetooth® wireless link (e.g., via a "hotspot" or other base station or intermediate device), a broadband cellular link, or a Wi-Fi™ communications link based on the IEEE 802.11 standard. As shown in FIG. 3, a doctor's computer 302 and a wearable medical device 304 can be operably connected to a monitoring server 308 through network 306. In certain implementations, while being worn, the wearable medical device 304 can be collecting information related to the patient such as various patient metrics and parameters as described herein. Depending upon the connection to network 306, and the programming of wearable medical device 304, the wearable medical device can be configured to regularly transmit the collected information to the monitoring server 308 for further processing. For example, the monitoring server 308 can be configured to monitor the physiological status of patients based on patient data obtained from multiple sensor sources including bio-vibrational sensors and radio frequency sensors and transmitted to the monitoring server by, for example, one or more wearable medical devices 304. In some example, one or more physicians can access the patient status information using the doctor's computer 302 to review changes in patient condition, receive instruction/recommendation to change a patient's treatment regimen, and to perform other similar functions.

In some examples, as noted above, a patient may wear a radio frequency device, e.g., a radio frequency transceiver such as an ultra-wide band transceiver circuit that is configured to direct radio frequency electromagnetic energy into the patient via radio frequency antennas and produce radio frequency information responsive to reflected electromagnetic energy. In certain implementations, the radio frequency device (transceiver and associated antennas) can be integrated into a patch worn by the patient in addition to a wearable medical device as described above. For example, as shown in FIG. 4A, a patch 402 may be adhesively affixed to a patient 400 at a prescribed location on the patient's body.

In other implementations, the radio frequency device can be integrated into a garment of the wearable cardioverter defibrillator. In some implementations, the radio frequency device can be integrated into the wearable continuous event monitoring device. In some implementations, the radio frequency device can be integrated into one or more therapy electrodes and/or patches of the hospital wearable defibrillators. In the above implementations, the radio frequency device (e.g., integrated into patch 402) can be located over a lower left abdomen region of the patient 400 as shown in FIG. 4A and configured to direct the radio frequency electromagnetic energy into the thoracic cavity, e.g., towards the lungs and/or the heart of the patient. In other examples, the radio frequency device can be placed over at least one main artery such as the radial artery, the brachial artery, the aorta, and one or more pulmonary arteries, e.g., to monitor an arterial pulse of the patient. Information regarding the arterial pulse can be used to monitor a blood pressure measurement of the patient in accordance with implementations described below.

The radio frequency information responsive to reflected electromagnetic energy from the patient's thoracic cavity can be indicative of lung fluid levels (absolute values and changes in levels), thoracic impedance, blood pressure measurements, heart rate measurements, and/or certain cardiac conditions based on monitoring the patient's heart wall movements. Examples of radio frequency transceivers are described in, for example, U.S. Pat. No. 8,989,837 entitled "Methods and Systems for Determining Fluid Content of Tissue," U.S. Pat. No. 7,122,012 entitled "Detection of Fluids in Tissues," U.S. Patent Application Publication No. 2010/0256462 entitled "Method and System for Monitoring Thoracic Tissue Fluid," U.S. Pat. No. 9,675,251 entitled "Electromagnetic Probes, Methods for Fabricating Thereof, and Systems Which Use Such Electromagnetic Probes," U.S. Pat. No. 7,725,150 entitled "System and Method for Extracting Physiological Data Using Ultra-Wideband Radar and Improved Signal Processing Techniques," and U.S. Pat. No. 9,002,427 entitled "Apparatus and Method for Continuous Noninvasive Measurement of Respiratory Function and Events," the contents of which are incorporated herein by reference. As noted above, the radio frequency information responsive to reflected electromagnetic energy from the patient's thoracic cavity can be indicative of the patient's thoracic impedance values changes in the same.

Figure 4A:
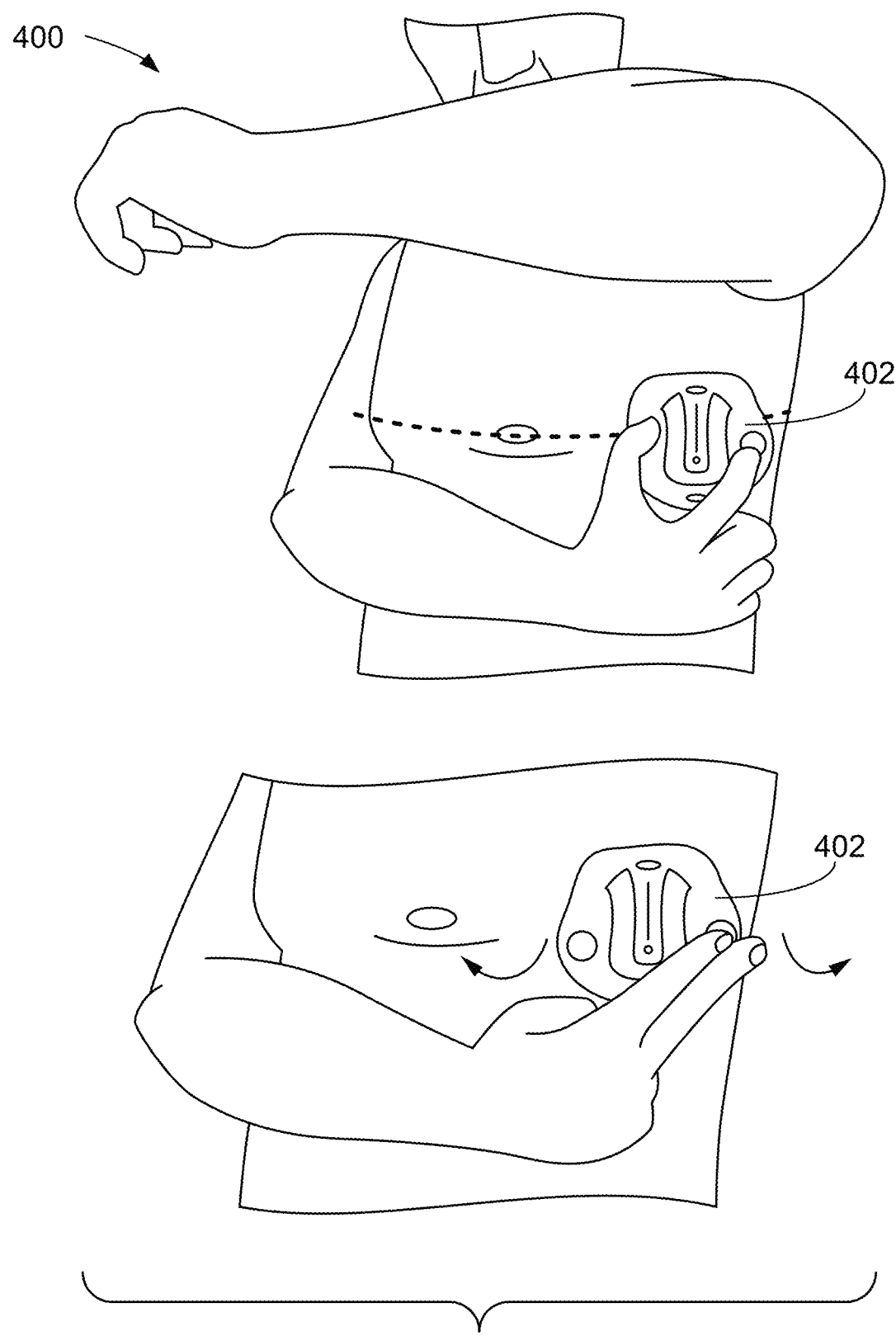
FIG. 4A depicts a sample radio frequency path unit affixed to a patient, in accordance with an example of the present disclosure.
Figure 4B:
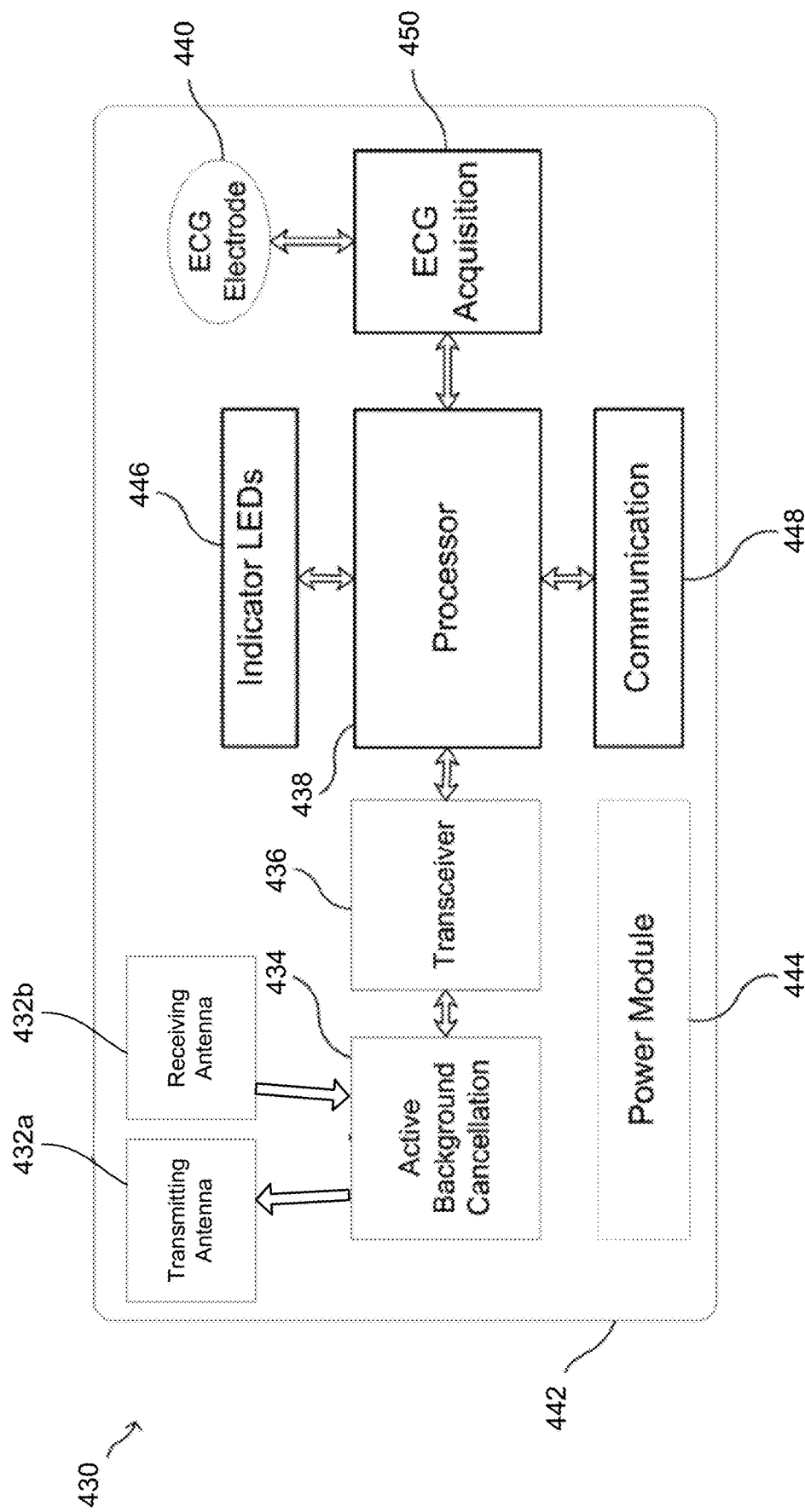
FIG. 4B depicts a schematic view of a radio frequency patch antenna unit, in accordance with an example of the present disclosure.

FIG. 4B illustrates a schematic of an example radio frequency device 430 such as the radio frequency device shown in FIG. 4A. The radio frequency device 430 can be configured to function as a radio frequency transceiver using components that are contained inside an integrated package 442 having, for example, the form of a patch or integrated into a wearable medical device as described above. In some implementations, the radio frequency device 430 can be implemented within a package 442 that has a form factor of about 20×50 mm. In other examples, the form factor may be smaller, e.g., in a range of around 10×25 mm to around 20×50 mm. In some examples, the package 442 can include an adhesive layer, for example, by means of which radio frequency device 430 can be affixed to the patient's skin.

Radio frequency device 430 includes at least two antennas, a transmitting antenna 432a and a receiving antenna 432b for transmitting and receiving the radio frequency energy into and from the thoracic cavity of the patient. The antennas 432a-b may, in some implementations, have a flat and/or flexible profile to better conform to the shape and contours of the patient's body. A transceiver 436 is configured to generate driving signals for transmission and/or reception of the radio frequency energy by the antennas 432a-b. The transceiver 436 is also configured to receive and process the reflected electromagnetic energy that receiving antenna 432b receives from the patient's body. In certain implementations, an active background cancellation circuit 434 cancels background components from the reflected signals, e.g., signals from depths and/or tissues that are not of interest. A processor 438 controls the operation of the components of radio frequency device 430 as described below. The processor 438 can monitor one or more radio frequency signal path characteristics and produce radio frequency information corresponding to a selected tissue depth (e.g., in a range of between 1 to 20 cm) and/or tissue of interest, such as an effective path length of the radio frequency wave path, and one or more phase and/or amplitude changes of the reflected radio frequency waves relative to the transmitted radio frequency waves. The processor 438 can process this radio frequency information and transform such information into interpretable physiological metrics such as thoracic fluid content information (TFC), heart wall motion data, and/or arterial pulse information. In some implementations, the radio frequency device 430 may be configured to transmit the radio frequency information via communications interface 448 to a remote server. In such implementations, the remote server can be configured to process the received radio frequency information and perform the transformation into the physiological metrics noted above. A power module 444, such as a low-profile battery, provides power to the components of the patch unit.

In some implementations, the radio frequency device 430 can also include an ECG electrode 440, in electrical contact with the patient's skin, and an ECG acquisition circuit 450, which filters and digitizes the ECG signals for input to processor 438. The ECG signal can be used to gate the transmission and reception of the radio frequency waves into and from the thoracic cavity of the patient. For example, the transceiver 436 may trigger radio frequency transmissions based on the timing of the R waves of the ECG signal.

In certain implementations, the radio frequency device 430 includes a user interface, such as one or more indicator LEDs 446, which signal the operational state of the patch (on/off, and possibly parameters such as battery level, quality of skin contact or signal strength). Alternatively or additionally, the user interface can include a more informative display, such as a LCD, as well as user controls, such as on/off and adjustment buttons.

A communication interface 448 communicates with a remote console, in order to transmit radio frequency and ECG measurement data and, in some instances, receive operational commands. For example, the communication interface 448 can typically include a wireless link, such as a Bluetooth™ or a WiFi link. For example, the remote console can be located in proximity to the patient's location and can thus receive and process the data from communication interface 448 directly. Alternatively, communication interface 448 can communicate with a local gateway, such as a personal computer, a smart phone device, or a dedicated "hotspot" device, which communicates with the remote server over a network, such as the Internet or a telephone network. In these implementations, the console may be a networked server that is connected to one or more databases and configured to store the radio frequency and ECG data for subsequent viewing, processing, and analysis. For example, a physician or other expert may be provided access and/or tools to perform analysis on the data. In some situations, the data may be made available via a wired or wireless communication link to another diagnostic computer system. These system configurations are particularly useful for extended ambulatory monitoring of multiple patients at various geographical locations.

As noted above, a radio frequency device such as device 430 can be used to monitor various metrics and parameters for a patient. For example, a radio frequency device can be configured to monitor tissue fluid metrics, blood pressure, chest wall movements, and other similar patient parameters.

To measure tissue fluid metrics, a radio frequency device can be configured to direct electromagnetic energy into an area of tissue (e.g., the lungs or thoracic cavity) and measure the amplitude and delay of returned/reflected electromagnetic energy. For example, FIG. 5A illustrates a schematic plot 500 showing amplitude and FIG. 5B illustrates a schematic plot 505 showing propagation delay of radio frequency waves reflected from a patient's heart. It should be noted that, as shown in FIGS. 5A and 5B, the scales of plots 500 and 505 are arbitrary. The delay and, to a lesser extent, the amplitude vary periodically with the heart cycle, as shown particularly by the sharp peaks of line 507 as shown in FIG. 5B and the general shift downward in amplitude in line 502 shown in FIG. 5A.

The depressed portions of both line 502 and 507 between about marks 250 and 260 on the horizontal scale correspond to a period of inhalation during the respiratory cycle. This depression in FIG. 5B shows that when the lungs are full of air, the effective radio frequency path length through the lung decreases, since the physical distance between the antenna and the heart remains about the same, while the average dielectric constant along the path decreases. Exhalation empties the lungs of air and thus increases the effective radio frequency path length. The amplitude of the reflected wave in FIG. 5A also drops during inhalation, presumably because of increased variations of the dielectric constant, and hence more reflections, along the radio frequency path through the lung when the lung is filled with air.

For a lung with a high fluid content, the average dielectric constant will typically be higher than a healthy lung, and the path delay of radio frequency waves traversing the lung will therefore be greater. The overall amplitude may also be greater due to reduced reflections as the waves traverse the lungs. On the other hand, the difference between air-filled and empty lungs over the respiratory cycle is expected to be smaller in both amplitude and delay than the differences shown in FIGS. 5A and 5B. Thus, to monitor tissue fluid content, a processing device can, for example, compare the delay and possibly the amplitude of the reflected waves to benchmarks provided by healthy and unhealthy lungs, or to previous measurements made on the same patient. Additionally or alternatively, the processing device can assess the amount of fluid in the lungs by analyzing the changes in delay and/or amplitude of the reflected waves over the course of one or more respiratory cycles. In certain implementations, order to quantify the assessment of fluid accumulation, the actual physical distance traversed by the radio frequency waves passing through the lung may be measured, and a relation (such as a ratio) may be computed between the effective radio frequency path length and the physical distance.

Figure 6:
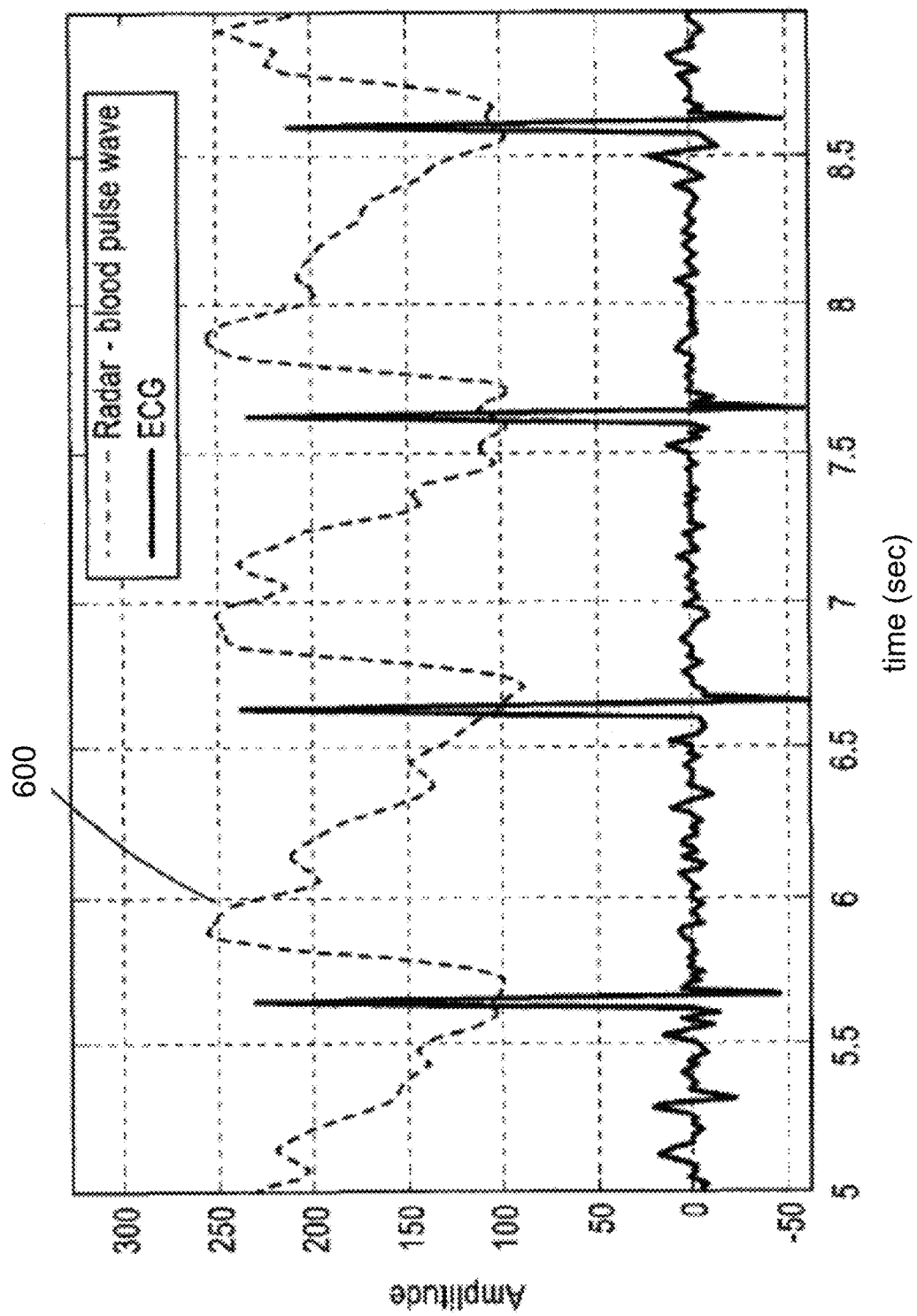
FIG. 6 depicts an example arterial pulse waveform, in accordance with an example of the present disclosure.

Additionally, a radio frequency device can be used to measure a patient's blood pressure. For example, information determined from a patient's arterial pulse waveform can be used by a processing device to determine a patient's blood pressure. As shown in FIG. 6, an arterial pulse waveform 600 can be obtained for a patient by directing a radio frequency wave into a patient's artery and measuring the reflected radio frequency waves. Based upon the reflected waves, a processing device can measure changes in a radar cross section (RCS) of the artery.

For example, during a cardiac cycle, a radio frequency device can generate and transmit radio frequency waves towards an artery which may be located at a certain depth from the radio frequency device. In some examples, some or all of the transmitted radio frequency waves may be reflected back to the radio frequency device. In some instances, the radio frequency device can transmit the radio frequency waves continuously or non-continuously. During the cardiac cycle, the diameter of the artery may vary over time and the RCS of the artery obtained by the radio frequency devices can change over time as well. From the measurements of the varying RCS, in some implementations, an arterial pulse waveform (e.g., pulse waveform 600) representing the pulse wave propagating through the artery may be determined. In turn, from the arterial pulse waveform, a variety of clinical information such as but not limited to arterial stiffness, pulse wave velocity, cardiac output, blood pressure measurements (continuous or non-continuous) can be obtained. In some embodiments, the reflected echo may be modulated by the artery over the course of the cardiac cycle, and information from the reflected echo can be used to determine/estimate the arterial pulse waveform. For example, the measurement range can change over the course of the cardiac cycle, leading to changes in the phase of the reflected waves. In such instances, such information can be utilized to determine/estimate the arterial pulse waveform.

In certain implementations, to more accurately determine a patient's blood pressure, the radio frequency device can be calibrated to include base measurements of the patient's blood pressure and pulse travel time (PTT). The PTT can be obtained by using multiple sensors affixed at known positions on the patient and measuring the pulse arrival times (PAT) at each location. By calculating the differences in PAT for each location, and knowing the distance between the sensors, a processing device can calculate the PTT. This information can also be used to determine a patient's pulse wave velocity (PWV).

In certain implementations, linear transformations relating the systolic blood pressure (SBP) and diastolic blood pressure (DBP) to the PTT may be expressed as follows:

$$SBP=(a\times PTT)+b,$$

$$DBP=(c\times PTT)+d$$

where the coefficients a, b, c and d can be calibrated for each patient. In some embodiments, other types of transformations may be used to calculate blood pressures. For example, for a model that assumes constant artery thickness and radius, blood pressure P may be expressed as $P=a\times \ln(PTT)+b$, where, again a and b are constants to be calibrated for each patient. In any case, in some embodiments, obtaining PTT, or conversely PWV of a pulse in an artery, can be used for the determination of blood pressure levels in the artery. Additional examples related to determining blood pressure using a radio frequency device are described in, for example, U.S. Patent Application Publication No. 2016/0345845 entitled "Systems, Apparatuses and Methods for Determining Blood Pressure," the content of which is incorporated herein by reference.

From the information related to the collected parameters and metrics as described above, (e.g., tissue fluid levels and blood pressure), additional metrics can be determined. For example, by extracting breathing information from the fluid measurement information, a processing device can determine information such as chest wall movement and rate of breathing. For example, the processing device can be configured to associate chest wall expansion with a time period where the patient is inhaling and associate chest wall contraction with a time period where the patient is exhaling.

Heart vibrations are the noises generated by the beating heart and the resultant flow of blood through it. Specifically, the vibrations reflect the turbulence created when the heart valves snap shut. In cardiac monitoring, for example, one or more heart vibrations sensors can be used to detect these unique and distinct vibrations that provide important auditory data regarding the condition of the heart.

In healthy adults, there are at least two normal heart vibrations often described as a lub and a dub (or dup), that occur in sequence with each heartbeat. For example, a first heart vibration (S1) and a second heart vibration (S2) are produced by the closing of the atrioventricular valves (AV valves) and semilunar valves (SL valves), respectively. More specifically, the S1 vibration represents the closing of the AV valves including the tricuspid valve positioned between the right atria and right ventricle, and the mitral valve located between the left atria and left ventricle. The S2 vibration represents the closing of the SL valves including the pulmonic valve that ejects blood to the lungs to get oxygen and is positioned between the right ventricle and the pulmonary artery, and the aortic valve that ejects oxygenated blood to the body and is positioned between the left ventricle and the aorta.

Systole refers the part of the cardiac cycle when the ventricles contract. Diastole is the part of the cardiac cycle when the ventricles relax and refill with blood following systole. Similarly, atrial diastole is the period during which the atria are relaxing. During ventricular diastole, the pressure in the left and right ventricles drops from the peak that it reaches in systole (e.g., 120 mmHg in a normal heart). When the pressure in the left ventricle drops to below the pressure in the left atrium, the mitral valve opens, causing accumulated blood from the atrium to flow into the ventricle.

When the smaller, upper atria chambers contract in late diastole, they send blood down to the larger, lower ventricle chambers. When the lower chambers are filled and the valves to the atria are closed, the ventricles undergo isovolumetric contraction (contraction of the ventricles while all valves are closed), marking the first stage of systole. The second phase of systole sends blood from the left ventricle to the aorta and body extremities, and from the right ventricle to the lungs. Thus, the atria and ventricles contract in alternating sequence. The left and right atria feed blood at the same time into the ventricles. Then, the left and right ventricles contract simultaneously as well.

The following TABLE 1 represents a summary of the cardiac cycle:

TABLE 1

| | AV valves | Semilunar valves | Status of ventricles and atria |
|---|---|---|---|
| 1. Atrial Systole | open | closed | Atria contract and pump blood<br>Ventricles, already partially filled from phase 5 (see below), receive last ~30% of blood, for a final resting volume of approximately 130 mL. |
| 2. Isovolumetric Contraction | closed | closed | Ventricles begin to contract. Ventricular muscle initially shortens only a little, but intraventricular pressure rises sharply<br>Ventricular volume unchanged |
| 3. Ventricular Ejection | closed | open | Pressures in left and right Ventricle exceed pressures in Aorta (80 mmHg) and Pulmonary Artery (10 mmHg). Ejection is rapid at first, slowing down as systole progresses.<br>Amount ejected each ventricle per stroke at rest is 70-90 mL. Approximately 50 mL of blood remains in each ventricle at the end of systole |
| 4. Isovolumetric Relaxation | closed | closed | Valves close as Ventricles relax and pressure within Ventricles drops below 120 mmHg. This ends once Ventricular Pressure falls below Atrial pressure and AV valves open<br>pump blood to rest of body |

TABLE 1-continued

| | AV valves | Semilunar valves | Status of ventricles and atria |
|---|---|---|---|
| 5. Ventricular Filling | open | closed | ventricles relaxed<br>ventricles passively fill with approximately 70% of their final volume. As the ventricles fill, rate of filling decreases and the AV valves drift towards closing<br>atria expand and are filling |

In addition to S1 and S2 vibrations, S3 and S4 vibrations may be picked up by sensitive sensors such as vibrational sensors. Typically, an examining physician performing cardiac auscultation (e.g., listening to the internal heart vibrations using a stethoscope) would not hear S3 vibrations in healthy adults.

The third heart vibration S3 is a vibration that occurs soon after the normal two "lub-dub" heart vibrations (i.e., S1 and S2). The S3 vibration typically occurs at the beginning of the middle third of diastole, approximately 0.12 to 0.18 seconds after S2. This produces a rhythm classically compared to the cadence of the word "Kentucky" with the final syllable representing the S3 vibration. The S3 vibration is lower in pitch than the S1 or S2 vibrations as it is not of valvular origin. The S3 vibration is usually benign in youth, some trained athletes, and sometimes in pregnancy, but if it re-emerges later in life it may signal cardiac problems, such as a failing left ventricle as in dilated congestive heart failure (CIF). The S3 vibration is thought to be caused by the oscillation of blood back and forth between the walls of the ventricles initiated by blood rushing in from the atria. The reason the third heart vibration does not occur until the middle third of diastole is likely that, during the early part of diastole, the ventricles are not filled sufficiently to create enough tension for reverberation. Typically, in a stethoscope mediated examination, S3 is associated with heart failure because the fact that it can be picked up via this method means that the ventricles are stiffer than that of a normal heart where the vibration of the blood hitting the walls of the ventricles is audible.

The strength of the third heart vibration (S3 strength) is based on the intensity and persistence of that vibration. For example, a sensitive vibrational sensor configured to detect the S3 vibration can provide a value of the S3 vibration strength in the range of 0 to 10. In some implementations, if this strength value equals or exceeds 5.0, a reporting process can declare that an S3 is present.

The fourth heart vibration S4 is produced by the vibration of blood being forced into a stiff or hypertrophic ventricle. If heard in a stethoscope exam, the S4 vibration is a sign of a pathologic state, usually a failing or hypertrophic left ventricle, as in systemic hypertension, severe valvular aortic stenosis, and hypertrophic cardiomyopathy. The vibration occurs just after atrial contraction at the end of diastole and immediately before the S1 vibration, producing a rhythm sometimes referred to as the "Tennessee" gallop.

As noted above, a wearable medical device can be configured to monitor other physiologic parameters of the patient in addition to cardiac related parameters. In certain implementations, the wearable medical device can be configured to monitor, for example, using vibrational sensors such as microphones and/or accelerometers positioned over the patient's thoracic area. In some implementations, the vibrational sensor can be configured to detect heart vibrations (S1, S2, S3, and S4 vibrations, murmurs), lung vibrations, breathing/chest wall movements, sleep related parameters (e.g., snoring, sleep apnea), and other similar vibration-based parameters.

Figure 7:
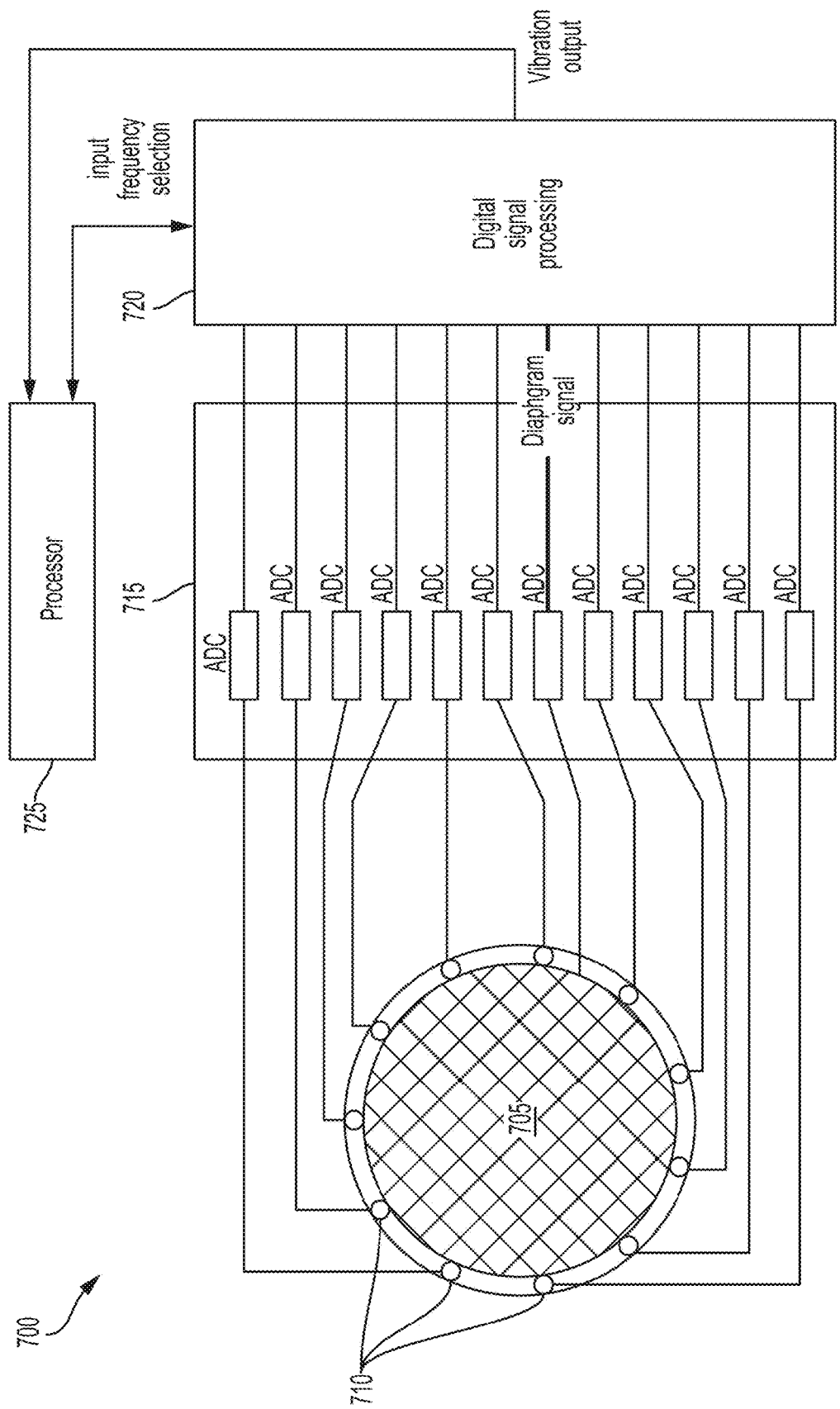
FIG. 7 depicts a schematic view of a vibrational sensor, in accordance with an example of the present disclosure.

FIG. 7 illustrates a sample schematic including a vibrational sensor 700. In an implementation, the vibrational sensor 700 can include a high-fidelity diaphragm 705, e.g., a dynamic, electret condenser, ribbon based or a piezoelectric crystal-based diaphragm. Separately, a plurality of motion sensors 710 (e.g., at least two, four, six, or more) can be located around a periphery of the diaphragm 705. The vibrational signals from the diaphragm 705 and the plurality of motion sensors 710 can be digitized by a series of analog to digital converters (ADC) 715 and processed through a digital signal processing unit 720. For example, the digital signal processing unit can include a series of digital filters.

For example, the motion sensors 710 can include multi-axial accelerometers that produce digitized signals that are input to the digital signal processing unit 720 along with the digitized diaphragm signal.

The signals from one or more of the plurality of motion sensors 710 can be used to monitor low frequency vibrations. For example, such low frequency vibrations comprise breathing and/or chest wall movement.

When monitoring higher frequency range vibrational signals (e.g., certain lung vibrations, heart murmurs, etc.) the diaphragm signal can be analyzed as outlined below. To allow for better isolation of the higher frequencies of interest, the signals from the peripheral motion sensors 710 can be summed to determine a common mode signal. The common mode signal can represent lower frequency components that can then be removed from the diaphragm signal.

A table such as table 2 shown below may be stored in a memory of the sensor 700. Typical sampling rates in a range of 44.1 Khz to around 60 KHz can be implemented in the ADC to transform the acquired diaphragm vibrational signals into digital vibration signals. In some examples, the ADCs 715 may implement sample sizes in a range from 12-bits to 16-bits, with higher bit lengths to allow for more dynamic range resolution. A variety of digital filters can be run on the input digital signal to remove, for example, interference signals such as 60 Hz components and common mode rejection signals as described above. The digitized vibrational signals can then be analyzed to determine various vibrations based on the table. For example, frequency selection filters and circuits can operate in the digital domain to isolate frequency ranges of interest in accordance with the table below. Example digital filtering techniques can include Fast Fourier Transform (FFT), Discrete Cosine Transform (DCT), Infinite impulse response (IIR) filters, among others. A processor can be configured to receive instructions indicating a type of condition to be monitored. Based on the indicated condition, a processor 725 can retrieve a relevant range of frequencies from memory and instruct the digital signal processing unit 720 to isolate the relevant signals for analysis and input into the next stage.

TABLE 2

| Condition being monitored | Digital filter range |
|---|---|
| Breathing/chest wall movement | 0.1-10 Hz |
| Stridor | >500 Hz |
| Wheezing | >100-5000 Hz |
| Rhonchus | 100-200 Hz |
| Pleural friction | <350 Hz |
| S1-S4 heart vibrations | 20-500 Hz |
| Diastolic murmur | 50-150 Hz |
| Aortic regurgitation | 200-600 Hz |

In certain implementations, a vibrational analysis of vibrations detected via a thoracic vibrations sensor such as sensor 700 described above can provide information about characteristic vibrational patterns. The vibrational analysis can include monitoring for vibrations ranging from 1/10th to about 1 Hz for monitoring low frequency thoracic cavity movements such as breathing, chest wall movements, and, in some cases, heart wall movements. For example, where the sensor is substantially aligned with an apex of a ventricle of the patient, the sensor implementing vibrational analysis can detect and monitor ventricular wall motion. Similarly, other vibrational patterns can be monitored.

In certain implementations, more than one frequency range of the pulmonary-vibrations may be monitored at a time. For example, an obstruction can produce a rocking chest motion such as paradoxical breathing. With inhalation, the diaphragm descends maximally, pushing the abdominal contents down and out and generating negative pressure. This negative pressure pulls the chest wall inward, resulting in the abdomen rising and the chest falling during inhalation—the opposite motion of normal breathing. During exhalation with paradoxical breathing, the chest rises and the abdomen falls. Again, this motion is the opposite motion of normal breathing. The more compliant or flexible the chest wall, as in young children, the easier the chest movements are to see. With paradoxical breathing, the lower jaw is also pulled backwards with each breath as the tongue is pulled down over the airway and breathing often becomes noisy. The patient may exhibit, for example, stridor, snoring, and/or grunting. Thus, stridor-related frequencies (>500 Hz) can be monitored with very low frequency vibrations (0.2 Hz) of the chest wall and/or abdomen that can be indicative of a paradoxical breathing motion.

Figure 8:
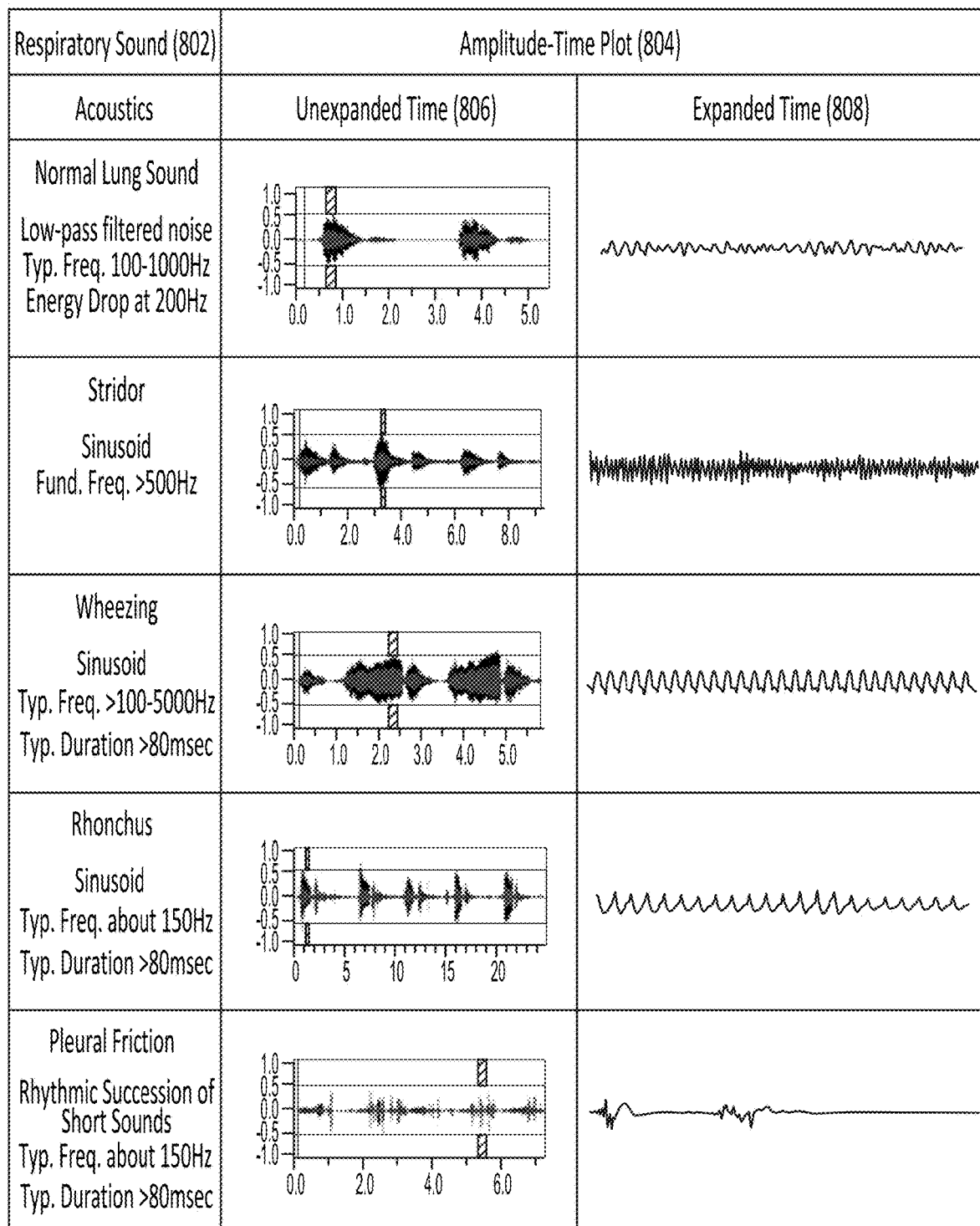
FIG. 8 depicts a chart of lung vibrations and associated time-amplitude plots.

For example, certain lung vibrations have characteristic patterns at various frequencies including at around 100-5000 Hz (e.g., tracheal vibrations), >500 Hz (e.g., stridor), >100-5000 Hz (e.g., wheezing), −150 Hz (e.g., rhonchus), and <350 Hz (e.g., pleural friction). FIG. 8 illustrates various characteristic patterns for certain lung vibrations. As shown in FIG. 8, a listing of respiratory sounds 802 can have one or more associated amplitude-time plots 804. Each respiratory sound 802 can include a unique set of acoustic characteristics. For example, as shown in FIG. 8, normal lung vibrations can be characterized as low-pass filtered noise having a typical frequency of 100-1000 Hz with a measured energy drop at 200 Hz. Various other lung vibrations such as stridor, wheezing, rhonchus, and pleural friction have similar characteristics as shown in FIG. 8. Similarly, each respiratory sound 802 can have an associated amplitude-time plot 804, shown in FIG. 8 as both an unexpanded time plot 806 and an expanded time plot 808. For example, as shown in FIG. 8, the expanded time plot 808 for a particular respiratory sound 802 can correspond to the portion on the unexpended time plot 806 indicated by the dashed box. Additional lung conditions such as crackle, squawk, glottal, pharyngeal vibrations, and other similar lung vibrations and their corresponding frequencies can be drawn from A. Bohadana, G. Izbicki, and S. Kraman, "Fundamentals of Lung Auscultation," New England Journal of Medicine (2014).

Frequencies involving heart vibrations and murmurs are typically in a range from around 20 to 500 Hz. Low frequency heart vibrations are those where the dominant frequencies are less than around 100 Hz, such as S3, S4, and diastolic murmur of mitral stenosis. Certain murmurs have higher frequency components such as aortic regurgitation, where dominant frequencies are around 400 Hz.

Analyzing Patient Metrics for Tracking Patient Condition

As noted above, in various scenarios relevant to this disclosure, a patient monitoring system can include sensors configured to collect patient physiological signals beyond ECG signals. For example, a vibrational sensor can be configured to collect bio-vibrational signals such as cardiac-vibrational signals and pulmonary-vibrational signals. Additionally, a radio frequency sensor such as an ultra-wide band transceiver circuit can be configured to collect information responsive to radio frequency electromagnetic energy reflected from within a patient's thoracic cavity and/or the heart. In implementations described herein, a processing device can further process the various collected signals and related information from the different underlying physiological sensors to produce one or more combinational physiological parameters, e.g., physiological parameters that are determined based upon two or more different underlying physiological sensors and related information. At least one of a predictive analysis (e.g., using a machine learning process or an artificial neural network) and a trends analysis (e.g., a correlation analysis) can be performed on the collected signals and received information as well as the combinational metrics to determine a current condition for the patient as well as one or more clinically actionable events.

More specifically, in certain implementations, a patient monitoring system can include an ECG sensor coupled to the patient and configured to detect one or more ECG signals of the patient, a vibrational sensor coupled to the patient and configured to detect one or more cardio-vibrational signals of the patient, a radio frequency ultra-wide band transceiver circuit comprising one or more radio frequency antennas and coupled to the patient and configured to cause the one or more radio frequency antennas to direct radio frequency electromagnetic energy into the patient's thoracic cavity and produce radio frequency information responsive to reflected radio frequency electromagnetic energy received through the one or more radio frequency antennas and reflected from within the patient's thoracic cavity, and one or more processors. The one or more processors can be configured to process the a) one or more ECG signals, the b) one or more cardio-vibrational signals, and c) the radio frequency information to generate a plurality of physiological parameters of the patient including one or more combinational physiological parameters. The one or more processors can be further configured to: perform at least one of a predictive analysis and a trend analysis of the plurality of physiological parameters including the combinational physiological parameters to determine a current clinical condition of the patient, wherein the trend analysis comprises determining a presence of a substantial relationship between changes in the plurality of the physiological parameters; compare the current clinical condition of the patient to predetermined clinically actionable criteria to determine one or more clinically actionable events; and cause an output device to provide an output relating to one or more clinically actionable events.

In another implementation, a patient monitoring system can include at least one vibrational sensor coupled to the patient and configured to detect one or more cardio-vibrational signals, at least one radio frequency ultra-wide band transceiver coupled to the patient, and one or more processors. The at least one radio frequency ultra-wide band transceiver can be configured to direct radio frequency electromagnetic waves through the patient's lungs and detect radio frequency information responsively to the radio frequency electromagnetic waves that have passed through the lungs. The one or more processors can be configured to process the detected one or more cardiac vibrational signals over a predetermined duration to determine at least one cardiac vibrational metric of the patient, process the patient's radio frequency information over a predetermined duration to determine at least one lung fluid metric of the patient, determine an output relating to one or more clinically actionable events based on the determined at least one cardiac vibrational metric and the determined at least one lung fluid metric, and cause an output device to provide the output.

In another implementation, a patient monitoring system can include an ECG sensor coupled to the patient and configured to detect one or more ECG signals of the patient, a vibrational sensor coupled to the patient and configured to detect one or more cardio-vibrational signals of the patient, a radio frequency ultra-wide band transceiver circuit comprising one or more radio frequency antennas and coupled to the patient, and one or more processors. The radio frequency ultra-wide band transceiver can be configured to cause the one or more radio frequency antennas to direct radio frequency electromagnetic energy into the patient's thoracic cavity and produce radio frequency information responsive to reflected radio frequency electromagnetic energy received through the one or more radio frequency antennas and reflected from within the patient's thoracic cavity. The one or more processors can be configured to process the one or more ECG signals, the one or more cardio-vibrational signals, and the radio frequency information to generate a plurality of physiological parameters of the patient including one or more combinational physiological parameters, perform a trends analysis of the plurality of physiological parameters including the combinational physiological parameters to produce a trends result, update a monitoring schedule for the patient based upon the trends result, determine a current clinical condition of the patient based upon the trends result, compare the current clinical condition of the patient to predetermined clinically actionable criteria to determine one or more clinically actionable events, and cause an output device to provide an output relating to the one or more clinically actionable events.

In another implementation, a patient monitoring system can include an ECG sensor coupled to the patient and configured to detect one or more ECG signals of the patient, a vibrational sensor coupled to the patient and configured to detect one or more cardio-vibrational signals of the patient, a radio frequency ultra-wide band transceiver circuit comprising one or more radio frequency antennas and positioned on the patient over at least one main artery, and one or more processors. The radio frequency ultra-wide transceiver circuit can be configured to cause the one or more radio frequency antennas to direct radio frequency electromagnetic energy into at least a portion of the patient and produce radio frequency information responsive to reflected radio frequency electromagnetic energy received through the one or more radio frequency antennas and reflected from within the at least a portion of the patient. The one or more processors can be configured to process the one or more ECG signals, the one or more cardio-vibrational signals, and the radio frequency information to generate a plurality of physiological parameters of the patient including one or more combinational physiological parameters, perform at least one of a predictive analysis and a correlation analysis of the plurality of physiological parameters including the combinational physiological parameters to determine a current clinical condition of the patient, compare the current clinical condition of the patient to predetermined clinically actionable criteria to determine one or more clinically actionable events, and cause an output device to provide an output relating to one or more clinically actionable events.

Figure 9:
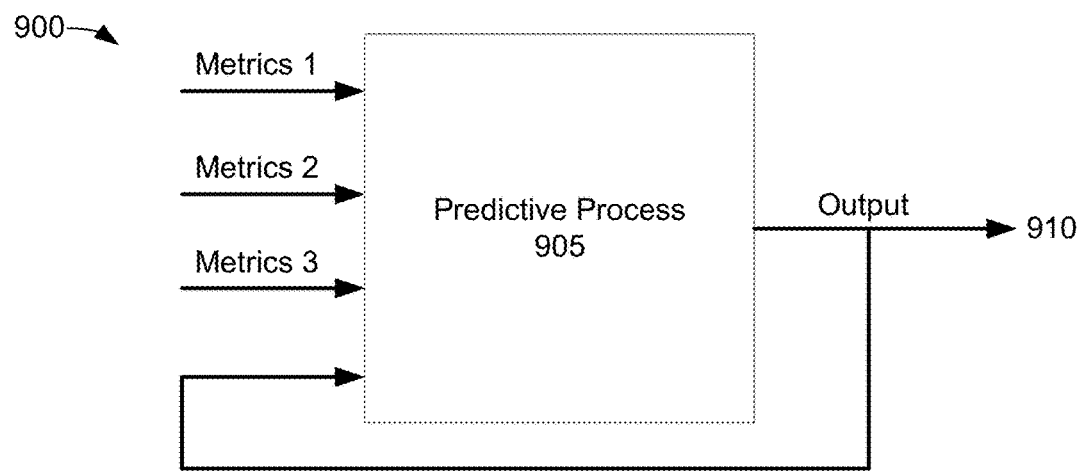
FIG. 9 depicts a sample overview of a process using a predictive analysis, in accordance with an example of the present disclosure.

As described herein, one or more processes can be used to provide for predictive and trends analysis for a patient. For example, a predictive analysis process can be created for a variety of different heart diseases that uses data from patient's medical devices including recorded ECG data, recorded vibrational data, and information related to radio frequency information collected for the patient. Predictive analytics can be used to determine a current condition for the patient and any clinically actionable events and likely outcomes for the patient. FIG. 9 illustrates a sample overview of a predictive analysis process. A set of metrics 900, including metrics 1, metrics 2, and metrics 3, can be provided to predictive process 905. Depending upon the design of the process and the expected output, various types of programming can be used for the predictive process 905. For example, the predictive process 905 can use machine learning and/or artificial neural networks, both of which are described in greater detail below. By processing the input metrics 900, the predictive process 905 can produce one or more outputs 910. For example, the output 910 can include a current condition of the patient, any likely adverse events that may occur in the near future for the patient (e.g., cardiac events that may occur in the next 30 days), and any clinically actionable events that should be taken by or with regard to the patient. In some implementations, the output 910 can be fed back into the predictive process so that the process learns from the outcomes and makes adjustments in its prediction scores based on changes in the patient's conditions.

Figure 10:
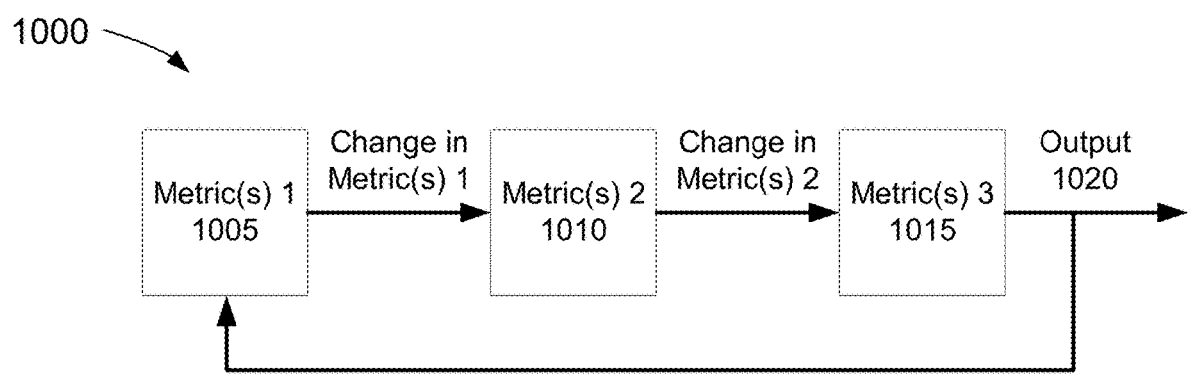
FIG. 10 depicts a sample overview of a process using a trends analysis, in accordance with an example of the present disclosure.

FIG. 10 illustrates a sample overview of a trends analysis process. The process 1000 can include monitoring a first metric(s) 1005. If a change is detected in the first metric 1005, or the first metric(s) exceeds a certain threshold, the process 1000 can trigger monitoring a second metric(s) 1010. Similarly, if a change is detected in the second metric(s) 1010, or the second metric(s) exceeds a certain threshold, the process 1000 can trigger monitoring a third metric(s) 1015. If the process 1000 detects a change in the third metric(s) 1015, the process can output 1020 an indication to, for example, the patient or the patient's physician. For example, the output can include recommended changes to a treatment regimen such as changes to a patient's medication. As shown, the output 1020 can be fed back into the trends analysis process to cause the process to adjust its response to the changes in the underlying metrics.

It should be noted that the overviews as shown in FIGS. 9 and 10 are shown by way of example only. For example, three metrics are shown in both overviews as examples of the number of metrics that can be used. In actual practice, various other numbers of input metrics can be used for both the predictive analysis and trends analysis processes.

In one implementation of the general schemes shown in FIGS. 9 and 10, metric(s) 1 is ECG metrics, metric(s) 2 is bio-vibrational metrics (including cardio-vibrational, lung-vibrational, and low frequency patient movement data), metric(s) 3 is radio frequency-based physiological metrics. Alternatively or in addition, one or more of metric(s) 1, 2, and 3 includes combinational metrics derived from one or more of the ECG metrics, bio-vibrational metrics, and radio frequency-based physiological metrics.

Figure 11:
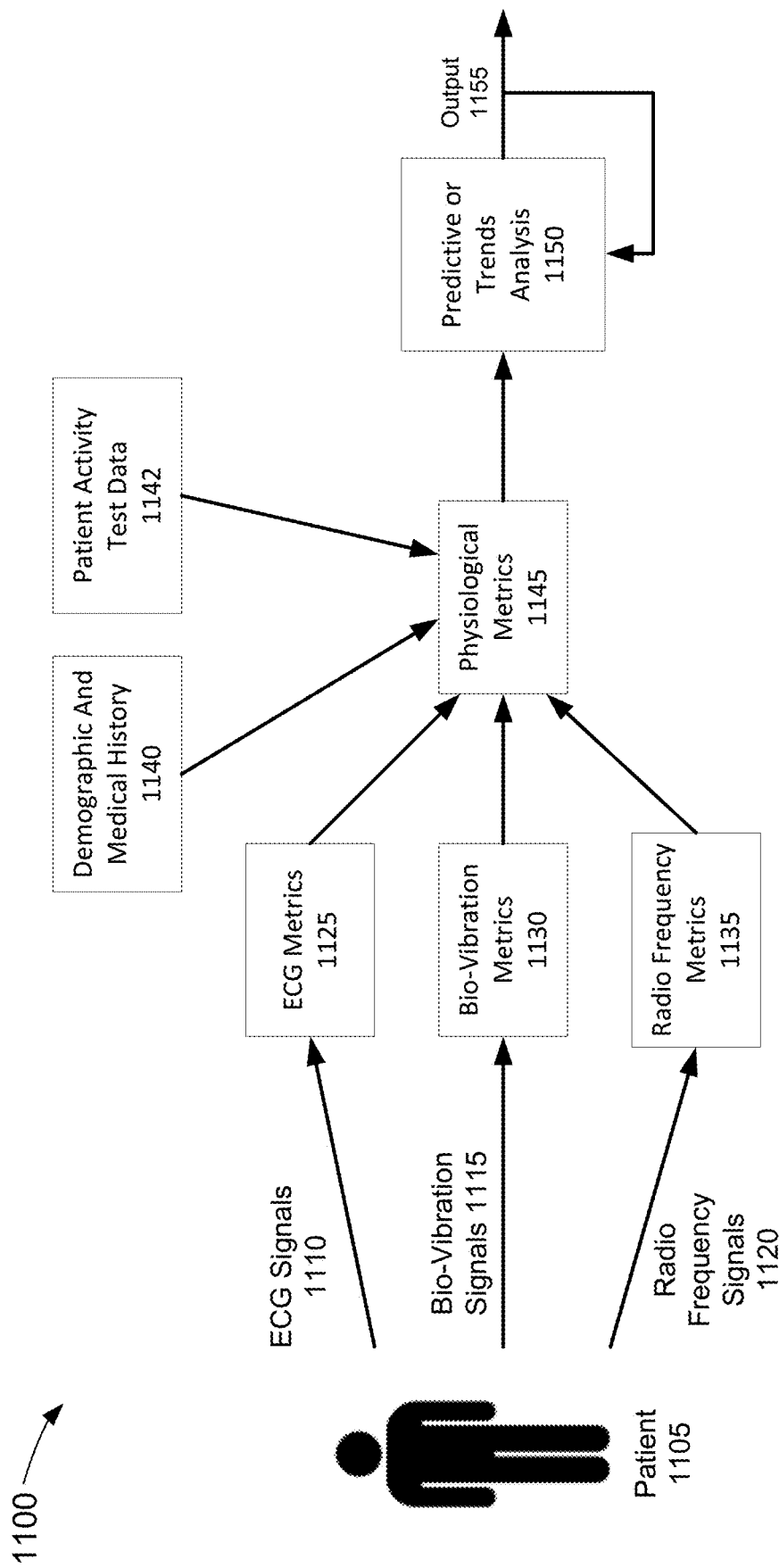
FIGS. 11 and 12 depict diagrams of a patient monitoring system, in accordance with an example of the present disclosure.
Figure 12:
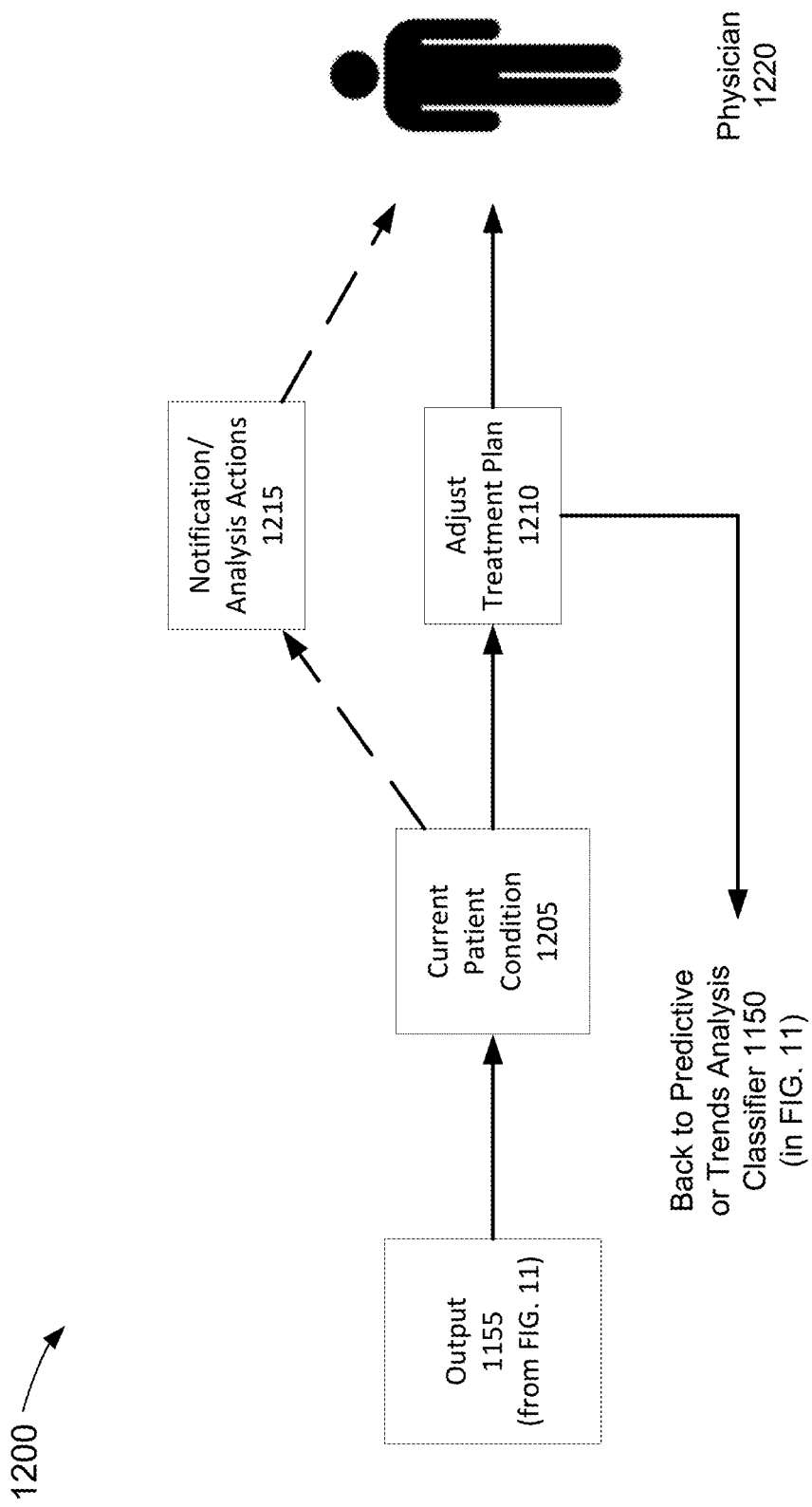

FIGS. 11 and 12 illustrate a patient monitoring system for indicating clinically actionable events based on a patient's changing physiological information. The system can determine, analyze and/or classify, and notify regarding clinically actionable events according to predetermined clinically actionable criteria.

As shown in FIG. 11, a system 1100 receives various signals from a patient 1105. For example, the system 1100 can receive the patient's ECG signals 1110, bio-vibrational signals 1115, and radio frequency signals 1120 from, for example, a wearable medical device coupled to the patient 1105. As shown, the output 1155 of the predictive or trends analysis classifier 1150 can be fed back in a closed loop manner to the predictive or trends analysis clsasifier 1150. For example, the monitoring may be initiated on just one set of physiological parameters, such as the ECG signals 1110. Over time or in response to certain conditions as described herein, additional sets of physiological parameters beyond ECG parameters, such as bio-vibrational signals 1115, or radio frequency-based signals 1120 (or combinational parameters thereof) may be initiated.

In certain implementations, the ECG signals 1110 can be processed and result in development of ECG based metrics 1125, such as but not limited to heart rate, heart rate variability, S-T segment elevation, premature ventricular contractions (PVC), heart rhythm morphology, and other similar ECG metrics. Specific details on the extraction of ECG based metrics 1125 are described in further detail below. Similarly, the bio-vibrational signals 1115 can be processed and result in the development of bio-vibrational metrics 1130, such as heart vibrations intensity values, lung and other pulmonary vibration intensity values, LVST values, and other similar bio-vibrational values. Additionally, the radio frequency signals 1120 can be processed and result in the development of radio frequency metrics 1135, such as thoracic fluid level values, heart wall movement metrics, and blood pressure. The metrics 1125, 1130, and 1135 can be combined into a single set of physiological metrics 1145.

Further, the above physiological metrics can be expanded to include combinational physiological metrics. For example, combinational physiological metrics can include metrics derived from two or more of metrics 1125, 1130, and/or 1135. One example of a combinational physiological metric is EMAT. EMAT represents a quantification of the time from an onset of a Q wave on an ECG signal to the closure of the mitral valve as determined form the S1 heart vibration. Typically, a prolonged EMAT value is associated with reduced left ventricle contractility. Another example of a combinational physiological metric is percent EMAT (% EMAT). % EMAT is computed as EMAT divided by the dominant RR interval in the ECG signal and represents the efficiency of the pumping function of the heart. A % EMAT of >15% can be highly predicative of re-hospitalization risk from heart failure at and post patient discharge. In an example, a cardio-acoustic vibrational parameter derived from the cardio or heart vibrational signals includes LVST. LVST can be calculated as an interval from S1 to S2 (S1-S2). A combinational metric based on the LVST and RR interval information from the patient's ECG signal can include % LVST. For example, % LVST can be calculated as a ratio of the interval from S1 to S2 with respect to an RR interval, e.g., (S1-S2/RR). Another example of a combinational physiological metric is ratio of EMAT/LVST, which is useful in determining an extent of left ventricle dysfunction. Another example of a combinational physiological metric is systolic dysfunction index (SDI). SDI is a multiplicative combination of ECG and vibrational parameters. SDI has been shown to predict left ventricle systolic dysfunction with high specificity. The multiplicative score SDI is derived from QRS duration, QR interval, % EMAT, and S3 vibration strength. SDI is reported as a value between 0 and 10. Other combination metrics can include % LVST, left ventricle end diastolic pressure (LVEDP), and other related combination metrics derived from two or more of the physiological metrics as described herein.

Referring again to FIG. 11, in some examples the physiological metrics 1145 can be extended with patient demographic and patient medical history information 1140. For example, patient demographic information can include age, gender, race, etc. For example, patient medical history information includes prior medical conditions, diagnoses, prior hospitalizations, etc. A sample patient history record may include information as indicated below and sample input to the patient monitoring system is also shown below in table 3.

TABLE 3

| Patient X: | Example input to patient monitoring processes |
|---|---|
| Patient is 57 years old, white, female, smoker Infectious Diseases: Usual childhood illnesses. No history of rheumatic fever. Immunizations: Flu vaccine yearly. Pneumovax 1996 Allergic to Penicillin-developed a diffuse rash after an injection 20 years ago. Transfusions: 4 units received in 1980 for GI hemorrhage, transfusion complicated by Hepatitis B infection. Hospitalizations: 1996 chest pain; patient was first admitted when she presented with a complaint of intermittent midsternal chest pain. ECG showed first degree | Age = 0.75 (0 = below 30, 0.5 = between 30-45; 0.75 = between 45 and 60; 0.9 = between 60 and 80; 1 = over 80) Prior_Heart_Failure_diagnosis = 1 (0 = No; 1 = Yes) Prior_Arrhythmia = 1 (0 = No; 1 = Yes) Prior_Diabetes = 0.75 (0 = No; 0.5 = Yes, under control and management; 0.75 = Yes, intervention needed to better control; 1 = Yes, no control) Smoker = 1 (0 = No; 1 = Yes) Prior_Heart_Related_Hospitalization = 1 (0 = No; 1 = Yes) Prior_MI_Condition = 0 (0 = No; 1 = Yes) Renal_assessment = 0.75 (range from 0 to 1; 0 = no prior renal disease; 1 = end stage renal disease - need to go or on |

TABLE 3-continued

| Patient X: | Example input to patient monitoring processes |
|---|---|
| atrioventricular block, and a chest X-ray showed mild pulmonary congestion, with cardiomegaly. Myocardial infarction was ruled out by the lack of electrocardiographic and cardiac enzyme abnormalities. Patient was discharged after a brief stay on a regimen of enalapril, and lasix, and digoxin, for presumed congestive heart failure. Since then she has been followed closely by her cardiologist. Operations: 1) Normal childbirth 15 years ago 2) 1989 Gastrointestinal hemorrhage 3) September 1995 chest pain- see history of present illness | dialysis) Hypercholesterolemia = 0.6 (range from 0 to 1; 0 = no high cholesterol detected in blood; 1 = extremely high levels of cholesterol detected) Blood pressure = 0.6 (range from 0 to 1; 0 = normal blood pressure, well within range; 0.5 = borderline blood pressure, under control; 0.6 = high blood pressure, under control by medication; 0.7 = high blood pressure, uncontrolled; 1 = dangerously high blood pressure) |

In some implementations, an additional set of physiological metrics may be derived based on patient activity test data 1142 from one or more physical activity tests performed by the patient while wearing the wearable medical device. For example, as shown below, the device may monitor one or more activity tests performed by the patient. In one example, the activity may be a physician ordered physical assessment such as a WalkTest™ activity assessment administered by the LifeVest® WCD. The purpose of the assessment is to monitor the patient's progress during the assessment by monitoring parameters such as a number of steps, distance traveled during the assessment, and a moving rate of the patient while the patient walks for about 6 minutes.

Before and after the walk, the patient can be asked to take a health survey, answering one or more questions relating to the patient's overall well-being. For example, the patient can be asked to indicate a level of shortness of breath (e.g., an example scale can be 0=feeling normal, 0.5=able to maintain a conversation while walking, 1=Needs to stop immediately). Another query may relate to the patient's fatigue level (e.g., how tired the patient feels). After the assessment, the patient may be prompted to answer the same set of questions again or additional questions. The responses to these questions can be normalized into a series of physiological parameters, e.g., stored as values ranging from 0 to 1, 0 to 10, 0 to 100, or any other suitable range, and input into the predictive and/or trends analysis. While numerical ranges are described herein, other scales, ranges, and/or methods of quantifying the patient's responses to the health survey can be used. The patient's physician prescriber may have the patient repeat the assessment once a day or once a week. The device can provide reminders to the patient via the user interface when the patient is next scheduled to take the assessment. While the health survey described herein is in the context of performing a physical assessment, in some implementations, the health survey can be administered to the patient wearing the device separately from the physical assessment. For instance, the device may prompt the patient to periodically (e.g., every day, week, or some other schedule) take the health survey. In some examples, the patient's physician may configure the device to administer a health survey as needed. In these cases, the patient's physician may instruct a technician to cause a remote server to send one or more operational commands to the wearable medical device to administer the health survey.

Distance walked over the assessment duration (e.g., 6 minutes) can be indicative of patient's current clinical state. For example, if patient walks less than a preset duration (such as 350 meters), the patient may be scored at having a relatively high risk of mortality relative to a patient that covers more than 350 meters. In some examples, the input into the predictive and/or trends analysis may be the raw distance covered by the patient. In other examples, the distance may be normalized in accordance to a predetermined scale. For example, a normalized scale may be generated representing the distance covered by the patient during the activity. For example, a scale from 0.0 to 1.0 representing distance covered is shown below in table 4:

TABLE 4

| Example assessment score | Example patient performance during assessment |
|---|---|
| 0 | Patient walked over 1000 meters during a six-minute walk test. |
| 0.25 | Patient walked between 600 and 999 meters during a six-minute walk test. |
| 0.5 | Patient walked between 350 and 599 meters during a six-minute walk test. |
| 0.75 | Patient walked between 100 and 349 meters during a six-minute walk test. |
| 1 | Patient walked less than 100 meters during a six-minute walk test |

In some examples, a clinician inputs a stride length into the device via a user interface potential variance in measuring distance when using clinician provided stride length. In some implementations, a standardized stride length (based on, for example, similar patient population data) can be implemented in calculating distance covered.

In addition or alternatively, the device may track a number of steps taken by the patient over the assessment duration (e.g., 6 minutes). Accelerometer data can be analyzed to count, e.g. heel strikes (as an example, this can be detected when a sum of the three axes of measurement of the accelerometer exceeds a preset threshold). For example, a scale from 0.0 to 1.0 representing steps taken is shown below in table 5:

TABLE 5

| Example assessment score | Example patient performance during assessment |
| --- | --- |
| 0 | Patient took over 500 steps during a six-minute walk test. |
| 0.25 | Patient took between 300 and 499 steps during a six-minute walk test. |
| 0.5 | Patient took between 175 and 299 steps during a six-minute walk test. |
| 0.75 | Patient took between 50 and 174 steps during a six-minute walk test. |
| 1 | Patient took less than 50 steps during a six-minute walk test. |

In some examples, the input into the predictive and/or trends analysis may be the raw number of steps taken by the patient. In other examples, the number of steps may be normalized in accordance to a predetermined scale.

Another parameter that can be tracked includes a pace during the assessment, for example, steps per minute and/or distance covered per minute. As before, in some examples, the input into the predictive and/or trends analysis may be the raw pace information of the patient. In other examples, the pace may be normalized in accordance to a predetermined scale. For example, during a normalization process, the metrics can be transformed and stored as values ranging from 0 to 1, 0 to 10, 0 to 100, or any other suitable range, and input into the predictive and/or trends analysis. While numerical ranges are described herein, other scales, ranges, and/or methods of quantifying the patient's metrics can be used. Additional patient metrics can include:

Heart rate during assessment (average, peak, mean, mode)
Respiration rate during assessment
Did the patient complete the test (yes/no) or what percentage of the test was completed
Did the patient do a walk test—could be an indicator that patient is having trouble/worsening condition As noted above, all of the physical activity assessment metrics can be normalized in accordance with a predetermined scale and input into the predictive and/or trends analysis.

In some implementations, in addition or alternatively to the above, the patient's overall performance on a physical assessment such as the WalkTest™ may be scored on a normalized scale. The overall performance score can be based on, for example, individual scores for each component of the physical assessment as noted above as well as information related to the health evaluation. For example, the overall performance may be rated on a scale ranging from 0 to 1 as shown in the below table.

TABLE 6

| Example assessment score | Example clinical condition during assessment |
| --- | --- |
| 0 | Patient performed very well on assessment. Obtained average or above average scores on steps, distance, and/or pace metrics. |
| 0.25 | Patient performed reasonably well. May have indicated signs of abnormal fatigue, shortness of breath, and other adverse symptoms during or immediately after the assessment. Obtained average or below average scores on steps, distance, and/.or pace metrics. |
| 0.5 | Patient completed test, but showed signs of abnormal fatigue, shortness of breath, and had poor scores on steps, distance, and/or pace metrics. |

TABLE 6-continued

| Example assessment score | Example clinical condition during assessment |
| --- | --- |
| 0.75 | Patient did not complete assessment. Patient may have stopped assessment due to chronic level symptoms, chest discomfort, and/or palpitations or other conditions. In some scenarios, patient may be scored in this category if patient had very poor scores on steps, distance, and/or pace metrics. |
| 1 | Patient was unable to take assessment |

Referring again to FIG. 11, the complete dataset of physiological metrics 1145 are delivered to a predictive or trends analysis classifier 1150 and an output 1155 is generated. Referring now to FIG. 12, as shown in system 1200, the output 1155 of the predictive or trends analysis classifier 1150 can include a score indicating a current overall clinical condition 1205 of the patient. In the event that the classification of the patient is worsening, e.g., the clinical condition score has a worsening trend and/or transgresses a threshold the system can prompt certain actions. In one example, the classifier may output a score between 0 and 1 indicating the overall patient condition, where a score on the lower end of the scale (e.g., between 0.0 and 0.25) may indicate a stable patient that raises no concerns and a score on the higher end of the scale (e.g., above 0.50) may indicate a poor patient condition in need for close monitoring (e.g., indicates a likelihood of an occurrence of an adverse event). For example, such adverse events may include one or more of an arrhythmia event (VT/VF), a stroke event, a syncopal event, and a hospitalization event. Based upon the current patient condition 1205, the system 1200 can produce a recommended clinically actionable event such as adjust the patient's treatment plan 1210 and can deliver the produced recommendation to a caregiver such as physician 1220.

In certain implementations, information related to the changes in the treatment plan can be fed back to the predictive or trends analysis classifier 1150 as shown in FIG. 11. Such a feedback loop can provide for improvements to the predictive or trends analysis classifier 1150 by including information related to changes to the treatment plan as well as the patient's response to the changes.

In addition or alternately to observing trends in the output score, the scores may be subject to one or more threshold conditions. For example, the threshold conditions may trigger one or more clinically actionable events. Table 7 below provides an example set of patient condition score categories, threshold ranges, and current patient condition information.

TABLE 7

| Patient condition Score-category | Sample score range | Sample patient current condition |
| --- | --- | --- |
| Score-category 1 | Less than 0.25 | Stable, good condition - No concerns about patient condition. Patients at risk for heart failure who have not yet developed structural heart changes (e.g., those with diabetes and/or coronary disease) |

TABLE 7-continued

| Patient condition Score-category | Sample score range | Sample patient current condition |
|---|---|---|
| Score-category 2 | 0.25 to 0.5 | Stable but certain metrics appear elevated - patient under observation; Patients with structural heart disease (e.g., reduced ejection fraction or chamber enlargement) |
| Score-category 3 | 0.5 to 0.75 | Patient condition is concerning - close observation and response to treatment plan warranted Overnight hospital stay may be recommended to bring certain parameters under control; Patients who have developed clinical heart failure |
| Score-category 4 | Greater 0.75 | Admit to hospital for close monitoring; Patients with refractory heart failure requiring advanced intervention (e.g., biventricular pacemakers, left ventricular assist device, transplantation) |

In some implementations, the above score categories may be part of a proprietary scoring scheme for implementation in a proprietary device in accordance with the embodiments described herein. In certain other implementations, the processes may classify patients in accordance with heart failure classifications adopted by a physician's or hospital group, association, or other regulatory authority. For example, such authority may be the American College of Cardiology (ACC), the American Heart Association (AHA), and the New York heart Association (NYHA). In this regard, the device may automatically classify the patients based on similar scoring schemes as noted above into the appropriate classes and/or stages of heart failure. In some implementations, a user may configure in advance via a user set parameter which classification scheme the device is to implement. For example, a user may be prompted at set up to indicate a classification scheme in accordance with one or more the below options. The user may indicate their option via a user interface (e.g., either locally, on the device, or via a remote configuration parameter on a server that is then transmitted to the device).

Proprietary scoring scheme (as described above)
ACC/AHA scheme
NYHA scheme
ACC/AHA scheme can be implemented as follows:
Stage A: Patients at risk for heart failure who have not yet developed structural heart changes (i.e. those with diabetes, those with coronary disease without prior infarct)
Stage B: Patients with structural heart disease (i.e. reduced ejection fraction, left ventricular hypertrophy, chamber enlargement) who have not yet developed symptoms of heart failure
Stage C: Patients who have developed clinical heart failure
Stage D: Patients with refractory heart failure requiring advanced intervention (i.e. biventricular pacemakers, left ventricular assist device, transplantation)

The techniques as described above can be used to map scores from the processes as taught herein to the stages as defined by the ACC/AHA scheme. For example, Table 8 below shows a correlation between the scoring techniques as described above and the ACC/AHA scheme implementation:

TABLE 8

| Patient condition Score-category | Sample score range | ACC/AHA Stage |
|---|---|---|
| Score-category 1 | Less than 0.25 | Stage A |
| Score-category 2 | 0.25 to 0.5 | Stage B At risk for progression to stage C, should be closely monitored |
| Score-category 3 | 0.5 to 0.75 | Stage C Likely to progress to Stage D Action should be taken to slow progression |
| Score-category 4 | Greater 0.75 | Stage D Admit to hospital for close monitoring |

NYHA scheme can be implemented as follows. The NYHA has categorized each of the diagnosis into four classifications. Class I and Class II are considered mild. Class III is considered moderate and Class IV is severe. In Class I there are no restrictions of physical activity. Patients generally don't complain of being overly tired or of experiencing shortness of breath. A patient is still able to control the disease. Regular exercise, limiting alcohol consumption, and eating healthy (with moderate sodium intake), are all actions that can be taken quite easily. High blood pressure will need to be treated. Quitting smoking is crucial.

With Class II heart failure, patients will feel slight restrictions with everyday physical actions like bending over or walking. They will be tired and shortness of breath may occur. Non-invasive surgical procedures like ACE-Inhibitors or Beta Blockers (depending on the patient), may be considered.

Class III heart failure patients experience definite limitations during physical activity. They may remain comfortable at rest, but most all physical activity will cause undue fatigue. Under physician care, their diet and exercise may be monitored. Diuretics, to combat water retention, may be prescribed.

Patients in Class IV heart failure are virtually unable to do any physical activity without discomfort. There may be significant signs of cardiac problems even while resting. Surgical options will be explored along with the same attention given to treatments in Classes I-III.

The techniques as described above can be used to map scores from the processes as taught herein to the stages as defined by the NYHA scheme. For example, Table 9 below shows a correlation between the scoring techniques as described above and the NYHA scheme implementation:

TABLE 9

| Patient condition Score-category | Sample score range | NYHA Class |
|---|---|---|
| Score-category 1 | Less than 0.25 | Class I or Class II |
| Score-category 2 | 0.25 to 0.5 | Class III Adjustments to medication may be made Monitoring to reduce progression to class IV |

TABLE 9-continued

| Patient condition Score-category | Sample score range | NYHA Class |
|---|---|---|
| Score-category 3 | 0.5 to 0.75 | Class IV Surgery likely |
| Score-category 4 | Greater 0.75 | Above Class IV |

Depending on the classification and/or scoring of the patient at any given time, one or more events may be triggered. One such event may be an automated event that is triggered without user input. For example, the system may automatically instruct the external medical device coupled to the patient (e.g., a wearable defibrillator) to increase a sensitivity of its detection process for a period of time while the patient may be at increased risk of a sudden cardiac arrhythmia event. Or, the system may output information about the patient's current condition and provide guidance to a caregiver and/or other person for actions to be taken. Such actions may include recommendations to change a treatment plan for the patient, such as change medication dosage, or place the patient under a higher degree of observation or admit the patient into a hospital.

For example, clinically actionable events may be directed at the external medical device (e.g., a wearable defibrillator), such as but not limited to triggering changes in the controller so that a time from detection of a sudden cardiac arrest to treatment is decreased. Moreover, detection of an increased risk score category may prompt the system to notify the patient, a physician, a responsible third party, a medical team, and/or technical support of the change in risk. In this way, a patient in an increased risk score category can be flagged for more frequent future observation and/or a change in treatment plan.

In some implementations, if the patient's clinical condition is worsening, the caregiver and/or technical support person may cause the patient's external medical device to initiate real-time or substantially real-time streaming of the patient's ECG data (and/or other physiological data) to a remote server for additional monitoring and analysis. For example, as shown in FIG. 12, if the current patient condition 1205 indicates a worsening condition, the system can send an indication to the remote server to perform various notification and/or analysis actions 1215.

In some examples, a period of reporting and/or metric measurement and analysis for such a patient may be increased (e.g., from once every few or more hours, to once every hour). In some examples, additional monitoring and/or reporting of the patient's condition and various physiological parameters may be initiated for the duration of the period during which the patient's condition is concerning (e.g., until patient's condition stabilizes or improves).

In some implementations, if the patient's condition is worsening but has not reached a predetermined critical threshold yet, then no immediate action may be deemed necessary (e.g., if the classifier scores the patient's current condition at or above 0.5 but below 0.65 in the example above), and the physician or technical support person may initiate more frequent reporting of the patient's physiological status (e.g., medical reporting of the patient's condition) or initiate streaming ECG data. Further, if the patient is placed in score category 3 (e.g., at or above 0.5), the physician or technical support person may perform additional actions, e.g., including instructing more frequent checks of the external medical device and/or ensuring that downtime of the continuous monitoring is kept to a minimum.

In the event of a patient in score category 4 having a higher risk for asystole, actions that may be taken are, but are not limited to, notification to the patient and a responsible third party to seek medical attention and notification to the responsible medical team of that patient's risk status.

The adjustments to treatment plan 1210 may be based on making changes to drugs administered to the patient to control and/or treat the patient's underlying heart failure condition or symptoms. As previously noted, heart failure is generally a chronic long-term condition that can worsen with time. Under the ACC/AHA scheme, there are 4 stages of heart failure (Stage A, B, C and D). As the patient's condition gets worse, the patient's heart muscle tends to pump less blood to their organs, and the patient moves toward the next stage of heart failure. In standard care regimens, the goal of HF treatment is to keep the patient from progressing through the stages or to slow down the progression. Treatment at each stage of heart failure can involve changes to medications, lifestyle behaviors, and cardiac devices. In various implementations, the patient monitoring system can base recommendations on the ACC/AHA or NYHA treatment guidelines. The below outlines a basic plan of care that may apply to patients in accordance with their stage/classification.

In accordance with implementations, the patient monitoring device and/or system may recommend one or more of the following actions. These actions may be recommended via the user interface of the device directly to the patient. In some cases, the proposed treatment plan and/or changes to the treatment plan may be recommended to the patient's primary caregiver and/or physician.

Typical ACC/AHA Stage A is considered pre-heart failure. In this stage, patients are monitored for signs of hypertension, diabetes, coronary artery disease, metabolic syndrome, a history of alcohol abuse, a history of rheumatic fever, a family history of cardiomyopathy, a history of taking drugs that can damage heart muscle, such as some cancer drugs. An example Stage A treatment plan that may be recommended by the patient monitoring system includes the below.

Perform ECG monitoring only
    The monitoring device may not initiate bio-vibrational and/or radio frequency-based TFC monitoring of the patient
Regular exercise, being active, walking every day
Quitting smoking
Treatment for high blood pressure (medication, low-sodium diet, active lifestyle)
Treatment for high cholesterol
Not drinking alcohol or using recreational drugs
Medications:
    Angiotensin converting enzyme inhibitor (ACE-I) or an angiotensin II receptor blocker (ARB) if the patient has coronary artery disease, diabetes, high blood pressure, or other vascular or cardiac conditions
    Beta-blocker if the patient has high blood pressure ACC/AHA Stage B is considered pre-heart failure. This means the patient has been diagnosed with at least systolic left ventricular dysfunction but may have never had symptoms of heart failure. Most people with Stage B heart failure may have an echocardiogram (echo) that shows an ejection fraction (EF) of 40% or less. This category can include people who have heart failure and reduced EF (HF-rEF) due to any cause. An example Stage A treatment plan that may be recommended by the patient monitoring system includes the below.

Continuing or modifying treatments listed in Stage A
  For example, the monitoring device may initiate bio-vibrational and/or radio frequency-based TFC monitoring of the patient.
  For example, a frequency of the TFC measurement may be increased. If initially the TFC was being measured on a weekly basis, it may be changed to be taken every 2-3 days.
  For example, the monitoring device may initiate administering physical assessments and/or physical tests to the patient.
Adding Angiotensin converting enzyme inhibitor (ACE-I) or angiotensin II receptor blocker (ARB) (if the patient is not already taking as part of the patient's Stage A treatment plan)
Adding Beta-blocker if the patient has had a heart attack and if the patient's EF is 40% or lower (if patient is not already taking as part of Stage A treatment plan)
Adding Aldosterone antagonist if the patient has had a heart attack or if the patient has diabetes and an EF of 35% or less (to reduce the risk of the patient's heart muscle getting larger and pumping poorly)
Possible wearable cardioverter defibrillator therapy
Consider possible surgery or intervention as treatment for coronary artery blockage, heart attack, valve disease (the patient may need valve repair or replacement surgery) or congenital heart disease.

ACC/AHA Stage C patients generally have been diagnosed with heart failure and currently or previously exhibited signs and symptoms of the condition. There are many possible symptoms of heart failure. The most common are:
  Shortness of breath
  Feeling tired (fatigue)
  Less able to exercise
  Weak legs
  Waking up to urinate
  Swollen feet, ankles, lower legs and abdomen (edema)

An example Stage C treatment plan that may be recommended by the patient monitoring system includes the below.

Continuing or modifying treatments listed in Stages A and B
  For example, the monitoring device may initiate (if not already monitoring) bio-vibrational and/or radio frequency-based TFC monitoring of the patient.
  For example, a frequency of the TFC measurement may be increased. If previously the TFC was being measured on a 2-3-day basis, it may be changed to be taken every day.
  For example, the monitoring device may initiate frequent physical assessments and/or physical tests to the patient.
Adding beta-blocker (if the patient is not already taking such medication)
Adding Aldosterone antagonist (if the patient is not already taking such medication) if a vasodilator medicine (e.g., ACE-I, ARB or angiotensin receptor/neprilysin inhibitor combination) and a beta-blocker do not relieve the patient's symptoms
Adding Hydralazine/nitrate combination if other treatments do not relieve the patient's symptoms.
Adding medications that can slow the heart rate if, e.g., the patient's heart rate is greater than 70 beats per minute and the patient still has symptoms Adding a diuretic ("water pill") if thoracic fluid content and/or S3 intensity continues to worsen
Recommend restricting sodium (salt) in diet.
Recommend tracking patient's weight every day.
Possible fluid restriction if thoracic fluid content and/or S3 intensity continues to worsen
Possible cardiac resynchronization therapy (e.g., biventricular pacemaker)
Possible implantable cardiac defibrillator (ICD) therapy
If treatment causes the patient's symptoms to get better or stop, the patient may still need to continue treatment to slow the progression to Stage D.

Patients with Stage D and reduced EF (HF-rEF patients) have advanced symptoms that generally do not get much better with treatment. This is usually considered a final stage of heart failure. An example Stage D treatment plan that may be recommended by the patient monitoring system includes the below.

Continue treatments and/or modifying treatments listed in Stages A, B and C
Evaluation for more advanced treatment options, including:
  Heart transplant
  Ventricular assist devices
  Heart surgery
  Continuous infusion of intravenous inotropic drugs
  Palliative or hospice care
  Research therapies The one or more physiological measurements extracted from the ECG signal may include one or more of heart rate, heart rate variability, PVC burden or counts, activity, noise quantifications, atrial fibrillation, momentary pauses, heart rate turbulence, QRS height, QRS width, changes in the size or shape of the morphology, cosine R-T, artificial pacing, corrected QT interval, QT variability, T wave width, T wave alternans, T-wave variability, ST segment changes, early repolarization, late potentials, fractionated QRS/HF content, and fractionated T wave/HF content.

The control unit can detect fiducial points, e.g., points corresponding to P, Q, R, S, and T waves, in the ECG signal to extract individual measurements, e.g., QRS, PVC, etc., from the physiological parameter data. For example, a QT interval may provide a measure of heart failure of a subject, and the distance between the Q point and the T point may be determined and extracted from the physiological parameter signal.

Figure 13:
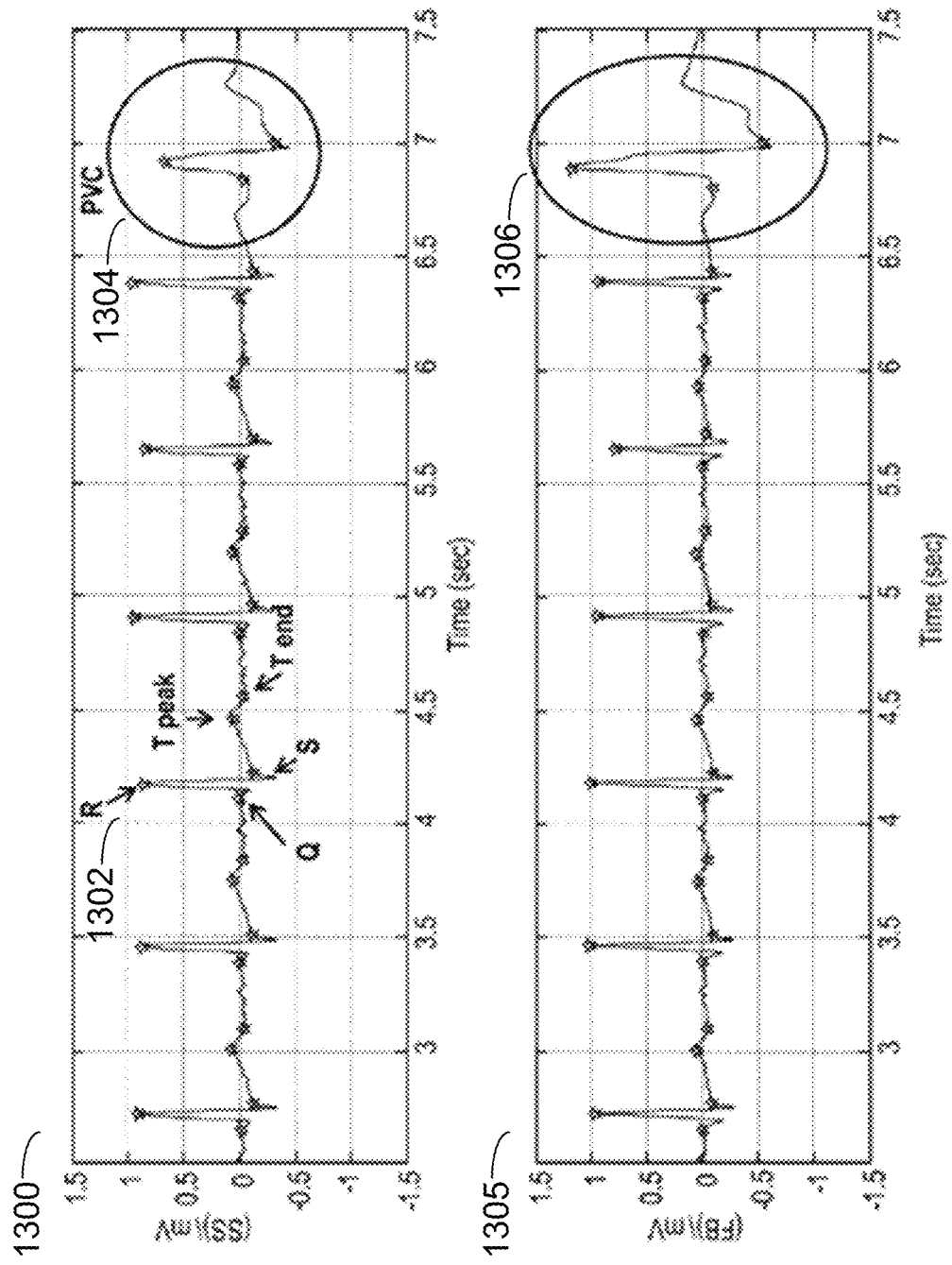
FIG. 13 depicts a sample dual-lead ECG signal, in accordance with an example of the present disclosure.

FIG. 13 illustrates a dual-lead ECG signal including a plot 1300 for a side-side (SS) lead as well as a plot 1305 for a front-back (FB) lead. In certain implementations, a processing device can be configured to identify various information such as QRS measurements and a PVC parameter in each ECG signal for extraction. For example, the processing device can apply a QRS detector and a PVC detector to the ECG signal to extract QRS measurement information 1302 and PVC measurement information 1304 from the SS lead plot 1300. The processing device can further extract, for example, PVC measurement information 1306 from FB lead plot 1305.

In certain implementations, the extracted QRS and PVC measurements and/or the fiducial points determined by the QRS detector and the PVC detector can be used by the processing device to identify and extract various other measurements or parameters in the ECG signal, e.g., heart rate variability (HRV), RR intervals, etc. For example, output from the QRS detector and the PVC detector may be used by an AFIB detector, a pause detector, a pace detector, a morphology detector, a T wave detector, and/or any other detector in the control unit that extracts measurements or parameters from the ECG signal. QRS, PVC, and other detectors are well-known in the art, for example, as described in (Kohler, Hennig, et al.), The Principles of Software QRS Detection, IEEE ENGINEERING IN MEDICINE AND BIOLOGY, (January/February 2002), the entire contents of which are incorporated by reference.

HRV measurement quantifies the variability over time of the R-R interval in the electrocardiographic signal of the patient. The R-wave of a particular heartbeat corresponds to the point in the cardiac cycle of the early systolic phase, and from a signal processing point of view, provides a reliable time-fiducial for making cardiac cycle interval measurements. HRV is affected by the autonomic nervous system, which consists of the sympathetic nervous system (SNS) and the parasympathetic nervous system (PNS). Observed HRV is believed to be an indicator of the dynamic interaction and balance between the SNS and PNS, providing a measure of nervous system competence. HRV serves as an indicator for the diagnosis and assessment of a variety of conditions that are affected by the autonomic system ranging from congestive heart failure to sleep apnea. For example, decreased HRV has been found to be a predictor of increased mortality in the elderly for coronary heart disease. Decreased HRV is also seen after sudden cardiac arrest.

A variability measure related to HRV is T-wave alternans which is a measure of the variation in the recovery of the myocardium during the diastolic (relaxation) phase and measures the fluctuations in the amplitude of the T-wave of the ECG.

In one example, extracting the HRV data can include filtering the ECG signal to remove noise and artifacts; locating a QRS complex within the filtered ECG signal; finding a RR interval between successive R peaks; and processing the RR intervals to obtain the HRV. For example, a band pass filter is used to filter the ECG signal and locate the QRS complex. A band pass filter with an operating frequency range wider than the frequency components of the QRS complex has to be used. The frequency components of the QRS complex lie between 10 to 25 Hz. Thus, in one embodiment of the present disclosure, the operation frequency range of the band pass filter is between about 5 Hz to about 28 Hz.

In one example, the R wave may be located as follows. A maximum peak data value first occurring in the filtered ECG signal is located. An upper amplitude threshold and a lower amplitude threshold from the located maximum peak value are determined. A peak value and minimum values on either side of the peak value are located. In this embodiment of the present disclosure, either side refers to the left and right sides of the peak value. The conditions of whether the peak value is above the upper amplitude threshold, while the minimum values are below the lower amplitude threshold are met is checked. If the conditions are met, the location of the peak value is denoted as an R position. The location of the minimum value occurring closest on the left side of the R position is denoted as a Q position, and the location of the minimum value occurring closest on the right-hand side of the R position is denoted as an S position. With reference to a time scale that the filtered ECG signal is plotted against, the Q position occurs at where the minimum value first occurs before the R position, while the S position occurs at where the minimum value first occurs after the R position. The location of a QRS peak within the filtered ECG signal is thus determined.

In one embodiment of the present disclosure, where a 1D array of ECG sample points x(n) are provided, the upper and lower amplitude thresholds ($T_{upper}$ and $T_{lower}$) are set after finding the maximum value (ref_peak) within the first few seconds of data. The thresholds are defined as:

$T_{upper}$=ref_peak+0.4*ref_peak $T_{lower}$=ref_peak−0.35*ref_peak

Then an R wave is said to occur at the point i if the following conditions are met:

x(i) lies between $T_{upper}$ and $T_{lower}$;

$x(i+1)-x(i)<0$; and $x(i)-x(i-1)>0$;

where the R-peak is the point with maximum value.

The positions of other R waves within the filtered ECG signal may be located by iterating the process of: locating another peak value and locating other minimum values on either side of the another peak value. When the another peak value is above the upper amplitude threshold while the other minimum values are both below the lower threshold, the location of the peak value is denoted as an R position. The location of the minimum value occurring closest on the left side of the R position is denoted as a Q position and the location of the minimum value occurring closest on the right side of the R position is denoted as an S position. In this manner, the location of another QRS peak is determined.

In examples, the heart rate variability data may include time domain data, frequency domain data and geometric domain data.

The time domain data may include information on any one or more of the following parameters: mean of RR intervals (mean RR), standard deviation of RR intervals (STD), mean of the instantaneous heart rate (mean HR), standard deviation of the instantaneous heart rate (STD_HR), root mean square of differences between adjacent RR intervals (RMSSD), number of consecutive RR intervals differing by more than 50 ms (NN50), and percentage of consecutive RR intervals differing by more than 50 ms (pNN50).

The frequency domain data may include information on any one or more of the following parameters: power in very low frequency range (<=0.04 Hz) (VLF), power in low frequency range (0.04 to 0.15 Hz) (LF), power in high frequency range (0.15 to 0.4 Hz) (IF), total power which is estimated from the variance of NN intervals in the segment and is measured in ms2 (TP), ratio of LF power to HF power (LF/IF), LF power in normalized units: LF/(TP−VLF)×100 ($LF_{norm}$), and HF power in normalized units: HF/(TP−VLF)×100 ($HF_{norm}$).

All of the above physiological parameters and metrics related to the patient condition are collected as described. Within the physiological parameters data, one set of data may not contain the same number of parameters compared to another set of data. Further, the patient parameters can be stored as digital data converted from the form in which each of the four parameters is originally obtained (such as an analog signal). Data for patient characteristics such as demographics and medical history may be transmitted to the system via a wireless network distributed through a hospital or physician network. All the physiological parameters may be used to train the predictive analysis process. In addition, patient demographics (e.g., age, gender) and medical history information may be used to train the process. At the conclusion of the training phase, the parameters found to be most relevant to achieving a high level of accuracy will then be used as inputs to the real time detection system.

The physiological parameters can be stored in an electronic database. In examples, this data includes a plurality of sets of data, each set having at least one of a first parameter relating to cardio-vibrational data and a second parameter relating to radio frequency-based thoracic fluid content levels. Each of the plurality of sets of data further has a third, "output" parameter relating to the patient condition, e.g., a patient condition score.

The electronic database used to store patient physiological parameters may be a memory module such as a hard disk drive, an optical disc, or solid-state devices. During the training phase of the artificial neural network, the training patient physiological parameters may be obtained from hospital records or from conducting field studies of a pool of patient(s), where the pool includes at least one group of patients that is designated to serve as a control group. Thus, the patient physiological parameters may include data of patients suffering from various heart related conditions, patients who may be considered healthy, such as those showing no signs of cardiac conditions, and further patients of various demographics.

A third, output parameter is also trained within the process. This parameter is occasionally referred to as the outcome, e.g., death, other adverse event, recovery from an adverse event, or a current condition of a patient. An electronic device may incorporate a processor or memory module storing instructions to implement the trained process, so that the device can analyze physiological parameters of a patient being examined. The output of the electronic device can then be used to assist an operator or a medical professional to predict the outcome of the patient and thereby make appropriate clinical decisions on how to treat the patient.

For example, the process used may depend on a type of the medical event to be predicted, and in accordance with the event, classify or categorize the patient into an appropriate heart failure score category (or NYHA class or ACC/AHA stage). For example, a processing device can be configured to use a first process or process to calculate an event estimation of risk score for a cardiac arrest and a second, different process or process to calculate an event estimation of risk score for a ventricular fibrillation. A risk of impending acute degeneration of a subject's medical condition into cardiac arrest or other severe cardiopulmonary conditions may thus be calculated by a variety of methods. Different methods and processes may be used to calculate the event estimation of risk scores for different time periods. For example, the processing device can be configured to use a first process or process to calculate an event estimation of risk score for a cardiac arrest in a first-time period and a second, different process or process to calculate an event estimation of risk score for a cardiac arrest in a second, different time period.

In some implementations, a machine learning classifier as described in further detail below can be trained on a large population, for example, a population that can range from several thousand to tens of thousands of patient records comprising electrophysiology, demographic and medical history information. The machine learning tool can include but is not limited to classification and regression tree decision models, such as random forest and gradient boosting, (e.g., implemented using R or any other statistical/mathematical programming language). Any other classification-based machine learning tool can be used, including artificial neural networks (as described in more detail below) and support vector machines. Because the machine learning tool may be computationally intensive, some or all of the processing for the machine learning tool may be performed on a server that is separate from the medical device.

An overview of how a random forest tool may be applied to a given dataset can illustrate how a classification tool may work in interpreting given parameters or metrics. A random forest is a collection of decision trees. A decision tree is a flow chart-like structure in which each node represents a test on a metric and each branch represents the outcome of the test. The tree culminates in a classification label, e.g., a decision taken at the end after computing each of the metrics. Each tree in a random forest tool gets a "vote" in classifying a given set of metrics. There are two components of randomness involved in the building of a random forest. First, at the creation of each tree, a random subsample of the total data set is selected to grow the tree. Second, at each node of the tree, a "splitter variable" is selected and the underlying patients are separated into two classes. For example, patients in one class (e.g., Response or occurrence of sudden cardiac arrest) can be separated from those in another class (e.g., Non-Response). The tree is grown with additional splitter variables until all terminal nodes (leaves) of the tree are purely one class or the other. The tree is "tested" against patient records that have been previously set aside. Each patient testing record traverses the tree, going down one branch or another depending on the metrics included in the record for each splitter variable. The patient testing record is assigned a predicted outcome based on where the record lands in the tree (a vote). The entire process may be repeated with new random divisions of the underlying dataset to produce additional trees and ultimately a "forest". In each case, a different subset of patients can be used to build the tree and test its performance.

In developing the results described in the below example implementation, a predetermined number of model variations are trained. For example, each model variation is labeled sequentially, (e.g., for 100 runs, labeled from 1-100). In each run of the model, the software randomly sampled a predetermined portion (e.g. an 80% portion) of the population as the training set and set aside the remainder (e.g., 20%) as the validation set.

As noted above, the machine learning tool can train the classifier on a first portion of the underlying dataset and validate the classifier on a second portion of the dataset or on another separate dataset. When evaluating the performance of each classifier, the performance of the underlying decisions within the decision trees in the random forest can be evaluated based on specificity and sensitivity parameters. For example, the sensitivity parameter can be based on a measure of the classifier's ability to correctly predict whether a patient is at risk of requiring treatment in accordance with an appropriate score category. For example, the sensitivity parameter may be based on a proportion of patients who are appropriately treated that the model correctly predicts are at risk of being treated. The specificity parameter can be based on the proportion of patients who are not treated, and who are predicted by the relevant classifier as not at risk of requiring treatment. It may be advantageous to optimally balance individual performance variables such as sensitivity and specificity at a high level. For example, by setting the specificity at a relatively high value, e.g., 95%, the underlying thresholds within the classifier model may be adjusted to minimize false positives. After the specificity is defined, the measure of sensitivity can be treated as a type of performance measure, e.g., generally in the range of 15-35% for a given model, however, smaller or larger values of sensitivity are also possible.

A validation protocol, for example, as described below, can be employed to validate the predictive performance of trained models. In an implementation, the validation phase can be used to ascertain appropriate threshold scores for classifying future patients (where an outcome is currently unknown and a prediction of the outcome is desired) and to determine the predictive performance of each classifier model generated by the machine learning tool. For validating the various classifiers and associated threshold scores, a second group of individuals, e.g., a validation population (or cohort), can be used. For example, the validation population used can be a new validation population. The outcome for the patients in the validation cohort is eventually learned as these patients progress to the device end of use. In an embodiment, the patients in the validation population can be different from the group of training and test patients described above for training the classifier. For example, a validation population of patients and their associated metrics (validation metrics) can be independent from a training population of patients and associated metrics (training metrics). In some implementations, there may be an overlap between the validation metrics and the training metrics.

In some implementations, the validation population can be updated by at least one of 1) adjusting one or more of the metrics in the validation metrics, and 2) expanding the validation metrics based on appending additional one or more subjects to population of subjects that make up the validation population. The thresholds for classifying future patients can be refined based on the updated validation metrics. For example, metrics of a patient that is currently being treated or monitored or has otherwise not progressed through the device end of use can be used to adjust the one or more metrics in the validation metrics or the patient's metrics can be added to the validation population as metrics from a new subject. The validation metrics can be adjusted as new metrics for the patient are determined during the monitoring or treatment of the patient. In some examples, as a monitored patient progresses through the device end of use, the patient's metrics can be added to the validation population and/or used to adjust the metrics in the validation metrics after the patient has progressed through the device end of use.

In some implementations, the training population can be updated by at least one of 1) adjusting one or more of the metrics in the training metrics, and 2) expanding the training metrics based on appending additional one or more subjects to the first plurality of subjects. The machine learning classifier models can be retrained based on the updated training metrics. For example, as additional patient metrics are determined from current patients and/or metrics from new patients are determined, the machine learning classifier can be retrained, e.g., on the increased number of metrics or on new, different metrics, to provide updated classifier models. The training population can be updated as new metrics for current patients and/or metrics for new patients are determined or after patients have progressed through a device end of use.

Figure 14:
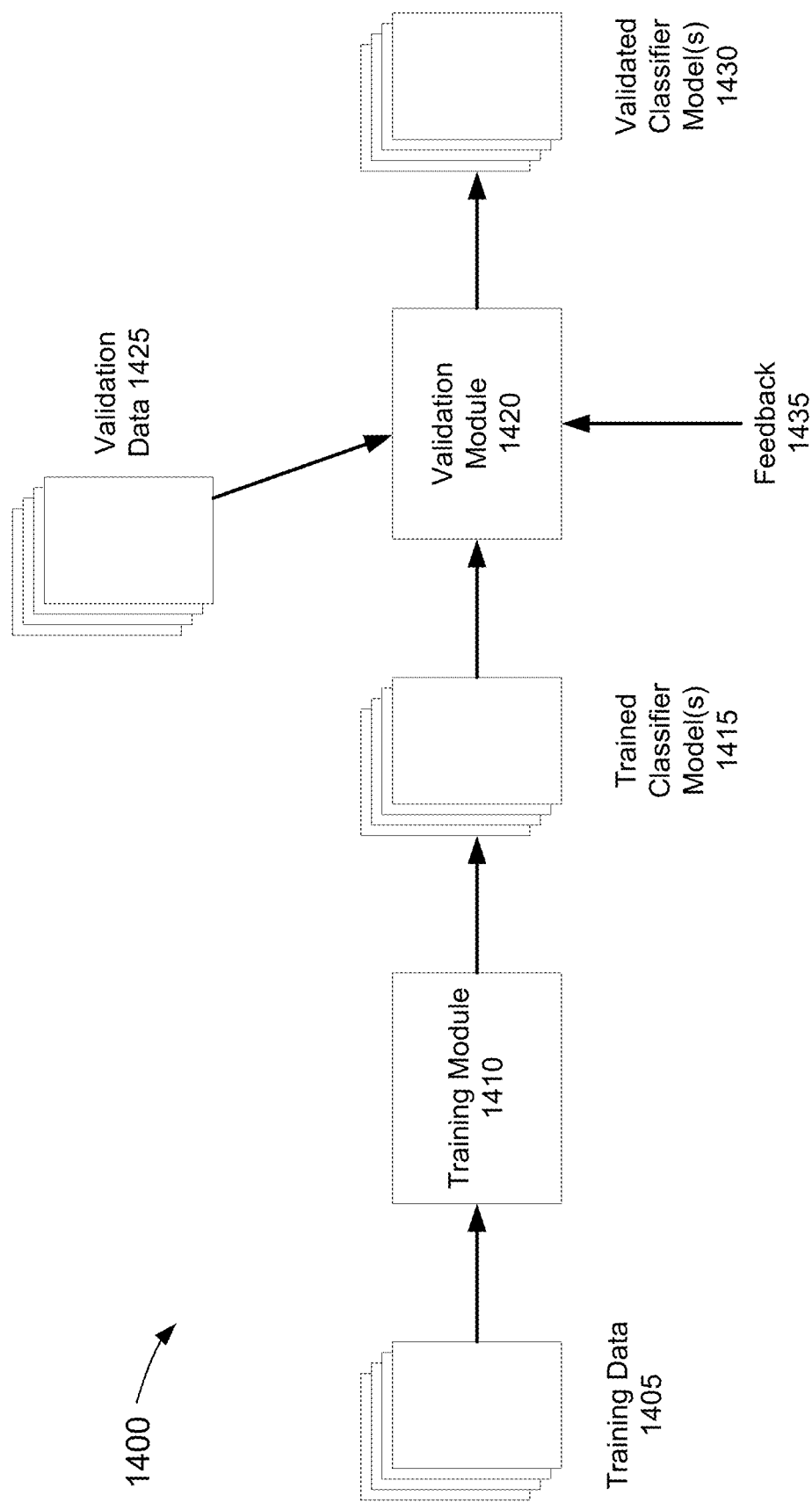
FIG. 14 depicts a sample process for developing a machine learning process, in accordance with an example of the present disclosure.

FIG. 14 illustrates a sample flow 1400 for training and validating one or more classifier models for a machine learning process as described above. A set or population of known patient records can be provided as the data set used to train and validate the classifier models. For example, the known patient records data set may include 1000 patients that have suffered from a specific type of heart condition such as VT, their treatment regimens, and the associated outcomes for each patient. A percentage of the known patient data records can be used as the training data set 1405. For example, 80%, or 800, of the patient records can be used as the training data set 1405. The training data 1405, as noted above, can include a variety of available information for a plurality of patients, including the patient's ECG metrics 1125 (see, e.g., FIG. 11), bio-vibration metrics 1130, radio frequency metrics (1135), combinational physiological metrics 1145, demographics and medical history information 1140, and patient activity and test data 1142. The training data 1405 can include for each of the training data sets historical information regarding how each training data set was classified or scored into an appropriate score category (or NYHA class or ACC/AHA stage).

The training date set 1405 can be fed into a training module 1410. The training module 1410 can include one or more untrained data structures such as a series of data trees (e.g., organized using a random forest tool as described above). Using the known input variables and known outcomes from the training data set 1405, the training module 1410 can iteratively process each data point in the training set, thereby training the data structures to more accurately produce the expected (and known) outcomes.

Once the training module 1410 has exhausted the training data set 1405, the training module can output one or more trained classifier models 1415. The one or more trained classifier models 1415 can represent a set of models that provide the most accurate classification and generation of an outcome for a known set of input variables that could be generated from the training data 1405. A validation module 1420 can be configured to further refine the trained classifier model(s) 1415 using additional patient records. For example, a validation data set 1425 can be input into the validation module 1420 for validation of the one or more trained classifier models 1415. To continue the above example, the validation data set 1425 can include 200 patient records. Typically, there is no overlap between a training data set and a validation data set as there is no advantage to running the same data set twice.

As shown in FIG. 14, the validation module 1420 can process the validation data set 1425 to produce one or more validated classifier models 1430. Depending upon the intended purpose of the validated classifier models 1430, the models can have a certain specificity or sensitivity as described above.

As the validated classifier models as used to classify new patients (e.g., to produce new outputs for a set of patient metrics as described herein), the produced outcomes can be used to better validate the process using a closed loop feedback system. For example, as a patient is classified and treated, the result of that treatment can be included in the patient record and verified by, for example, the patient's physician. The patient's record, now updated to include a known outcome, can then be provided as feedback 1435 to the validation module 1420. The validation module can process the feedback 1435, comparing a generated output against the known outcome for the patient. Based upon this comparison, the validation module 1420 can further refine the validated classifier models 1430, thereby providing a closed loop system where the models are updated and upgraded regularly.

Figure 15:
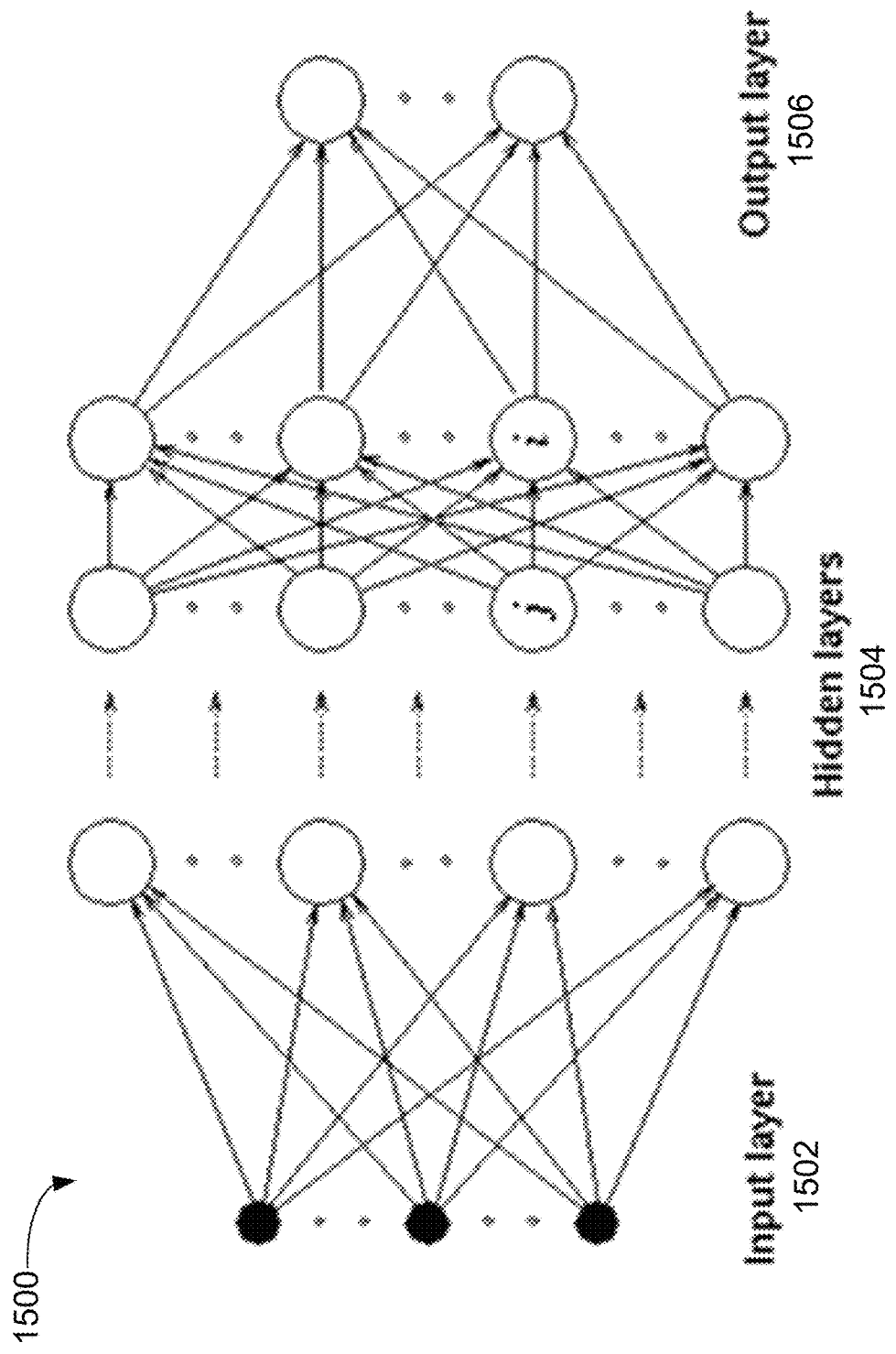
FIG. 15 depicts a sample architecture of an artificial neural network, in accordance with an example of the present disclosure.

In another example, the process can be implemented as a network of nodes interconnected to form an artificial neural network. For example, FIG. 15 illustrates a topography for a sample artificial neural network 1500. The artificial neural network 1500 can include, for example, one or more nodes organized into an input layer 1502, a series of hidden layers 1504, and one or more nodes organized into an output layer 1506.

In an artificial neural network, the nodes include a plurality of artificial neurons, each artificial neuron having at least one input with an associated weight. The artificial neural network can be trained using the physiological parameters such that the associated weight of the at least one input of each artificial neuron of the plurality of artificial neurons is adjusted in response to respective first, second and third parameters of different sets of data from the patient physiological parameters. This results in the artificial neural network being trained to produce a patient condition score.

An artificial neural network may be a mathematical model or computational model simulating the structure and/or functional aspects of a biological neural network. In embodiments, the nodes of the artificial neural network include at least one input, at least one neuron and at least one output. The neuron may be present in a single hidden layer of the artificial neural network and may take two or more inputs. In examples where the artificial neural network has a plurality of neurons, the plurality of neurons may be distributed across one or more hidden layers. Where there is more than one layer, each layer may be interconnected with a previous and a subsequent layer.

The artificial neural network may be an adaptive system, where it changes based on external or internal information that flows through the artificial neural network during the training or learning phase. Specifically, the weight (or strength) of the connections (such as between adjacent artificial neurons, or between an input and an artificial neuron) within the artificial neural network is adapted to change to match the known outputs.

In examples, a first parameter (e.g., S3 vibration intensity), and a second parameter (e.g., tissue fluid content) or a combination of the first parameter and the second parameter may be classified as feature vectors of the patient physiological parameters. The artificial neural network may be trained with the feature vectors. The artificial neural network may be implemented as instructions stored in a memory that when executed by a processor cause the processor to perform the functions of the artificial neural network. In embodiments of the present disclosure, the artificial neural network may be based on support vector machine architecture, wherein the associated weight of the at least one input of each artificial neuron of the plurality of artificial neurons is initialized from a library used by the support vector machine.

The support vector machine may have an aggregated output comprising a decision function, the decision function given by $$f(x) = \mathrm{sgn}\left(\sum_{i=1}^{N} \alpha_i y_i k(x, x_i) + b\right)$$

wherein sgn( ) is a sign function, (x,xi) is set of feature vector, k(x,xi) is a kernel matrix constructed by x and xi, yi is 1 or −1, which is the label of feature vector xi, αi and b are the artificial neural network parameters.

For example, the artificial neural network may be based on an extreme learning machine architecture, wherein the associated weight of the at least one input of each artificial neuron of the plurality of artificial neurons is initialized through random selection by the extreme learning machine. The artificial neural network may be realized as a single-layer feed-forward network, whereby the prediction on the survivability of the patient is derived from the function, $$f_{\hat{N}}(x_j) = \sum_{i=1}^{\hat{N}} \beta_i g(w_i \cdot x_j + b_i) = t_j \quad j = 1, \ldots, N$$

wherein xj is an input vector to an input of one of the plurality of neurons for j=1, 2, ..., N input vectors; wi is the associated weight of the input of the neuron receiving the xj input vector; g(wi·xj+bi) is an output of the neuron receiving the xj input vector ... for i=1, 2, ..., N artificial neurons; βi is the output weight vector that associates an ith hidden neuron with a respective output neuron; and bi is the bias for the ith hidden neuron.

Training of the artificial neural network may be based on back-propagation learning. For example, the back-propagation learning may use the Levenberg-Marquardt process. Each of the plurality of neurons of the artificial neural network may have an activation function, the activation function being selected from a group of functions comprising hardlim, sigmoid, sine, radial basis and linear.

In examples, the result of the artificial neural network may be only two possible values: either patient condition is stable and good (no adverse event expected) or admit patient to hospital (adverse event expected).

In another example, the physiological parameters data may be partitioned into many portions. A first set of parameters may relate to ECG metrics of a patient; a second set of parameters may relate to cardio-vibrational metrics of the patient and a third set of parameters may relate to patient demographics and history. The first set of parameters, the second set of parameters and the third set of parameters are provided as sets of normalized data values that are then input to a scoring scheme. For example, the scoring scheme may assign a respective category for each parameter of the first set of parameters, the second set of parameters and the third set of parameters. Each category may have a plurality of pre-defined value ranges, each of the plurality of value ranges having a pre-defined score. A score for each parameter of the first set of parameters, the second set of parameters and the third set of parameters is determined by assigning the sets of normalized data to respective pre-defined value ranges, encompassing the sets of normalized data values, of the plurality of value ranges of the category associated to the respective parameter of the first set of parameters, the second set of parameters and the third set of parameters. A total score may be derived based on a summation of the score for each parameter of the first set of parameters, the second set of parameters and the third set of parameters as an indication of the condition of the patient. The scoring scheme may be any suitable process or process, implementable in an electronic database, which can assign a score to each range of values within each category associated to each parameter of the first set of parameters, the second set of parameters and the third set of parameters. For instance, the scoring scheme may be based on a mathematical model using logistic regression, such as univariate analysis.

In examples, the output patient condition score may be a numerical value, which may be determined according to statistical information or standard medical information.

In addition to using a learning process such as an artificial neural network or machine learning process as described above, trends analysis can also be used to monitor a patient for changes in their condition and provide output such as changes to the patient's treatment regimen. In certain implementations, a trends analyses can include determining a presence of a substantial relationship between changes in two or more physiological parameters. For example, as described above in regard to FIG. 10, detecting a change in one particular metric can trigger monitoring of another metric. This additional monitoring can be performed to confirm trends in the monitored metrics as well as to provide additional information related to the overall condition of the patient.

One example of a trends analysis is a correlation analysis. A correlation analysis is the quantification of a linear relationship between two variables and can be represented by a value between negative 1.0 and 1.0, generally referred to as the Pearson Product Moment correlation coefficient and denoted as r. As the correlation coefficient approaches 1.0, it indicates a strong and positive association between the two variables. As the correlation coefficient approaches negative 1.0, it indicates a weak and negative association between the two variables. A correlation value close to zero indicates no linear associated between the two variables.

In certain examples, there may be two sets of data samples, X and Y. For example, the X data set may be data sampled from curve X such as a cardio-vibrational S3 intensity curve, and the Y data set may be data sample from curve Y such as a thoracic fluid content measurement curve. In certain implementations, a correlations analysis can be performed using the Pearson correlation function, the Fisher transformation, or other similar correlation functions. For example, using the Pearson correlation function, correlation between n pairs of data {X, Y} can be calculated, wherein X and Y are samples of fixed duration. To continue the above example, X can be measured from the S3 intensity curve and Y can be measured from the TFC measurement curve. The Pearson Product Moment r as noted above can be obtained by substituting variances and covariances based samples of the {X, Y} data sets. The resulting value for r is a value between −1.0 and 1.0. In this example, a value of 1.0 would indicated a perfect X, Y relationship, i.e., that as S3 vibration intensity increases then TFC measurement increases accordingly. A value of −1.0 would indicate a perfect negative relationship. For example, as S3 vibration intensity increases then TFC measurement decreases. Conversely, as S3 vibration intensity decreases then TFC measurement increases. A value of 0.0 implies there is no linear relationship between the variables.

As described herein, multiple metrics can be correlated to determine a condition for a patient. For example, if a patient is likely to experience an adverse cardiac event such as an arrhythmia, there can be a high correlation between thoracic fluid content (TFC) and S3 vibration intensity. Using the process as described in FIG. 10, TFC can be considered as metric 1 and represented on a normalized scale from 0 to 1000. Other normalized linear or non-linear scales may be used. For example, the scale may be from 0 to 1, or 0 to 10, or 0 to 100. For example, a nonlinear scale may be a logarithmic scale. A processing device can monitor the TFC to detect any changes or trends in a patient's TFC value.

Figure 16A:
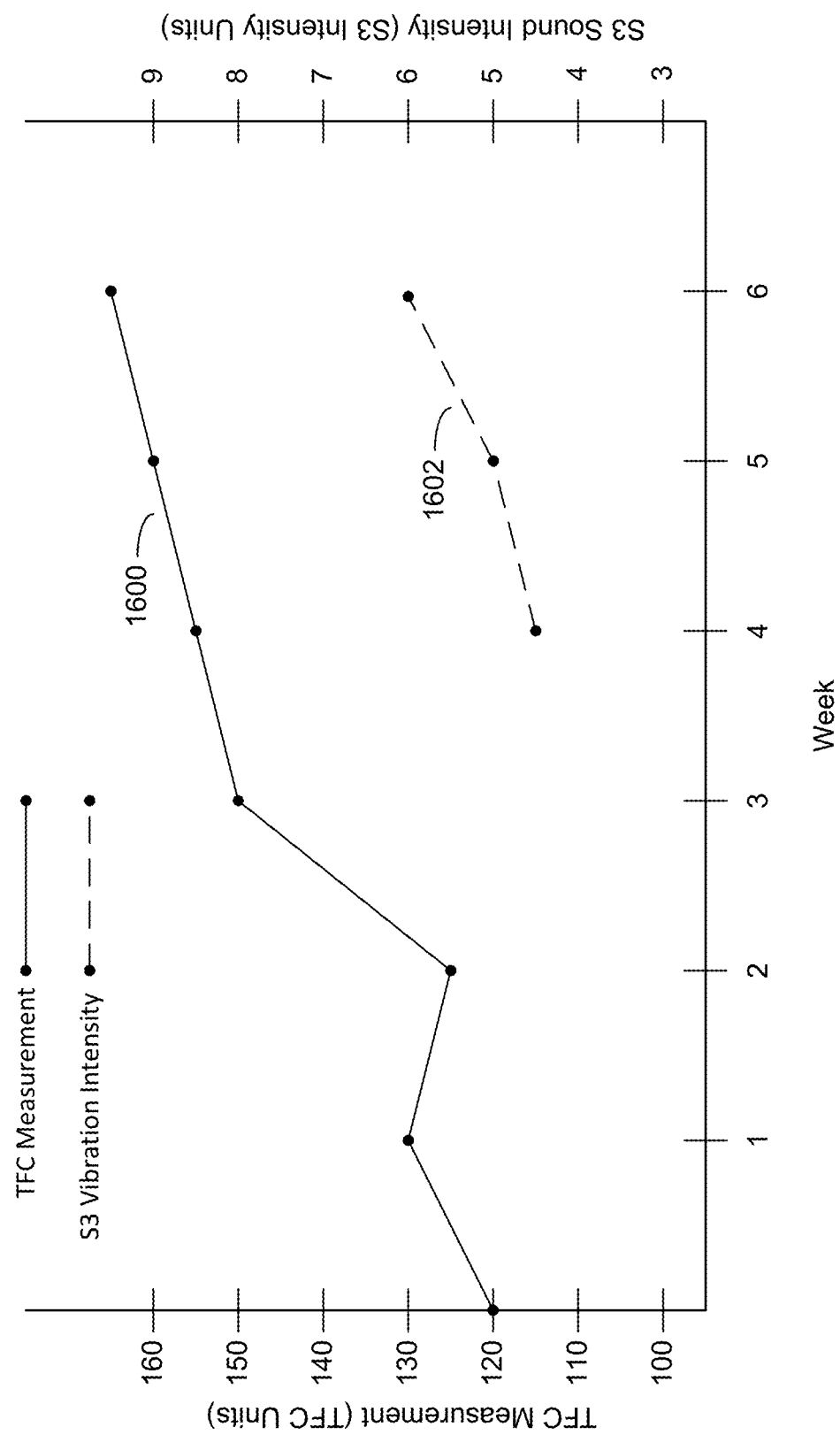
FIGS. 16A-D illustrate sample graphs of trends analysis results with the y-axis based on normalized units, in accordance with an example of the present disclosure.

For example, as shown in FIG. 16A, the processing device can record the patient's TFC measurement over the course of several weeks. As shown in FIG. 16A, the TFC measurements are represented by line 1600. An initial measurement of the patient's TFC, for example, can include a TFC measurement of 120 TFC units. In some examples, TFC units can be measured on a normalized scale of 0-200 TFC units. However, as shown in FIG. 16A, the plot is adjusted to focus on a range of 100-160 TFC units. At week 1, the TFC measurement may increase to 130 TFC units. However, in week 2 the TFC measurement may decrease to 125 TFC units. At week 3, the TFC measurement may increase to 150 TFC units and at week 4 the TFC measurement may increase to 155 TFC units. Depending upon the programming of the processing device, the processing device may trigger a second metric measurement based upon the changes in TFC measurement. For example, the TFC measurement may have exceeded a predetermined threshold value (e.g., 150 TFC units) or a predetermined threshold period of time (e.g., two weeks of successive increases in TFC units, or an increase in three out of four weeks). These changes may trigger the processing device to monitor at least one additional metric. For example, as shown in FIG. 16A, at week 4 the processing device began measuring S3 vibration intensity as well, represented by line 1602.

As noted above, S3 vibration intensity can be measured on a normalized scale of 0-10 S3 intensity units, where 5.0 S3 intensity units indicates a threshold that a patient may be experiencing heart disease and/or require additional treatment. Other normalized linear or non-linear scales may be used. For example, the scale may be from 0 to 1 S3 intensity units, or 0 to 10 S3 intensity units, or 0 to 100 S3 intensity units. For example, a nonlinear scale may be a logarithmic scale. As shown in FIG. 16A, the initial reading as shown can be adjusted to focus on a range of 3-9 S3 intensity units. At week 4 the patient's S3 vibration intensity is measured as 4.5 S3 intensity units. However, at week 5 the patient's S3 vibration intensity has increased to 5.0 S3 intensity units and by week 6 the patient's S3 vibration intensity has increased to 6.0 S3 intensity units. During this same time, the patient's TFC measurement has continued to increase as well, to 155 TFC units in week 5 and to 165 TFC units in week 6.

In certain implementations, the processing device can perform a trends analysis to determine a correlation coefficient for both TFC measurement and S3 vibration intensity. As shown in FIG. 16A, there may be a roughly linear relationship between the two metrics and, as such, there is likely to be a correlation coefficient that indicates a strong, positive association between the two variables. Such an association can be interpreted by the processing device as indicative of a particular adverse cardiac event that is characterized by a high correlation coefficient between TFC measurement and S3 vibration intensity. In certain implementations, the high correlation coefficient can also be indicative of a changing condition for the patient over a period of time, for example, six weeks as shown in FIG. 16A.

Figure 16B:
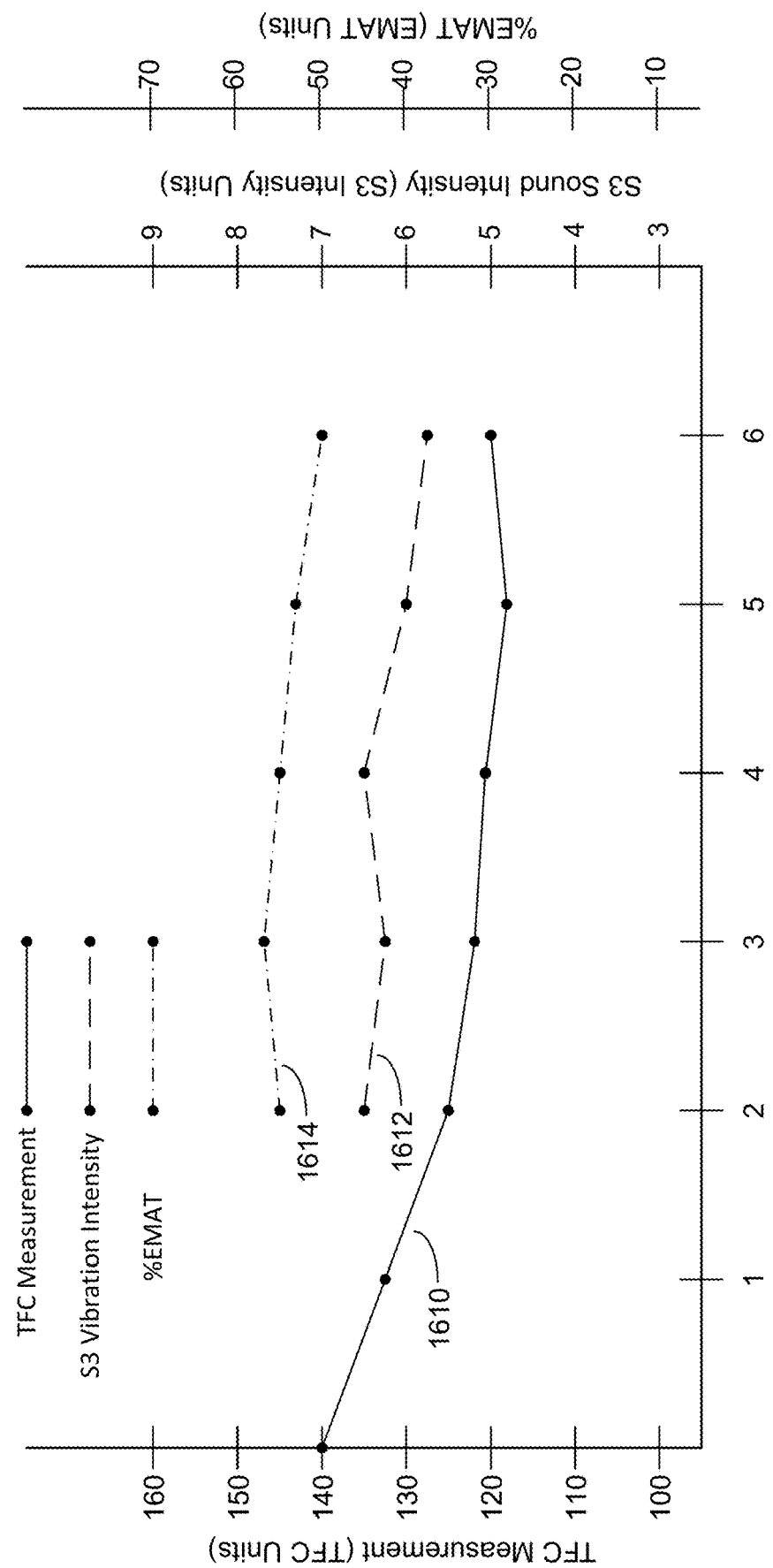

In certain implementations, a trends analysis can be used to determine how a treatment plan is working for a patient. For example, as shown in FIG. 16B, a patient may be monitored during a six-week treatment plan. Initially, the TFC measurement for the patient can be monitored, represented in FIG. 16B as line 1610. As shown in FIG. 16B, there is a measured drop over the initial two weeks of monitoring in the TFC measurement. Such a downward trend can trigger additional monitoring. For example, as shown in FIG. 16B, S3 vibration intensity as well as % EMAT, measured in % EMAT units on a normalized scale of, for example, 0-100% EMAT units (adjusted, as shown in FIG. 16B, to focus on a range of 10-70% EMAT units), can be triggered by the downward trend in TFC measurement. As shown in FIG. 16B, S3 vibration intensity is represented by line 1612 and % EMAT is represented by line 1614. Over the next four weeks, as further shown by FIG. 16B, each of TFC measurement, S3 vibration intensity, and % EMAT remain relatively steady or gradually decrease. Such a result can indicate that the treatment plan is progressing well. In implementations, other metrics may also be studied. For example, if the LVST also decreases over the same period, the device can confirm that the treatment plan is progressing well.

Figure 16C:
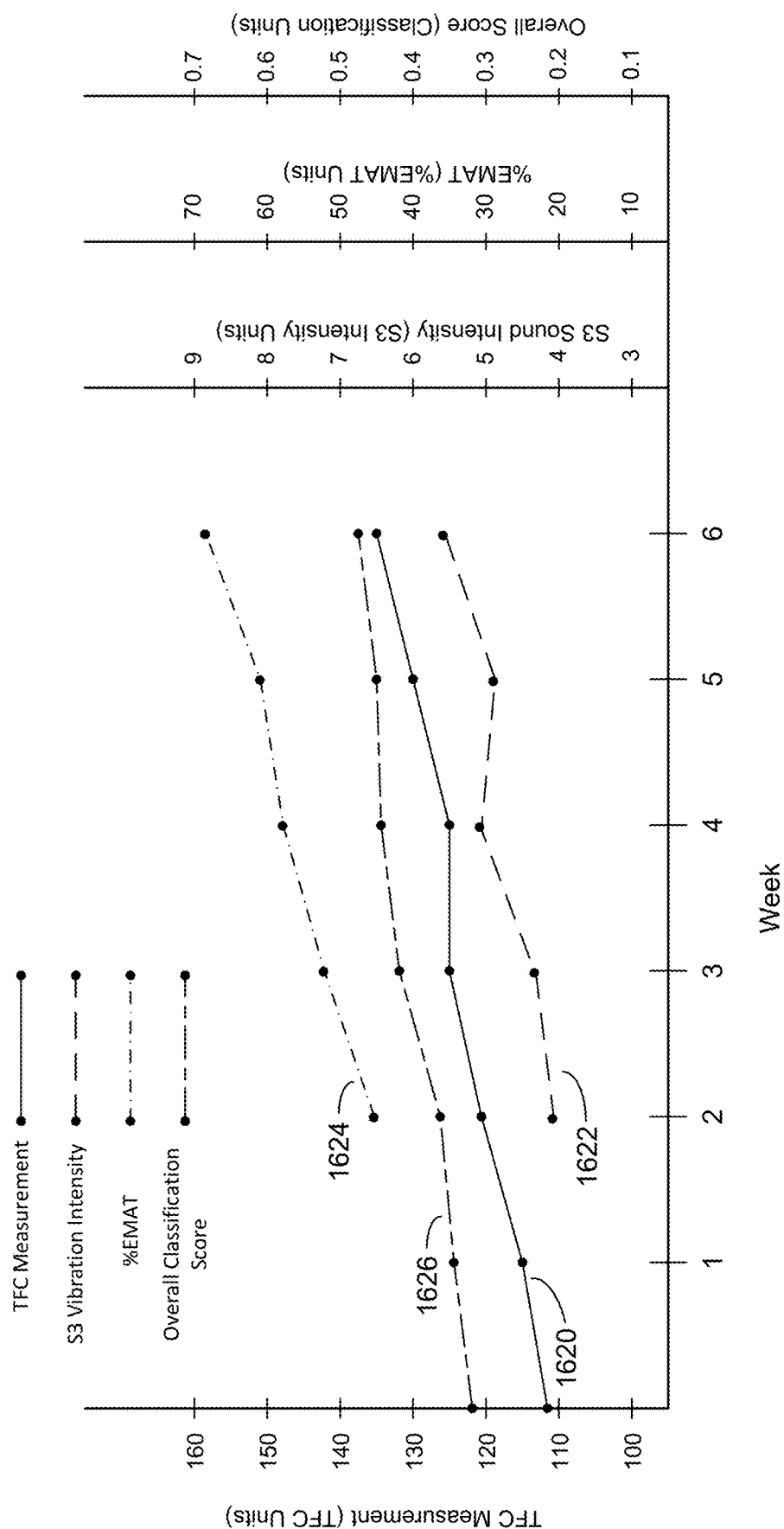

FIG. 16C shows a six-week trend analysis that includes an overall classification score for a patient. As shown in FIG. 16C, over the first two weeks the TFC measurement for the patient, represented by line 1620, can be trending upward, which produces a general increase in the patient's overall classification score, represented by line 1626. Like above, after two weeks of a constant trend, additional monitoring can be triggered. In this example, at week two both S3 vibration intensity and % EMAT monitoring can begin. As shown in FIG. 16C, S3 vibration intensity is represented by line 1622 and % EMAT is represented by line 1624. As further shown in FIG. 16C, each of TFC measurement, S3 vibration intensity, and % EMAT continue to increase between weeks two and six.

As a result of these monitored metric increases, the patient's overall classification score continues to increase. As noted above, the patient's overall classification score can be measured on a scale from 0.0 to 1.0 classification units, wherein 0.0 classification units is the best condition and 1.0 classification units is the worst condition. As shown in FIG. 16C, the illustrated overall classification score reading can be adjusted to focus on a range of, for example, 0.1-0.7 classification units. As the patient's overall score continues to increase, the monitoring device can determine whether the score has crossed a specific threshold (e.g., 0.50 classification units, or from one classification unit to another) and can provide feedback to, for example, the patient's physician accordingly. In implementations, other metrics may also be studied. For example, if the LVST also increases over the same period, the device can confirm that the intervention is necessary to change or manage the patient's treatment plan.

Figure 16D:
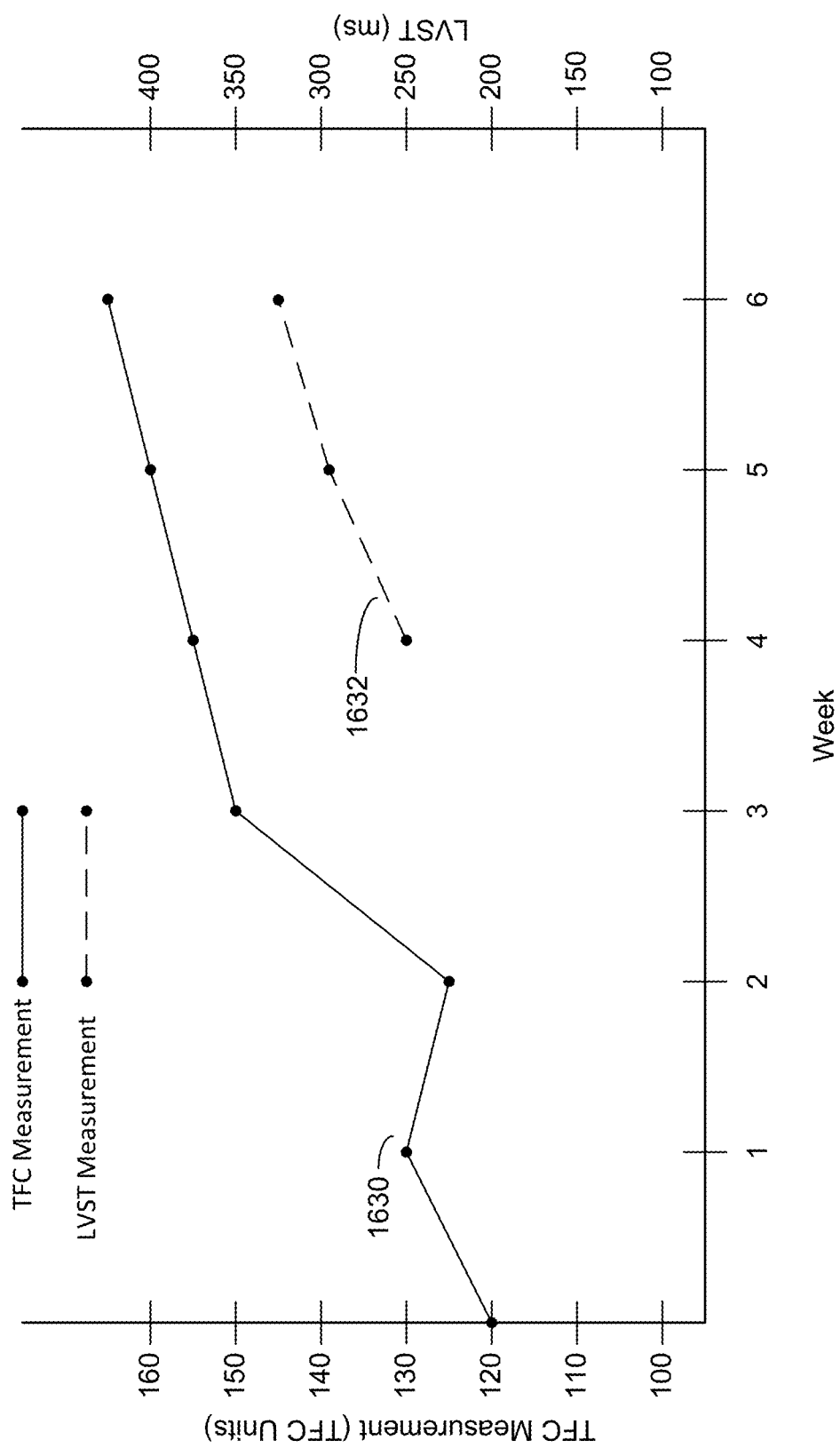

The metrics as shown in FIGS. 16A-C are provided by way of example. Additional metrics, such as LVST can be monitored and graphed over time as well. For example, as shown in FIG. 16D, the processing device can record the patient's TFC measurement over the course of several weeks, represented by line 1630. For example, an initial reading can include a TFC measurement of 120 TFC units. At week 1, the TFC measurement may increase to 130 TFC units. However, in week 2 the TFC measurement may decrease to 125 TFC units. At week 3, the TFC measurement may increase to 150 TFC units and at week 4 the TFC measurement may increase to 155 TFC units. Depending upon the programming of the processing device, the processing device may trigger a second metric measurement based upon the changes in TFC measurement. For example, the TFC measurement may have exceeded a predetermined threshold value (e.g., 150 TFC units) or the increase may be over a predetermined threshold period of time (e.g., two weeks of successive increases in TFC units, or an increase in three out of four weeks). These changes may trigger the processing device to monitor at least one additional metric. For example, at week 4 the processing device began measuring LVST as well, represented by line 1632 as shown in FIG. 16D.

For example, at week 4 the patient's LVST can be measured at approximately 250 ms. However, at week 5, the patient's LVST has increased to 290 ms, and by week 6 the patient's LVST has increased to 325 ms. During this same period, the patient's TFC measurement has continued to increase as well, e.g., to 160 TFC units in week 5, and to 165 TFC units in week 6. This increase in LVST can be used to confirm the interpretation that the thoracic fluid buildup in the patient is worsening, and as such, intervention is advised.

Conversely, if the TFC measurement substantially decreases from one week to the next, e.g., trends downwards from higher TFC units towards lower TFC units, the patient's LVST is likewise expected to decrease over the same period. The decrease in LVST can be used to confirm the interpretation that one or more interventional therapies for thoracic fluid management appears to be improving the patient's condition.

In certain implementations, the processing device can perform a trends analysis to determine a correlation coefficient for both TFC measurement and LVST. As shown in FIG. 16D, there is a roughly linear relationship between the two metrics and, as such, there is likely to be a correlation coefficient that indicates a positive association between the two variables. For example, the positive correlation coefficient can provide an indication that LVST increases as TFC measurement increases. Such an association indicating an increasing trend can be interpreted by the processing device as indicative of a particular adverse cardiac event that is characterized by a positive correlation coefficient between TFC measurement and LVST. In certain implementations, the positive correlation coefficient can also be indicative of a changing condition for the patient over a period of time, for example, six weeks as shown in FIG. 16D.

Figure 17:
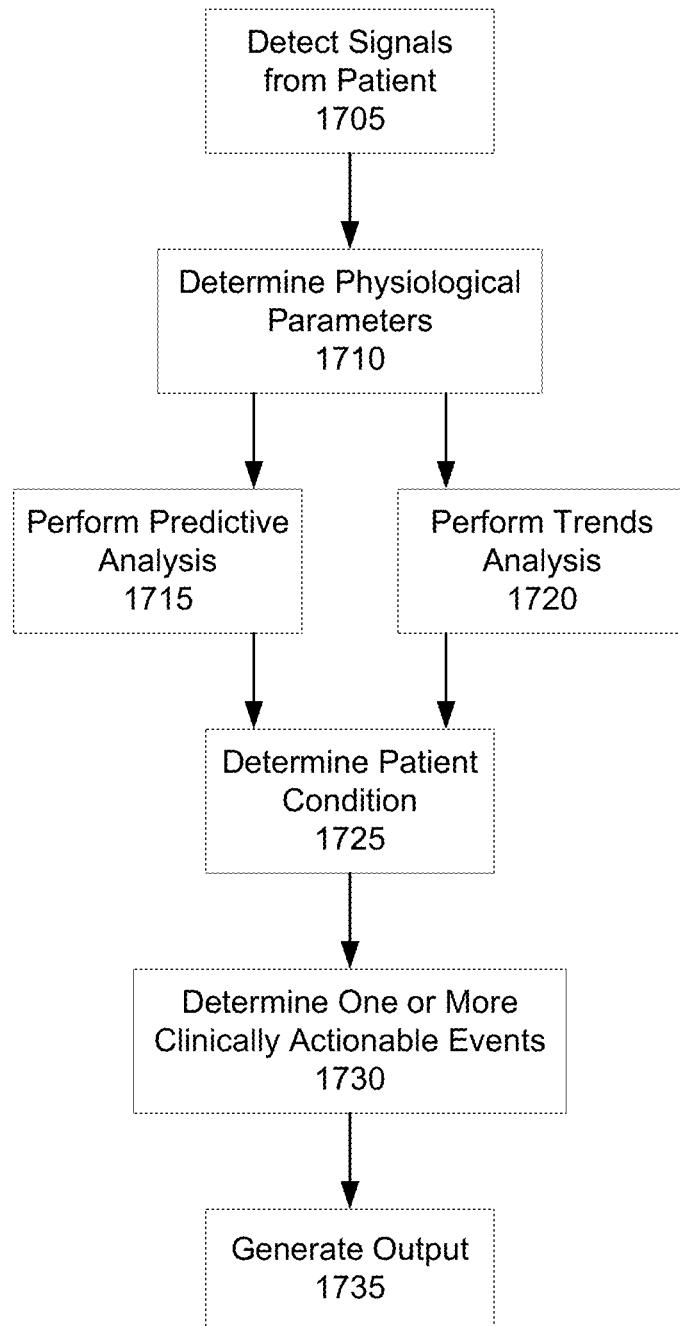
FIG. 17 depicts a sample process flow for monitoring a patient's condition using the techniques as described herein, in accordance with an example of the present disclosure.

FIG. 17 illustrates a sample process flow for a patient monitoring system as described herein. For example, a set of sensors can be configured to detect 1705 raw signals for a patient. In certain implementations, an ECG sensor can be configured to detect one or more ECG signals of the patient, a vibrational sensor can be configured to detect one or more bio-vibrational signals of the patient, and a radio frequency ultra-wide band transceiver can be configured to cause one or more antennas to direct radio frequency electromagnetic energy into the patient and produce radio frequency information responsive to reflected radio frequency electromagnetic energy received through the one or more antennas and reflected from a portion of the patient such as a main artery or the thoracic cavity.

In certain implementations, one or more processors can be configured to processes the raw signals to determine 1710 a set of physiological parameters for the patient. For example, as described herein, the physiological parameters can include ECG metrics, bio-vibration metrics, radio frequency metrics, and/or combinational physiological metrics. In some examples, the physiological parameters can be collected over a particular prior period of time. For example, the period of time can include at least 24 hours, at least 48 hours, at least one week, at least one month, at least six weeks, at least two months, at least four months, at least six months, at least one year, and at least two years. In some examples, the prior period of time corresponds to a period of time that clinical history is available for the patient.

The one or more processors can be further configured to use the physiological parameters to perform at least one of a predictive analysis 1715 or a trends analysis 1720. In certain implementations, the one or more processors can be configured to perform both the predictive analysis 1715 and the trends analysis 1720.

As described above, the predictive analysis 1715 can include entering the physiological parameters into a trained process. For example, the trained process can include an artificial neural network or machine learning process as described above. However, in certain implementations, the trained process can further include a deep learning process configured to analyze the physiological parameters and output current condition information for the patient.

Based upon the output of the predictive analysis and/or the trends analysis, the one or more processors can determine 1725 a current patient condition. Based upon the current patient condition, the one or more processors can determine 1730 one or more clinically actionable events for the patient. For example, the clinically actionable events can include re-hospitalization, prescription of a wearable medical device such as a wearable defibrillator, instructions to a patient to go to the hospital, changes in a treatment regimen, and other similar events. In certain implementations, the clinically actionable events can include an automated event that is triggered without user input such as increase monitoring and/or analysis of one or more physiological signals. Similarly, the clinically actionable event can include a manual event that is triggered based upon a user response. The clinically actionable event can generate output and can include one or more instructions to perform one or more actions such as instructions for a patient to go to the hospital.

The one or more processors can generate 1735 an output based upon the clinically actionable events. In certain implementations, the clinically actionable events can include an automated event that is triggered without user input such as increase monitoring and/or analysis of one or more physiological signals. Similarly, the clinically actionable event can include a manual event that is triggered based upon a user response. The clinically actionable event can generate output and can include one or more instructions to perform one or more actions such as instructions for a patient to go to the hospital.

Various studies have been performed to analyze and validate the ideas and techniques as described herein. For example, a study has been conducted to assess the value of cardiac-based bio-vibrational information as described herein, as well as combination of cardiac-based bio-vibrational information with one or more ECG metrics, in heart failure analysis. In the study, a subject population including subjects having an ejection fraction<35% and who have been hospitalized for decompensated heart failure were enrolled in a prospective observational protocol. All subjects were fitted with a WCD that was equipped with an accelerometer. The WCD was capable of recording bio-vibrations as well as measuring ECG signals. Each of the subjects were to wear the WCDs in an outpatient setting. The subject population was monitored for heart failure events and emergency room visits for heart failure symptoms and this information was collected for the subject population. Univariate and multivariate analyses were performed on the collected information to identify a model that best predicted the occurrence of early heart failure readmission or emergency room visits.

During the study, the subject population was divided into two groups based upon occurrence of heart failure events, resulting in a heart failure subject group and a non-heart failure subject group (based upon heart failure hospitalization and emergency room visit information for the subject population). The heart failure group had a lower BMI (26+/−5 vs 29+/−6) than the non-heart failure group, but all other demographic information was similar between the two groups. A multi-parameter model using heart rate, EMAT (from onset of QRS to S1), and S3 strength (based on, for example, S3 timing, intensity, persistence, and frequency) statistically produced the best predictive model for a decompensated heart failure event. Prior to the start of WCD wear, all-cause readmissions were similar between the two groups (62% for heart failure vs. 63% for non-heart failure) as were NYHA class I+II classifications (68% for heart failure vs. 69% for non-heart failure). However, after WCD use and model determination, the ability of NYHA class to predict heart failure events was lower than through the use of bio-vibrational information. For example, the bio-vibrational information predictor had a sensitivity of 68% with a positive predictive value of 28% as compared to a sensitivity of 30% and a positive predictive value of 18% for the NYHA classification system. Thus, based upon the study, one can conclude that the use of bio-vibrational information alone or combination with ECG information and radio frequency-determined lung fluid levels (as discussed below) may be useful in early detection of decompensated heart failure in at-risk patients than the traditional NYHA classification system. Such heart failure that may result in a subject's readmission to hospital after an episode of acute decompensated heart failure.

A second study has been conducted to provide insight into using radio frequency-determined lung fluid levels to track disease status in heart failure subjects. A subject population included two groups. The first group included acute heart failure subjects having the following statistics: age 78 years+/−8 years; 37% female; and BMI=32+/−7. The second group included subjects without acute heart failure (approximately 60% healthy and 40% stable heart failure patients), the second group having the following statistics: age 56 years+/−16 years; 27% female; and BMI=27+/−5.

Each subject in the population underwent a supine thoracic CT scan to determine initial fluid levels. This was followed with supine RF readings from a wearable patch device placed on the left mid-axillary line. An RF-based lung fluid model was built for each patient using reflected RF signals as measured by the patch device as well as anthropometric data. Lung fluid was reported as a percentage of lung volume. Classification analysis techniques were then used to compare RF patch device and thoracic CT scan results and performance.

The results of the above study indicated that all acute heart failure subjects measured as having higher lung fluid levels than the non-acute heart failure subjects. Statistically, the RF patch design performed as well as the thoracic CT scan to identify acute heart failure subjects from non-acute heart failure subjects. Sample data showing various determined statistical results from this study can be seen in TABLE 10 below.

TABLE 10

| AHF vs Control | Sensitivity [%] | Specificity [%] | Positive Predictive Value [%] | Negative Predictive Value [%] | Positive Likelihood Ratio | Negative Likelihood Ratio |
|---|---|---|---|---|---|---|
| RF model | 78 | 85 | 84 | 79 | 5.1 | 0.3 |
| CT | 74 | 85 | 83 | 76 | 4.8 | 0.3 |

The data as obtained from the two studies as described above illustrates that radio frequency data can be used to assess whether a particular patient should be considered as a heart failure patient or an acute heart failure patient.

Additionally, using techniques as described above, bio-vibrational data for a patient can be incorporated with the patient's radio frequency data to show trends or changes in the medical condition of a patient. For example, using the combinational physiological parameter analysis as is described herein, patient information such as bio-vibrational information and radio frequency data can be combined with measured ECG information into one or more combinational metrics. Using correlation analysis as described herein (or, in other examples, another similar machine learning technique as described above), the patient information can be transformed or otherwise processed to quantify one or more trends or changes in the patient's medical condition. The trends can be further analyzed to determine what additional information can be determined from the trends. For example, the trends can be further analyzed to determine information such as is the patient's overall health improving/getting worse, is the patient's cardiac health improving/getting worse, and/or is the patient likely to suffer another heart failure event that may require an emergency room visit or hospital readmission in the near future (e.g., the next 30 days). Combinational physiological parameters based upon, for example, patient radio frequency and bio-vibrational data can also be used to determine whether a patient that is being discharged is likely to experience a heart failure event in the near future and/or should be prescribed an ambulatory medical device such as a WCD as described in an example below.

In an example, a person may complain of chest pains when performing certain activities such as sitting in a reclined position or lying on their back. Their physician may prescribe the patient a radio frequency sensing device to wear, the device configured to measure the patient's TFC. The patient can wear the device over the course of several weeks. Over the time period, the device can measure a steady increase of fluid content in the patient's thoracic cavity. Upon returning to the physician, the physician may download the data recorded by the radio frequency sensing device into a trends analysis process. The process can detect a trend indicating that the patient's TFC is steadily increasing. The physician may want to obtain additional physiological information for the patient and may further prescribe a mobile cardiac monitoring device that includes a vibrational sensor configured to measure bio-vibrations. The patient wears both the radio frequency sensing device and the mobile cardiac monitoring device for a period of time. Upon returning to the physician, the recorded information from both monitoring devices can be entered into the trends analysis process. The process may confirm the trend indicating that the patient's TFC is increasing by analyzing information related to the patient's S3 vibration intensity. The process may determine a correlation between the TFC increase and the patient's S3 vibration intensity, providing an indication that the patient is likely suffering from a cardiac condition such as congestive heart failure. The process may provide the physician with such an indication along with a recommended action to take such as modification to the patient's prescribed drugs.

In another example, during a hospital stay a patient may wear at least one ECG sensor, at least one bio-vibrational sensor, and at least one radio frequency sensor. Prior to being discharged, data recorded by these sensors can be combined into one or more combinational physiological parameters and input into a trained process such as an artificial neural network (or, in other examples, another similar machine learning technique as described above). The artificial neural network can transform the input information to provide clinical condition information for the patient. This clinical condition information can be further analyzed to determine the current condition of the patient, whether the patient is approved for discharge, and what the risk is for re-hospitalization of the patient within a specific time, e.g., within 30 days. In some examples, even if the patient completes all necessary requirements for discharge, the process may indicate that the patient has a high risk for re-hospitalization in the near future. In such an example, a physician or other similar caregiver may decide to keep the patient in the hospital for additional monitoring, change the treatment regimen for the patient, or otherwise alter the care being provided to the patient.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. An externally worn cardiac monitoring and treatment system comprising:
    an ECG sensor coupled to a patient and configured to detect one or more ECG signals of the patient;
    a therapy electrode configured to deliver a therapeutic shock to the patient;
    a vibrational sensor coupled to the patient and configured to detect one or more cardio-vibrational signals of the patient;
    a radiofrequency transceiver circuit comprising one or more radiofrequency antennas, the radiofrequency transceiver circuit configured to
        cause the one or more radiofrequency antennas to direct radiofrequency energy into at least a portion of the patient, and
        produce radiofrequency information responsive to reflected radiofrequency energy that is received through the one or more radiofrequency antennas and that is reflected from within the patient; and
    one or more processors configured to
        process the one or more ECG signals and the one or more cardio-vibrational signals to generate a combinational parameter,
        process the radiofrequency information to generate a thoracic fluid content measurement of the patient,
        perform a correlation analysis on the combinational parameter and the thoracic fluid content measurement to determine a current clinical condition of the patient, wherein the current clinical condition of the patient indicates a possible occurrence of a cardiac arrhythmia,
        compare the current clinical condition of the patient to predetermined clinically actionable criteria to identify one or more clinically actionable events, and cause an output device to provide an output relating to the one or more clinically actionable events; and therapy delivery circuitry that is operably connected to the therapy electrode and that is configured to treat the cardiac arrhythmia by providing a therapeutic shock to the patient using the therapy electrode.

2. The system of claim 1, wherein the correlation analysis is performed on the combinational parameter and the thoracic fluid content measurement over a prior period of time including one or more of: at least 24 hours, at least 48 hours, at least one week, at least two weeks, at least one month, at least 6 weeks, at least two months, at least 4 months, at least 6 months, at least 1 year, or at least 2 years.

3. The system of claim 1, wherein the correlation analysis is performed on the combinational parameter and the thoracic fluid content measurement over a prior period of time corresponding to at least an available clinical history of the patient.

4. The system of claim 1, wherein the one or more clinically actionable events comprise at least one of:
an automated event that is triggered without user input; or
a manual event that is triggered based upon a user response to the output and comprises one or more instructions to perform one or more actions.

5. The system of claim 4, wherein the automated event comprises configuring the cardiac monitoring and treatment system to increase a sensitivity of an ECG signal detection process for a period of time.

6. The system of claim 1, wherein the output relating to the one or more clinically actionable events is based on a transgression of one or more thresholds defined with respect to results of the correlation analysis.

7. The system of claim 1, wherein the current clinical condition of the patient comprises a predictive score that indicates a likelihood of the cardiac arrhythmia.

8. The system of claim 1, wherein performing the correlation analysis further comprises determining that at least one of:
the combinational parameter has exceeded a combinational parameter threshold; or
the thoracic fluid content measurement has exceeded a thoracic fluid content measurement threshold.

9. The system of claim 1, wherein performing the correlation analysis further comprises calculating a correlation score that indicates a change in the current clinical condition of the patient.

10. The system of claim 1, wherein the vibrational sensor is further configured to sense one or more lung vibrations for the patient, the one or more lung vibrations comprising at least one of bronchial vibrations, stridor, crackle, wheeze, rhonchus, pleural friction, squawk, glottal, pharyngeal, or other vibrations.

11. The system of claim 1, wherein the one or more ECG signals comprise at least one of heart rate; heart rate variability; PVC burden or counts; atrial fibrillation burden; pauses; heart rate turbulence; QRS height; QRS width; changes in size or shape of ECG morphology; cosine R-T; artificial pacing; QT interval; QT variability; T wave width; T wave alternans; T-wave variability; or ST segment changes.

12. The system of claim 1, wherein the one or more processors are further configured to perform a predictive analysis of a determined value of, or a trend in, the thoracic fluid content measurement.

13. The system of claim 1, wherein the one or more processors are further configured to display, via the output device, a graphical timeline representing at least a portion of a monitoring period during which the cardiac monitoring and treatment system is worn by the patient.

14. The system of claim 13, wherein the graphical timeline visually depicts a correlation between the combinational parameter and the thoracic fluid content measurement.

15. The system of claim 13, wherein the monitoring period comprises one or more of at least 24 hours, at least 48 hours, at least one week, or at least two weeks.

16. The system of claim 1, further comprising a garment, wherein the ECG sensor, the therapy electrode, and the vibrational sensor are coupled to the garment.

17. The system of claim 1, wherein the one or more processors are further configured to perform a trend analysis on the combinational parameter to generate an overall classification score for the patient.

18. The system of claim 17, wherein the one or more processors are further configured to update a monitoring schedule for the patient based on results of the trend analysis.

19. The system of claim 1, wherein the combinational parameter comprises electromechanical activation time.

20. The system of claim 1, wherein the combinational parameter comprises % LVST.

21. The system of claim 1, wherein the one or more cardio-vibrational signals include at least one of an S1 vibration, an S2 vibration, an S3 vibration, an S4 vibration, or a heart murmur vibration.

22. The system of claim 1, wherein the one or more processors are further configured to determine a left ventricular systolic time metric based on the one or more cardio-vibrational signals.

23. The system of claim 1, wherein the one or more cardio-vibrational signals comprise at least one of an S1 vibration, an S2 vibration, an S3 vibration, or an S4 vibration.

24. The system of claim 1, wherein the one or more cardio-vibrational signals comprise a heart murmur vibration.

* * * * *